(12) United States Patent
Hayashi et al.

(10) Patent No.: US 8,916,594 B2
(45) Date of Patent: Dec. 23, 2014

(54) 5-MEMBERED RING HETEROAROMATIC DERIVATIVES HAVING NPY Y5 RECEPTOR ANTAGONISTIC ACTIVITY

(75) Inventors: Kyohei Hayashi, Osaka (JP); Yuusuke Tamura, Osaka (JP); Naoki Omori, Osaka (JP)

(73) Assignee: Shionogi & Co., Ltd., Osaka-shi (JP)

( * ) Notice: Subject to any disclaimer, the term of this patent is extended or adjusted under 35 U.S.C. 154(b) by 0 days.

(21) Appl. No.: 14/114,113

(22) PCT Filed: Apr. 25, 2012

(86) PCT No.: PCT/JP2012/061032
§ 371 (c)(1),
(2), (4) Date: Oct. 28, 2013

(87) PCT Pub. No.: WO2012/147764
PCT Pub. Date: Nov. 1, 2012

(65) Prior Publication Data
US 2014/0051862 A1  Feb. 20, 2014

(30) Foreign Application Priority Data

Apr. 27, 2011  (JP) .................................. 2011-099397
Nov. 10, 2011  (JP) .................................. 2011-246469

(51) Int. Cl.
| | | |
|---|---|---|
| A61K 31/4439 | (2006.01) | |
| A61K 31/4245 | (2006.01) | |
| C07D 413/04 | (2006.01) | |
| C07D 271/07 | (2006.01) | |
| C07D 277/42 | (2006.01) | |
| C07D 271/10 | (2006.01) | |
| C07D 263/48 | (2006.01) | |
| C07D 277/20 | (2006.01) | |
| C07D 271/06 | (2006.01) | |
| A61K 45/06 | (2006.01) | |
| C07D 285/08 | (2006.01) | |
| C07D 271/113 | (2006.01) | |

(52) U.S. Cl.
CPC .......... *C07D 271/113* (2013.01); *C07D 413/04* (2013.01); *C07D 277/42* (2013.01); *A61K 31/4245* (2013.01); *C07D 271/10* (2013.01); *C07D 263/48* (2013.01); *C07D 277/20* (2013.01); *C07D 271/06* (2013.01); *A61K 45/06* (2013.01); *A61K 31/4439* (2013.01); *C07D 271/07* (2013.01); *C07D 285/08* (2013.01)
USPC .......... 514/364; 514/340; 546/269.4; 548/133

(58) Field of Classification Search
CPC .............. C07D 413/04; C07D 271/07; A61K 31/4439; A61K 31/4245
USPC ................ 514/340, 364; 546/269.4; 548/133
See application file for complete search history.

(56) References Cited

U.S. PATENT DOCUMENTS

| | | |
|---|---|---|
| 3,822,280 A | 7/1974 | Moser et al. |
| 3,917,478 A | 11/1975 | Moser et al. |
| 6,124,331 A | 9/2000 | Marzabadi et al. |
| 6,214,853 B1 | 4/2001 | Marzabadi et al. |
| 6,699,891 B1 | 3/2004 | Kawanishi et al. |
| 6,989,379 B1 | 1/2006 | Marzabadi et al. |
| 2006/0293341 A1 | 12/2006 | Jubian et al. |
| 2007/0015762 A1 | 1/2007 | Kawanishi et al. |
| 2009/0137590 A1 | 5/2009 | Ma et al. |
| 2010/0063027 A1 | 3/2010 | Okuno et al. |
| 2010/0267945 A1 | 10/2010 | Okuno et al. |
| 2010/0273841 A1 | 10/2010 | Okuno et al. |
| 2010/0273842 A1 | 10/2010 | Okuno et al. |
| 2010/0292500 A1 | 11/2010 | Kawanishi et al. |
| 2011/0039802 A1 | 2/2011 | Kawanishi et al. |

FOREIGN PATENT DOCUMENTS

| | | |
|---|---|---|
| EP | 0 667 865 | 8/1995 |
| EP | 1 249 233 A1 | 10/2002 |
| EP | 2 014 285 A1 | 1/2009 |
| EP | 2 017 261 A1 | 1/2009 |
| JP | 2010-270114 A | 12/2010 |
| WO | 94/10159 | 5/1994 |
| WO | WO 9931072 A1 * | 6/1999 |

(Continued)

OTHER PUBLICATIONS

International Search Report issued May 29, 2012, in PCT/JP2012/061032.

(Continued)

*Primary Examiner* — Joseph Kosack
*Assistant Examiner* — Matthew Coughlin
(74) *Attorney, Agent, or Firm* — Oblon, Spivak, McClelland, Maier & Neustadt, L.L.P.

(57) ABSTRACT

This invention provides new compounds having NPY Y5 antagonistic activity. The present inventors found that a compound of the formula (I):

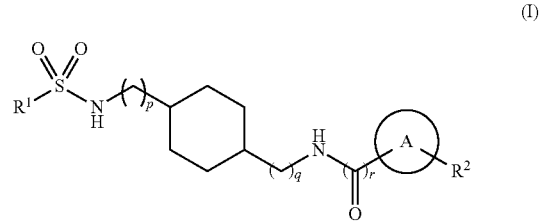

wherein $R^1$ is substituted or unsubstituted alkyl or the like; p, q and r are each independently 0 or 1; ring A is oxadiazole; and $R^2$ is substituted or unsubstituted alkyl or the like, has NPY Y5 antagonistic activity.

14 Claims, No Drawings

(56) References Cited

FOREIGN PATENT DOCUMENTS

| WO | WO 00/64880 A1 | 11/2000 |
|----|----|----|
| WO | WO 01/02379 A1 | 1/2001 |
| WO | WO 01/37826 A1 | 5/2001 |
| WO | WO 2007/002126 A1 | 1/2007 |
| WO | WO 2007/103295 A2 | 9/2007 |
| WO | WO 2007/125952 A1 | 11/2007 |
| WO | WO 2008/039023 A1 | 4/2008 |
| WO | WO 2009/014910 A2 | 1/2009 |
| WO | WO 2009/035855 A2 | 3/2009 |
| WO | WO 2009/054434 A1 | 4/2009 |
| WO | 2009/070485 | 6/2009 |

OTHER PUBLICATIONS

Henry C. Brown, et al., "Reactions of Perfluoroalkyl Nitriles. VII. Perfluoroacyl Amidoximes and 3,5-Bis(perfluoroalkyl)-1,2,4-oxadiazoles", J. Org. Chem., vol. 30, Nov. 1965, pp. 3734-3738.

Sarah J. Dolman, et al., "Superior Reactivity of Thiosemicarbazides in the Synthesis of 2-Amino-1,3,4-oxadiazoles", J. Org. Chem., vol. 71, No. 25, 2006, pp. 9548-9551.

Lars Grundemar, et al., "Neuropeptide Y effector systems: perspectives for drug development", TIPS Reviews, vol. 15, May 1994, pp. 153-159.

Catalina Betancur, et al., "Nonpeptide antagonists of neuropeptide receptors: tools for research and therapy", TIPS Review, vol. 18, Oct. 1997, pp. 372-386.

Ambikaipakan Balasubramaniam, "Neuropeptide Y Family of Hormones: Receptor Subtypes and Antagonists", Peptides, vol. 18, No. 3, 1997, pp. 445-457.

Hideo Yukioka, et al., "A Potent and Selective Neuropeptide Y Y5 Receptor Antagonist, S-2367, Attenuates the Development of Diet-Induced Obesity in Mice", Obesity, vol. 14, No. 9, 2006, p. A235 (Abstract only).

Atsuyuki Shimazaki, et al., "Role of Energy Expenditure in the Antiobesity Effect of Neuropeptide Y Y5 Receptor in Antagonist S-2367 in Diet-Induced Obese Mice", Obesity, vol. 15, No. 9, 2007, p. A57 (Abstract only).

Supplementary European Search Report issued Sep. 14, 2014, in European Patent Application No. 12 77 7012.

\* cited by examiner

5-MEMBERED RING HETEROAROMATIC DERIVATIVES HAVING NPY Y5 RECEPTOR ANTAGONISTIC ACTIVITY

FIELD OF THE INVENTION

This invention relates to a novel 5-membered aromatic heterocycle compound having an NPY Y5 receptor antagonistic activity and relates to 5-membered aromatic heterocycle derivatives useful for a pharmaceutical composition, especially for an anti-obesity drug.

BACKGROUND ART

Obesity is defined as an excessively high amount of body fat or adipose tissue in relation to lean body mass and recognized as a major risk factor for health problems. Body mass index (BMI) is a simple index of weight-for-height that is commonly used in classifying overweight and obesity in adult (age 15 and over) populations and individuals. It is defined as the weight in kilograms divided by the square of the height in meters ($kg/m^2$). World Health Organization defines "overweight" as a BMI of 25 $kg/m^2$ or greater and "obesity" as a BMI of 30 $kg/m^2$ or greater. On the other hand, Japan Society for the Study of Obesity defines "obesity" as a BMI of 25 $kg/m^2$ or greater because the number of obesity-related disorders including diabetes and dislipidemia increases in accordance with BMI, and the mean number of obesity-related disorders is greater than 1.0 at a BMI of 25 $kg/m^2$. World Health Organization reported that about 1600 million and at least 400 million people were classified as overweight and obesity around the world in 2005, respectively. Obesity is mainly caused by taking in more calories than using up in physical activity and daily life. The number of obese people has been increasing by taking in more food including high fat and/or sugar, and it is estimated that 700 million people or more would be diagnosed as obesity around the world in 2015.

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulatory action on food intake, an anti-seizure activity, a learning-enhancing action, an anti-anxiety activity, an anti-stress activity, etc. in the central nervous system, and it may be pivotally involved in central nervous system diseases such as depression, Alzheimer's disease, Parkinson's disease. NPY is thought to be involved in cardiovascular diseases, since it induces a contraction of smooth muscles such as blood vessels or cardiac muscles in peripheral tissues. Furthermore, NPY is also known to be involved in metabolic diseases such as obesity, diabetes, hormone abnormalities (Non-patent Document 1). Therefore, an NPY receptor antagonist is expected as medicine for preventing or treating the above-mentioned various diseases associated with the NPY receptor.

Six subtypes of NPY receptors have now been identified: Y1, Y2, Y3, Y4, Y5 and Y6 (Non-patent Document 2). It has been suggested that the Y5 receptor is at least involved in the feeding behavior and its antagonist is expected as an anti-obesity drug (Non-patent Documents 3 to 5).

Thiazole derivatives exhibiting an NPY Y5 receptor antagonistic activity are disclosed in Patent Documents 1 to 6.

Oxadiazole derivatives exhibiting an NPY Y5 receptor antagonistic activity are disclosed in Patent Documents 7 to 11.

PRIOR ART DOCUMENTS

Patent Documents

[Patent Document 1] US2006/0293341
[Patent Document 2] WO2009/35855
[Patent Document 3] WO2007/103295
[Patent Document 4] WO2007/2126
[Patent Document 5] WO2000/64880
[Patent Document 6] WO2001/2379
[Patent Document 7] JP2010/270114
[Patent Document 8] WO2009/54434
[Patent Document 9] US2010/273842
[Patent Document 10] US2010/273841
[Patent Document 11] WO2007/125952

Non-Patent Documents

[Non-patent Document 1] Trends in Pharmacological Sciences, Vol. 15, 153 (1994)
[Non-patent Document 2] Trends in Pharmacological Sciences, Vol. 18, 372 (1997)
[Non-patent Document 3] Peptides, Vol. 18, 445 (1997)
[Non-patent Document 4] Obesity, Vol. 14, No. 9, A235 (2006)
[Non-patent Document 5] Obesity, Vol. 15, No. 9, A57 (2007)

DISCLOSURE OF INVENTION

Problems to be Solved by the Invention

The object of this invention is to provide novel 5-membered aromatic heterocycle derivatives having a high NPY Y5 receptor antagonistic activity.

Means for Solving the Problem

The present inventors have achieved to synthesize the novel 5-membered aromatic heterocycle derivatives exhibiting a high NPY Y5 receptor antagonistic activity through their intensive studies. Moreover, the present inventors found that the compounds have the effect of the suppressing food intake. In addition, the present inventors found that the compounds of the invention have a weak inhibition against drug metabolizing enzyme, great metabolic stability and high water solubility. Furthermore, the compounds of the invention were less toxic, therefore it is thought to be safe enough for pharmaceutical use.

This invention includes the followings.

(1) A compound of the formula (I):

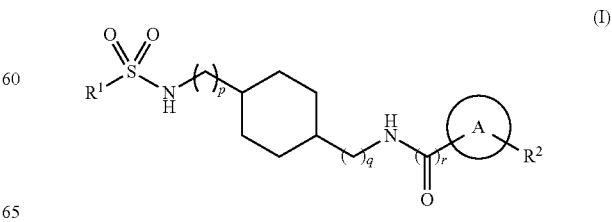

or its pharmaceutically acceptable salt, wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p, q and r are each independently 0 or 1, ring A is oxadiazole, and R² is substituted or unsubstituted alkyl, substituted or unsubstituted cycloalkyl, substituted or unsubstituted aryl, substituted or unsubstituted heteroaryl or substituted or unsubstituted heterocyclyl, provided that the following compounds are excluded,

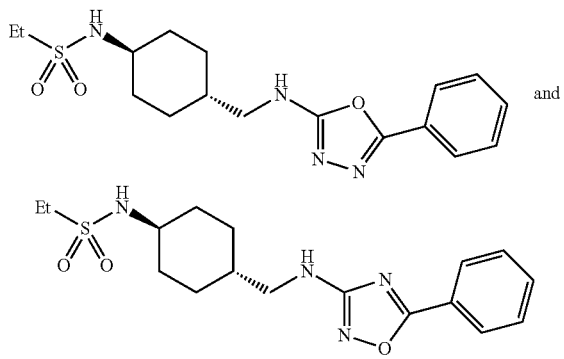 and

Additionally, this invention includes the followings.

(2) The compound or its pharmaceutically acceptable salt of the above (1), wherein p is 1, and q and r are 0.

(3) The compound or its pharmaceutically acceptable salt of the above (1) or (2), wherein R¹ is substituted or unsubstituted alkyl.

(4) The compound or its pharmaceutically acceptable salt of any one of the above (1) to (3), wherein a group of the formula:

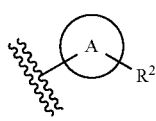

is a group of the formula:

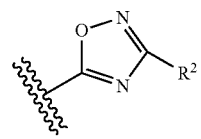

(5) The compound or its pharmaceutically acceptable salt of any one of the above (1) to (4), wherein R² is substituted or unsubstituted aryl.

(6) The compound or its pharmaceutically acceptable salt of the above (5), wherein R² is a group of the formula:

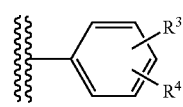

wherein R³ is halogen, alkylsulfonyl, haloalkyl or haloalkyloxy, and R⁴ is hydrogen, halogen, alkylsulfonyl, haloalkyl or haloalkyloxy.

(7) A pharmaceutical composition comprising the compound or its pharmaceutically acceptable salt of any one of the above (1) to (6).

(8) The pharmaceutical composition of the above (7) having NPY Y5 receptor antagonistic activity.

(9) The compound or its pharmaceutically acceptable salt of any one of the above (1) to (6) for treatment or prevention of a disease associated with NPY Y5.

(10) A method for treatment or prevention of a disease associated with NPY Y5 characterized by administering the compound or its pharmaceutically acceptable salt of any one of the above (1) to (6).

(11) A compound of the formula (II):

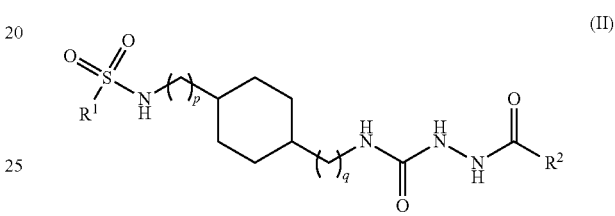

(II)

or its salt, wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, R² is substituted or unsubstituted alkyl, substituted or unsubstituted cycloalkyl, substituted or unsubstituted aryl, substituted or unsubstituted heteroaryl or substituted or unsubstituted heterocyclyl, and p and q are each independently 0 or 1.

(12) A compound of the formula (III):

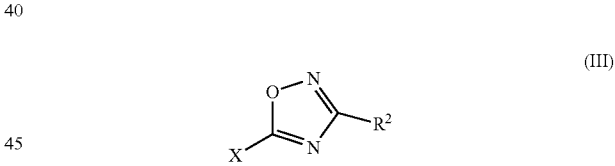

(III)

or its salt, wherein X is halogen or trihalogenomethyl, and

R² is substituted or unsubstituted cycloalkyl, substituted or unsubstituted aryl, substituted or unsubstituted heteroaryl or substituted or unsubstituted heterocyclyl.

(1') A compound of the formula (I):

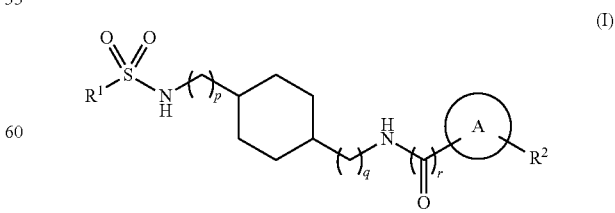

(I)

or its pharmaceutically acceptable salt, wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino,
p, q and r are each independently 0 or 1,
ring A is oxadiazole, and
R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, provided that the following compounds are excluded,

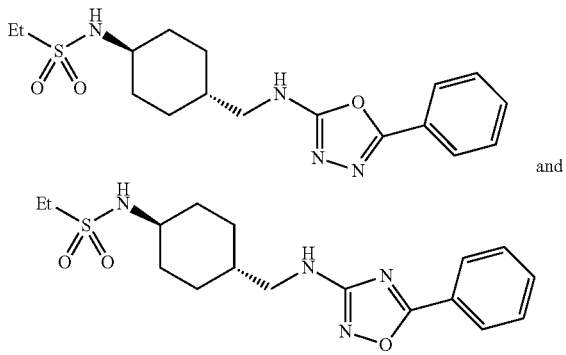

and (2') The compound or its pharmaceutically acceptable salt of the above (1'), wherein p is 1, and q and r are 0.
(3') The compound or its pharmaceutically acceptable salt of the above (1') or (2'), wherein R¹ is substituted or unsubstituted alkyl or substituted or unsubstituted cycloalkyl.
(4') The compound or its pharmaceutically acceptable salt of the above (3'), wherein R¹ is substituted or unsubstituted alkyl.
(5') The compound or its pharmaceutically acceptable salt of any one of the above (1') to (4'), wherein a group of the formula:

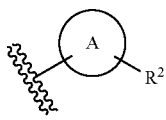

is a group of the formula:

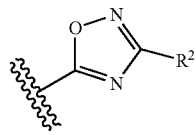

(6') The compound or its pharmaceutically acceptable salt of the above (5'), wherein R² is substituted or unsubstituted aryl.
(7') The compound or its pharmaceutically acceptable salt of the above (5'), wherein R² is a group of the formula:

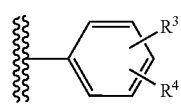

wherein
R³ is halogen, alkylsulfonyl, haloalkyl or haloalkyloxy, and
R⁴ is hydrogen, halogen, alkylsulfonyl, haloalkyl or haloalkyloxy.
(8') The compound or its pharmaceutically acceptable salt of the above (5'), wherein R² is substituted or unsubstituted alkyl.
(9') The compound or its pharmaceutically acceptable salt of the above (5'), wherein R² is substituted or unsubstituted haloalkyl.
(10') The compound or its pharmaceutically acceptable salt of the above (5'), wherein R² is substituted or unsubstituted cycloalkyl, substituted or unsubstituted cycloalkenyl or substituted or unsubstituted heterocyclyl.
(11') The compound or its pharmaceutically acceptable salt of the above (5'), wherein R² is substituted or unsubstituted cycloalkyl.
(12') A compound of the formula (IV):

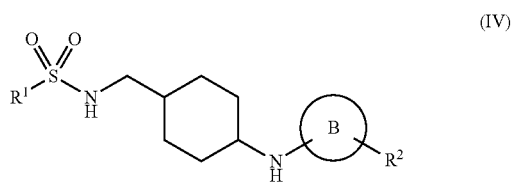

or a its pharmaceutically acceptable salt,
wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, ring B is 5-membered aromatic heterocycle, and
R² is substituted or unsubstituted haloalkyl, substituted or unsubstituted cycloalkyl, substituted or unsubstituted cycloalkenyl or substituted or unsubstituted heterocyclyl.
(13') The compound or its pharmaceutically acceptable salt of the above (12'), wherein ring B is oxadiazole, thiadiazole, imidazole, thiazole or oxazole.
(14') The compound or its pharmaceutically acceptable salt of the above (13'), wherein ring B is oxadiazole or oxazole.
(15') The compound or its pharmaceutically acceptable salt of any one of the above (12') to (14'), wherein R¹ is substituted or unsubstituted alkyl or substituted or unsubstituted cycloalkyl.
(16') The compound or pharmaceutically acceptable salt of the above (15'), wherein R¹ is substituted or unsubstituted alkyl.
(17') The compound or its pharmaceutically acceptable salt of the above (12'), wherein a group of the formula:

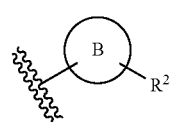

is a group of the formula:

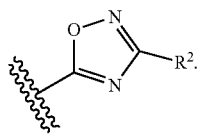

(18') The compound or its pharmaceutically acceptable salt of any one of the above (12') to (17'),
wherein $R^2$ is substituted or unsubstituted haloalkyl.
(19') The compound or its pharmaceutically acceptable salt of any one of the above (12') to (17'), wherein $R^2$ is substituted or unsubstituted cycloalkyl, substituted or unsubstituted cycloalkenyl or substituted or unsubstituted heterocyclyl.
(20') The compound or its pharmaceutically acceptable salt of the above (19'), wherein $R^2$ is substituted or unsubstituted cycloalkyl.
(21') A pharmaceutical composition comprising the compound or its pharmaceutically acceptable salt of any one of the above (1') to (20').
(22') The pharmaceutical composition of the above (21') having NPY Y5 receptor antagonistic activity.
(23') A compound of the formula (II):

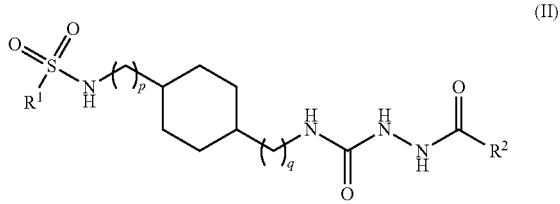

or its salt,
wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino,
$R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and p and q are each independently 0 or 1.
(24') A compound of the formula (III):

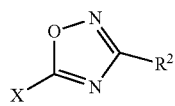

or its salt,
wherein X is halogen or trihalogenomethyl, and
$R^2$ is substituted or unsubstituted haloalkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.
(25') The compound or salt of the above (24'),
wherein $R^2$ is substituted or unsubstituted haloalkyl or substituted or unsubstituted cycloalkyl.

(26') The compound or its pharmaceutically acceptable salt of any one of the above (1') to (20') for treatment or prevention of a disease associated with NPY Y5.
(27') A method for treatment or prevention of a disease associated with NPY Y5 characterized by administering the compound or its pharmaceutically acceptable salt of any one of the above (1') to (20').

Effect of the Invention

The compound of the invention exhibits NPY Y5 receptor antagonistic activity and is very useful as a medicine especially for preventing or treating a disease associated with NPY Y5, e.g. feeding disorder, obesity, hyperorexia, sexual disorder, impaired fertility, depression, epileptic seizure, hypertension, cerebral hemorrhage, congestive heart failure or sleep disorders. Moreover, the compound of the invention exhibits the good effect of suppressing food intake and is very useful for the weight management, the weight loss and weight maintenance after the weight loss for obesity. In addition, the compound of the invention is effective for preventing or treating the diseases in which obesity acts as a risk factor, for example, diabetes, hypertension, hyperlipemia, atherosclerosis and acute coronary syndrome.

BEST MODE FOR CARRYING OUT THE INVENTION

Terms used in the present description are explained below. Each term has the same meaning alone or together with other terms in this description.
"Halogen" includes fluorine, chlorine, bromine and iodine. Especially preferred is fluorine or chlorine.
"Alkyl" includes C1 to C10 straight or branched alkyl group. It includes C1 to C6 alkyl, C1 to C4 alkyl, C1 to C3 alkyl and the like. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.
"Alkyl" of $R^1$ includes methyl, ethyl, isopropyl, tert-butyl and the like. Ethyl, isopropyl or tert-butyl is especially preferable. Furthermore, isopropyl or tert-butyl is preferable.
The "alkyl" part in "alkyloxy" is the same as the above "alkyl".
"Haloalkyl" and "haloalkyloxy" means alkyl and alkoxy wherein the "alkyl" part in "alkyl" and "alkoxy" is substituted with the 1 to 5 (preferably 1 to 3) above "halogen" at any arbitrary position(s), respectively. "Haloalkyl" means alkyl substituted with halogen(s), and is included in the substituted alkyl.
"Alkenyl" includes C2 to C10 straight or branched alkenyl having one or more double bond(s) at any possible position(s). It includes C2 to C8 alkenyl, C3 to C6 alkenyl and the like. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.
"Alkynyl" includes C2 to C10 straight or branched alkynyl having one or more triple bond(s) at any possible position(s). It includes C2 to C6 alkynyl, C2 to C4 alkynyl and the like. Examples include ethynyl, propynyl, butynyl, pentynyl, hexynyl, heptynyl, octynyl, nonynyl, decynyl and the like. Alkynyl have one or more triple bond(s) at any arbitrary position(s) and can have double bond(s).
"Cycloalkyl" means C3 to C8 cyclic saturated hydrocarbon group and the cyclic saturated hydrocarbon group fused with one or two C3 to C8 cyclic group(s). Examples of C3 to C8 cyclic saturated hydrocarbon group include cyclopropyl, cyclobutyl, cyclopentyl, cyclohexyl, cycloheptyl, cyclooctyl and the like. Especially preferable examples include C3 to C6 cycloalkyl, or C5 or C6 cycloalkyl.

The ring fused with C3 to C8 cyclic saturated hydrocarbon group includes non-aromatic hydrocarbon ring (example: cyclohexane ring, cyclopentane ring and the like), cycloalkene ring (example: cyclohexene ring, cyclopentene ring and the like) and the like), non-aromatic heterocyclic ring (example: piperidine ring, piperazine ring, morpholine ring and the like). At the above ring, the bond(s) can be attached to C3 to C8 cyclic saturated hydrocarbon group.

For example, the following groups are also exemplified as a cycloalkyl and included in cycloalkyl. These groups can be substituted at any arbitrary position(s).

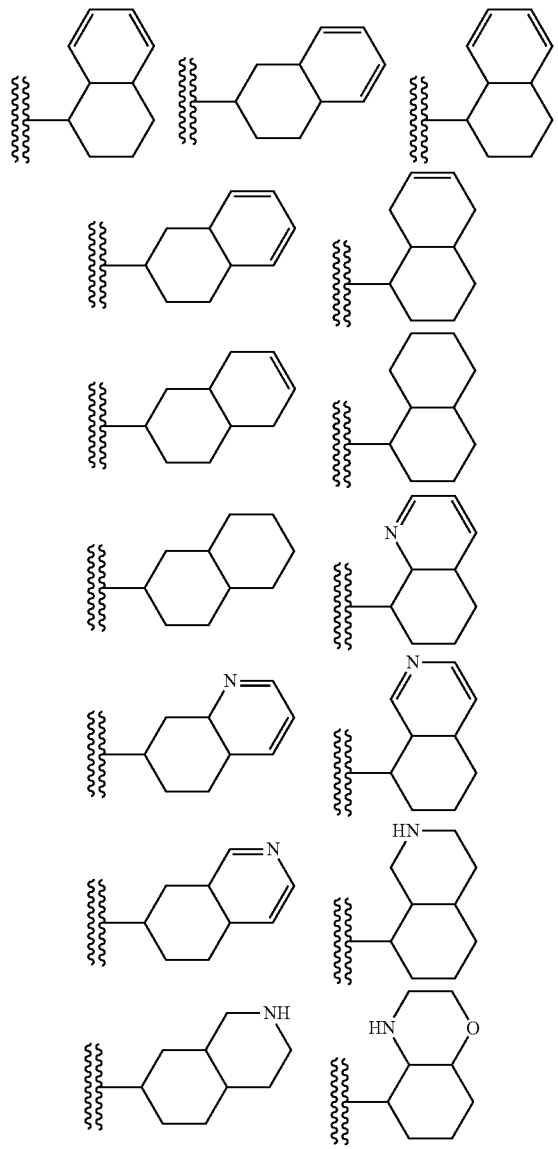

A preferable embodiment of "cycloalkyl" in $R^1$ includes cyclopropyl, cyclobutyl, cyclopentyl and the like.

A preferable embodiment of "cycloalkyl" in $R^2$ includes preferably cyclobutyl, cyclopentyl, cyclohexyl and the like.

"Cycloalkenyl" means C3 to C8 cyclic unsaturated hydrocarbon group and the cyclic unsaturated hydrocarbon group fused with one or two C3 to C8 cyclic group(s). Examples of C3 to C8 cyclic unsaturated hydrocarbon group include cyclopropenyl, cyclobutenyl, cyclopentenyl, cyclohexenyl, cycloheptenyl, cyclohexadienyl and the like. Especially preferable examples are C3 to C6 cycloalkenyl, or C5 or C6 cycloalkenyl.

The ring fused with C3 to C8 cyclic unsaturated aliphatic hydrocarbon group includes carbocyclic ring (aromatic carbocyclic ring (example: benzene ring, naphthalene ring and the like), non-aromatic carbocyclic ring (example: cycloalkane ring (example: cyclohexane ring, cyclopentane ring and the like), cycloalkene ring (example: cyclohexene ring, cyclopentene ring and the like) and the like), heterocyclic ring (aromatic heterocyclic ring (pyridine ring, pyrimidine ring, pyrrole ring, imidazole ring and the like), non-aromatic heterocyclic ring (example: piperidine ring, piperazine ring, morpholine ring and the like). At the above ring, the bond(s) can be attached to C3 to C8 cyclic unsaturated aliphatic hydrocarbon group.

For example, the following groups are also exemplified as a cycloalkenyl and included in cycloalkenyl. These groups can be substituted at any arbitrary position(s).

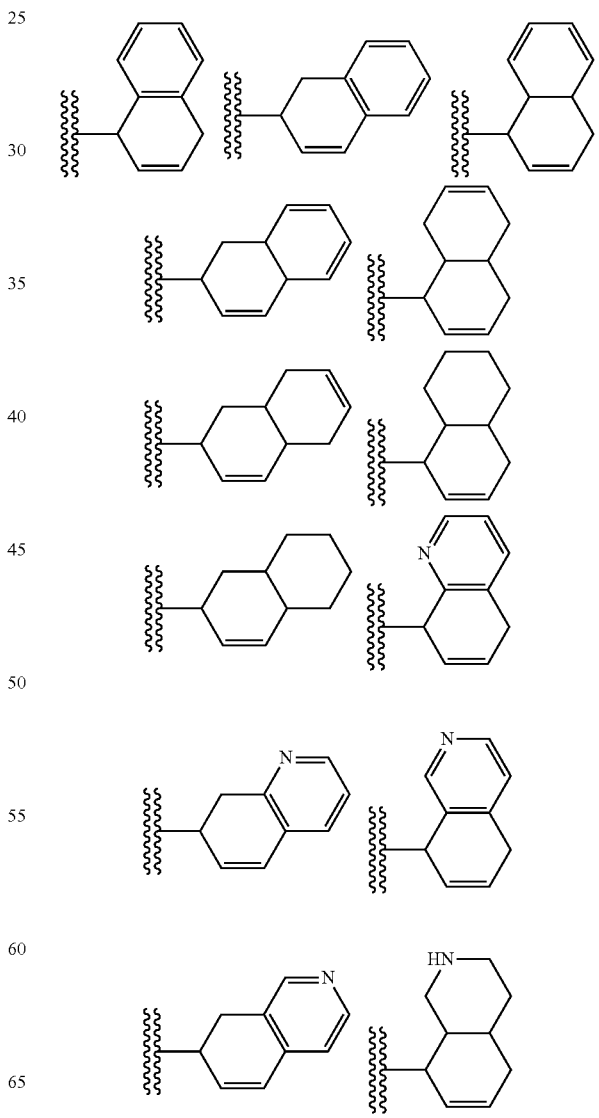

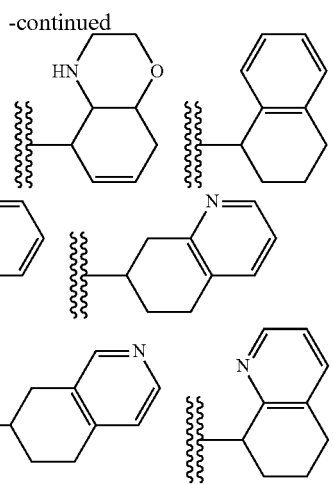

"Aryl" includes monocyclic or polycyclic aromatic carbocyclyl and monocyclic or polycyclic aromatic carbocyclyl fused with one or two 3- to 8-membered cyclic group(s). Examples of monocyclic or polycyclic aromatic carbocyclyl include phenyl, naphthyl, anthryl, phenanthryl and the like. Especially preferable example is phenyl.

The ring fused with monocyclic or polycyclic aromatic carbocyclyl group includes non-aromatic carbocyclic ring (For example, cycloalkane ring (example: cyclohexane ring, cyclopentane ring and the like), cycloalkene ring (example: cyclohexene ring, cyclopentene ring and the like) and the like), non-aromatic heterocyclic ring (For example, piperidine ring, piperazine ring, morpholine ring and the like). At the above ring, the bond(s) can be attached to monocyclic or polycyclic aromatic carbocyclyl group.

For example, the following groups are also exemplified as an aryl and included in aryl. These groups can be substituted at any arbitrary position(s).

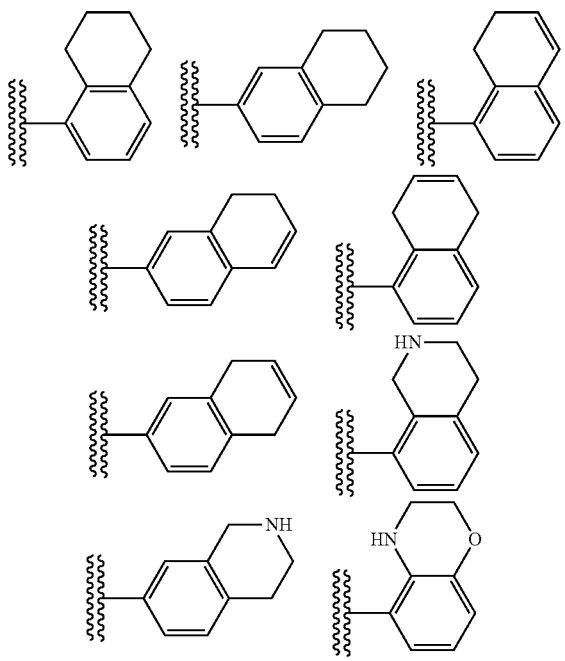

A preferable embodiment of "aryl" in $R^2$ includes phenyl and the like.

"Heteroaryl" means monocyclic or polycyclic aromatic heterocyclyl group containing one or more heteroatom(s) arbitrarily selected from O, S and N on the ring or the monocyclic or polycyclic aromatic heterocyclyl group fused with one or two 3- to 8-membered cyclic group(s).

Especially preferable examples of "monocyclic aromatic heterocyclyl" include 5- or 6-membered heteroaryl. Examples are pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like.

Especially preferable examples of "polycyclic aromatic heterocyclyl" include heteroaryl fused with 5- to 6-membered cyclic group(s).

For example, bicyclic aromatic heterocyclyl such as indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, thiazolopyridyl and the like, or tricyclic aromatic heterocyclyl such as carbazolyl, acridinyl, xanthenyl, phenothiazinyl, phenoxathinyl, phenoxazinyl, dibenzofuryl and the like are exemplified. When "heteroaryl" means "polycyclic aromatic heterocyclyl", the bond(s) can be attached to any of the rings.

The ring fused with monocyclic or polycyclic aromatic heterocyclyl group includes non-aromatic carbocyclic ring (For example, cycloalkane ring (example: cyclohexane ring, cyclopentane ring and the like), cycloalkene ring (example: cyclohexene ring, cyclopentene ring and the like) and the like), non-aromatic heterocyclic ring (For example, piperidine ring, piperazine ring, morpholine ring and the like). The bond(s) can be attached to monocyclic or polycyclic aromatic heterocyclyl group.

For example, the following groups are also exemplified as a heteroaryl and included in heteroaryl. These groups can be substituted at any arbitrary position(s).

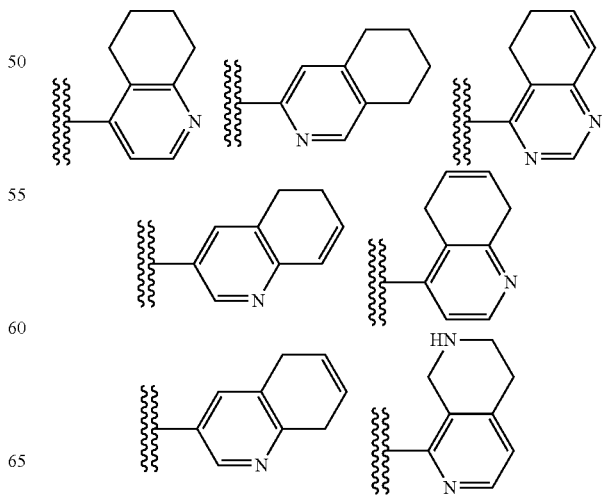

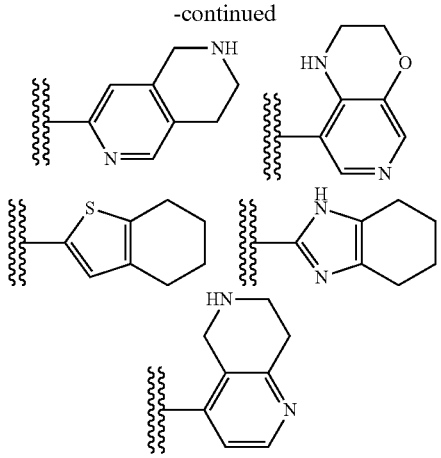

Preferable embodiments of "heteroaryl" in R² include pyridyl and the like.

Examples of a group of the formula:

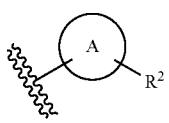

include groups of the formula:

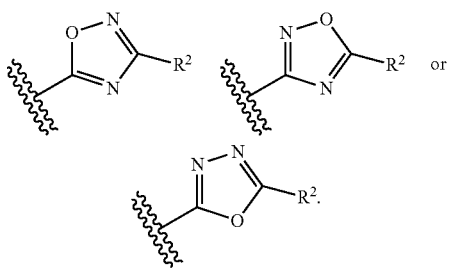

Compounds having a group of the formula:

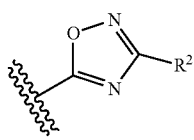

have high NPY Y5 receptor antagonistic activity and are preferable as the compounds of the invention.

"5-membered heteroaryl" means 5-membered monocyclic aromatic heterocyclyl group containing one or more heteroatom(s) arbitrarily selected from O, S and N on the ring and the group that the 5-membered monocyclic aromatic heterocyclyl group is fused with one or two 3- to 8-membered cyclic group(s).

Examples include pyrrole, imidazole, pyrazole, tetrazole, isoxazole, oxazole, oxadiazole, isothiazole, thiazole, thiadiazole, furan, thiophene and the like.

A preferable embodiment of "5-membered heteroaryl" in ring B includes oxadiazole, thiadiazole, imidazole, thiazole or oxazole and the like. The compounds having oxadiazole, oxazole and the like are especially less toxic, and are preferable as the compounds of the invention.

Especially, a preferable embodiment of the group of the formula:

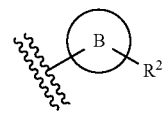

includes a group of the formula:

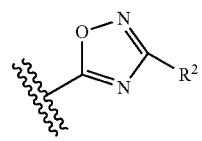

"Heterocyclyl" means a non-aromatic heterocyclyl group containing one or more heteroatom(s) arbitrarily selected from O, S and N on the ring, the non-aromatic heterocyclyl group fused with one or two 3- to 8-membered cyclic group(s). It includes monocyclic non-aromatic heterocyclyl or polycyclic non-aromatic heterocyclyl.

Examples of monocyclic non-aromatic heterocyclyl include dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperazino, morpholinyl, morpholino, oxadiazinyl, dihydropyridyl, thiomorpholinyl, thiomorpholino, tetrahydrofuryl, tetrahydropyranyl, tetrahydrothiazolyl, tetrahydroisothiazolyl, oxazolidyl, thiazolidyl and the like.

Examples of polycyclic non-aromatic heterocyclyl are specifically indolinyl, isoindolinyl, chromanyl, isochromanyl and the like.

When "non-aromatic heterocyclyl" means "polycyclic non-aromatic heterocyclyl", the bond(s) can be attached to any of the rings.

For example, the heterocyclyl includes the followings:

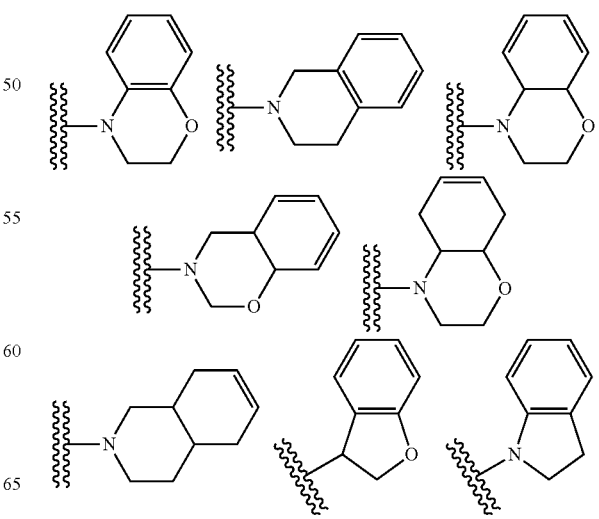

-continued

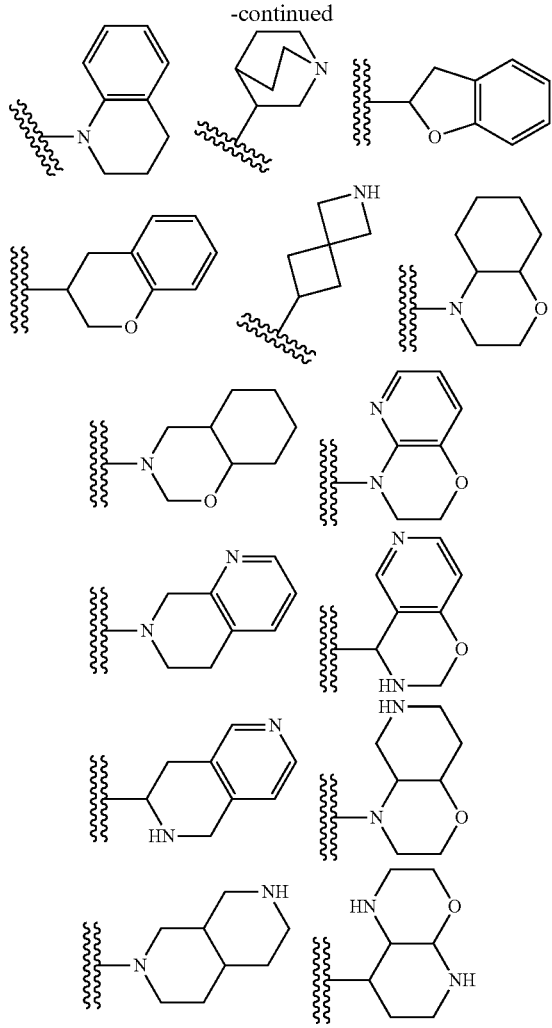

Preferable embodiments of "Heterocyclyl" in $R^2$ include tetrahydropyranyl and the like.

"Substituted or unsubstituted cycloalkyl", "substituted or unsubstituted cycloalkenyl" and "substituted or unsubstituted heterocyclyl" can be substituted with one or two oxo, thioxo or substituted or unsubstituted imino.

Examples of the substituent of "substituted alkyl", "substituted alkenyl", "substituted alkynyl", "substituted cycloalkyl", "substituted cycloalkenyl", "substituted aryl", "substituted heteroaryl" or "substituted heterocyclyl" are halogen, hydroxy, mercapto, nitro, nitroso, cyano, azide, formyl, amino, carboxy, alkyl, haloalkyl, alkenyl, alkynyl, cycloalkyl, cycloalkenyl, aryl, heteroaryl, heterocyclyl, substituted carbamoyl, substituted sulfamoyl, substituted amidino, a group of the formula: —O—$R^{10}$, a group of the formula: —O—C(=O)—$R^{10}$, a group of the formula: —C(=O)—$R^{10}$, a group of the formula: —C(=O)—O—$R^{10}$, a group of the formula: —S—$R^{10}$ or a group of the formula: —$SO_2$—$R^{10}$ (wherein $R^{10}$ is alkyl, haloalkyl, alkenyl, alkynyl, cycloalkyl, cycloalkenyl, aryl, heteroaryl, heterocyclyl, carbamoyl, sulfamoyl or amidino). "Alkyl", "alkenyl", "alkynyl", "cycloalkyl", "cycloalkenyl", "aryl", "heteroaryl" or "heterocyclyl" can be substituted at arbitrary position(s) with one or more group(s) selected from the above.

Examples of the substituent of "substituted haloalkyl" include hydroxy, mercapto, nitro, nitroso, cyano, azide, formyl, amino, carboxy, alkyl, haloalkyl, alkenyl, alkynyl, cycloalkyl, cycloalkenyl, aryl, heteroaryl, heterocyclyl, substituted carbamoyl, substituted sulfamoyl, substituted amidino, a group of the formula: —O—$R^{10}$, a group of the formula: —O—C(=O)—$R^{10}$, a group of the formula: —C(=O)—$R^{10}$, a group of the formula: —C(=O)—O—$R^{10}$, a group of the formula: —S—$R^{10}$ or a group of the formula: —$SO_2$—$R^{10}$ (wherein $R^{10}$ is alkyl, haloalkyl, alkenyl, alkynyl, cycloalkyl, cycloalkenyl, aryl, heteroaryl, heterocyclyl, carbamoyl, sulfamoyl or amidino). "Haloalkyl" can be substituted at any arbitrary position(s) with one or more group(s) selected from the above.

"Substituted or unsubstituted cycloalkyl", "substituted or unsubstituted cycloalkenyl" and "substituted or unsubstituted heterocyclyl" can be substituted with one or two oxo, thioxo or substituted or unsubstituted imino.

Examples of the substituent of "substituted aryl" and "substituted heteroaryl" in $R^2$ include halogen, alkylsulfonyl, haloalkyl, haloalkyloxy and the like.

Examples of the substituent of "substituted cycloalkyl" in $R^2$ include alkyl, alkenyl, halogen, haloalkyl, aryl and the like.

Examples of the substituent of "substituted amino", "substituted carbamoyl", "substituted sulfamoyl", "substituted amidino" or "substituted imino" include hydroxy, cyano, formyl, alkyl, haloalkyl, alkenyl, alkynyl, cycloalkyl, cycloalkenyl, aryl, heteroaryl, heterocyclyl, carbamoyl, sulfamoyl, amidino, a group of the formula: —O—R, a group of the formula: —C(=O)—R, a group of the formula: —C(=O)—O—R or a group of the formula: —$SO_2$—R (wherein R is alkyl, haloalkyl, alkenyl, alkynyl, cycloalkyl, cycloalkenyl, aryl, heteroaryl or heterocyclyl). "Amino", "carbamoyl", "sulfamoyl", "amidino" or "substituted imino" can be substituted at any arbitrary position(s) with one or more group(s) selected from the above.

$R^1$ in the compounds of the invention is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino. Preferable examples are substituted or unsubstituted alkyl or substituted or unsubstituted cycloalkyl, especially preferable example is substituted or unsubstituted alkyl.

p, q and r in the compounds of the invention are each independently 0 or 1. Preferable examples are p+q+r=1 or 2. Especially preferable example is p+q+r=1. The combination of p, q and r are preferably exemplified (p, q, r)=(0, 0, 1), (0, 1, 0), (1, 0, 0), especially preferably (p, q, r)=(1, 0, 0).

$R^2$ is substituted or unsubstituted alkyl, substituted or unsubstituted cycloalkyl, substituted or unsubstituted aryl, substituted or unsubstituted heteroaryl or substituted or unsubstituted heterocyclyl. Preferable examples are substituted or unsubstituted alkyl, substituted or unsubstituted cycloalkyl, substituted or unsubstituted aryl or substituted or unsubstituted heteroaryl. Especially preferable examples are substituted or unsubstituted alkyl or substituted or unsubstituted cycloalkyl.

Especially preferable embodiments of the compounds of the present invention are described below.

Among compounds of the formula (V):

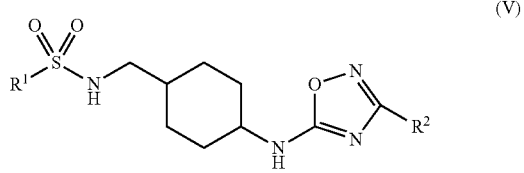

or its pharmaceutically acceptable salt, preferable are embodiments shown as the following (V-A) to (V-H).

(V-A)
The compound represented by the formula (V), or its pharmaceutically acceptable salt,
wherein $R^1$ is substituted or unsubstituted alkyl, and
$R^2$ is substituted or unsubstituted aryl or substituted or unsubstituted heteroaryl.

(V-B)
The compound represented by the formula (V), or its pharmaceutically acceptable salt,
wherein $R^1$ is substituted or unsubstituted alkyl,
$R^2$ is a group of the formula:

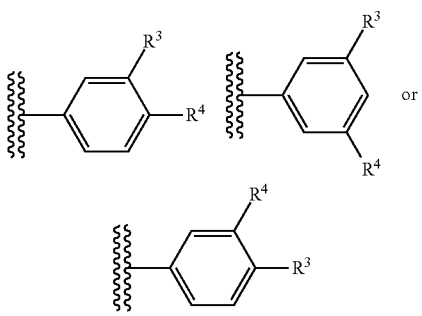

wherein
$R^3$ is halogen, alkylsulfonyl, haloalkyl or haloalkyloxy, and
$R^4$ is hydrogen, halogen, alkylsulfonyl, haloalkyl or haloalkyloxy.

(V-C)
The compound represented by the formula (V), or its pharmaceutically acceptable salt,
wherein $R^1$ is substituted or unsubstituted alkyl,
$R^2$ is a group of the formula:

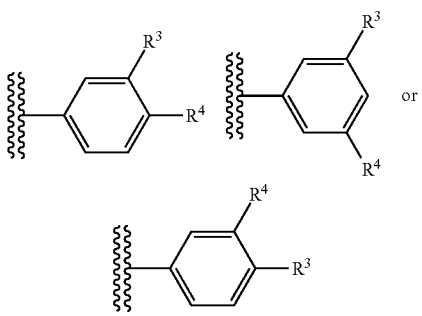

$R^3$ is halogen, alkylsulfonyl, haloalkyl or haloalkyloxy, and
$R^4$ is hydrogen, halogen, alkylsulfonyl, haloalkyl or haloalkyloxy.

(V-D)
The compound represented by the formula (V), or its pharmaceutically acceptable salt,
wherein $R^1$ is substituted or unsubstituted alkyl, and
$R^2$ is substituted or unsubstituted pyridyl.

(V-E)
The compound represented by the formula (V), or its pharmaceutically acceptable salt,
wherein $R^1$ is substituted or unsubstituted alkyl or substituted or unsubstituted cycloalkyl, and
$R^2$ is substituted or unsubstituted alkyl, substituted or unsubstituted cycloalkyl or substituted or unsubstituted heterocyclyl.

(V-F)
The compound represented by the formula (V), or its pharmaceutically acceptable salt,
wherein $R^1$ is substituted or unsubstituted alkyl, and
$R^2$ is substituted or unsubstituted alkyl, substituted or unsubstituted cycloalkyl or substituted or unsubstituted heterocyclyl.

(V-G)
The compound represented by the formula (V), or its pharmaceutically acceptable salt,
wherein $R^1$ is substituted or unsubstituted alkyl, and
$R^2$ is substituted or unsubstituted alkyl or substituted or unsubstituted cycloalkyl.

(V-H)
The compound represented by the formula (V), or its pharmaceutically acceptable salt,
wherein $R^1$ is substituted or unsubstituted alkyl, and
$R^2$ is substituted or unsubstituted haloalkyl or substituted or unsubstituted cycloalkyl.

Especially preferable embodiments of the compounds of the present invention are described below.

Among compounds of the formula (IV):

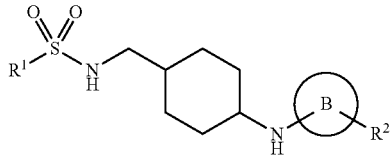

(IV)

or its pharmaceutically acceptable salt, preferable are embodiments shown as the following (IV-A) to (IV-H).

(IV-A)
The compound represented by the formula (IV), or its pharmaceutically acceptable salt,
wherein $R^1$ is substituted or unsubstituted alkyl or substituted or unsubstituted cycloalkyl,
$R^2$ is substituted or unsubstituted alkyl, substituted or unsubstituted cycloalkyl or substituted or unsubstituted heteroaryl, and
ring B is oxazole.

(IV-B)
The compound represented by the formula (IV), or its pharmaceutically acceptable salt,
wherein $R^1$ is substituted or unsubstituted alkyl,
$R^2$ is substituted or unsubstituted alkyl, substituted or unsubstituted cycloalkyl or substituted or unsubstituted heterocyclyl, and
ring B is oxazole.

(IV-C)
The compound represented by the formula (IV), or its pharmaceutically acceptable salt,
wherein $R^1$ is substituted or unsubstituted alkyl,
$R^2$ is substituted or unsubstituted alkyl or substituted or unsubstituted cycloalkyl, and
ring B is oxazole.

(IV-D)
The compound represented by the formula (IV), or its pharmaceutically acceptable salt,
wherein $R^1$ is substituted or unsubstituted alkyl,
$R^2$ is substituted or unsubstituted haloalkyl or substituted or unsubstituted cycloalkyl, and
ring B is oxazole.

(IV-E)
The compound represented by the formula (IV), or its pharmaceutically acceptable salt,
wherein R¹ is substituted or unsubstituted alkyl,
R² is substituted or unsubstituted aryl, and ring B is oxazole.

Especially preferable embodiments of the compounds of the present invention are described below.

Among compounds of the formula (I):

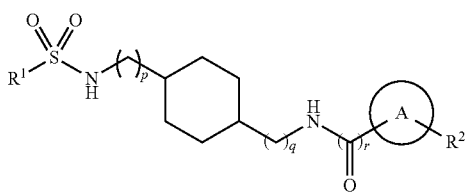
(I)

or its pharmaceutically acceptable salt, preferable are embodiments shown as the following (I-A) to (I-C).

(I-A)
The compound represented by the formula (I), or its pharmaceutically acceptable salt, wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino,
p and r are 0, q is 0,
ring A is oxadiazole, and
R² is substituted or unsubstituted alkyl or substituted or unsubstituted cycloalkyl.

(I-B)
The compound represented by the formula (I), or its pharmaceutically acceptable salt, wherein R¹ is substituted or unsubstituted alkyl or substituted or unsubstituted cycloalkyl,
R² is substituted or unsubstituted alkyl or substituted or unsubstituted cycloalkyl, and
ring A is oxadiazole.

(I-C)
The compound represented by the formula (I), or its pharmaceutically acceptable salt,
wherein R¹ is substituted or unsubstituted alkyl or substituted or unsubstituted cycloalkyl,
R² is substituted or unsubstituted alkyl or substituted or unsubstituted cycloalkyl, and
ring A is a group of the formula:

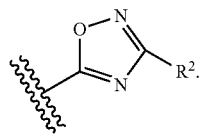

The compounds of the invention include but are not limited to all possible isomers (For example, keto-enol isomer, imine-enamine isomer, diastereo isomer, enantiomer, rotamer and the like) and racemates or mixture thereof.

One or more hydrogen, carbon and/or other atoms of the compounds of the invention can be replaced by an isotope of the hydrogen, carbon and/or other atoms. The examples of isotopes include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The compounds of the invention include compounds that substituted with the isotopes. And the compounds substituted with the isotopes are useful as medicine, and include radiolabeled forms of the compounds of the invention "radiolabeled," "radiolabeled form". The process for radiolabeling the compounds of the invention to prepare the "radiolabeled form" is encompassed by the invention, is useful as a research and/or diagnostic tool in metabolism pharmacokinetic studies and in binding assays.

Radiolabeled compounds of the invention can be prepared by methods known in the art. For example, tritiated compounds of formula (I) and (IV) can be prepared by introducing tritium into the particular compound of formula (I) and (IV), for example, by catalytic dehalogenation with tritium. This method may include reacting a suitably halogen-substituted precursor of the compound of formula (I) with tritium gas in the presence of a suitable catalyst such as Pd/C, in the presence or absence of a base. Other suitable methods for preparing tritiated compounds can be found in Filer, "The Preparation and Characterization of Tritiated Neurochemicals," Chapter 6, pp. 155-192 in Isotopes in the Physical and Biomedical Sciences, Vol. 1, Labeled Compounds (Part A) (1987). $^{14}C$-labeled compounds can be prepared by employing starting materials having a $^{14}C$ carbon.

Examples of "pharmaceutically acceptable salts" include salt such as the compound of the formula (I) and (IV) with alkaline metals (e.g. lithium, sodium, potassium and the like), alkaline earth metals (e.g. calcium, barium and the like), magnesium, transition metals (e.g. zinc, iron and the like), ammonium, organic bases (e.g. trimethylamine, triethylamine, dicyclohexylamine, ethanolamine, diethanolamine, triethanolamine, meglumine, ethylenediamine, pyridine, picoline, quinoline and the like) and amino acids, and salts with inorganic acids (e.g. hydrochloric acid, sulfuric acid, nitric acid, carbonic acid, hydrobromic acid, phosphoric acid, hydroiodic acid and the like), and organic acids (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid and the like). Specifically preferable examples are hydrochloric acid, sulfuric acid, phosphoric acid, tartaric acid, methanesulfonic acid and the like. These salts may be formed by a routine method.

The compounds of the invention or its pharmaceutically acceptable salts can be prepared in a form of solvate (For example, hydrate) thereof and its crystal polymorph, the present invention includes such solvate and polymorph. Any number of solvent molecules can be coordinated to form such solvate to the compounds of the invention. When the compounds of the invention or its pharmaceutically acceptable salt are left in the atmosphere, it can absorb moisture to attach the absorbed water or to form the hydrate. Also, the compounds of the invention or its pharmaceutically acceptable salt can be recrystallized to form the crystal polymorph.

The compounds of the invention or its pharmaceutically acceptable salts can be formed the prodrug, the present invention includes the various prodrug. The prodrug is the derivatives of the compounds of the invention having the group decomposed by chemical or metabolic method, and are compounds that prepared by solvolysis or under condition, and are compounds having an activity in vivo. The prodrug includes compounds converted to the compounds of the invention by oxidation, reduction or hydrolysis under physiological conditions in vivo and compounds hydrolyzed to the compounds of the invention by gastric acid and the like.

Conventional procedures for the selection and preparation of suitable prodrug derivatives are described, for example, in Design of Prodrugs (ed. H. Bundgaard, Elsevier, 1985). The prodrug sometimes has NPY Y5 receptor antagonistic activity.

When the compounds of the invention or its pharmaceutically acceptable salt has hydroxy, for example, it is reacted with the suitable acyl halide, the suitable acid anhydride, the suitable sulfonyl chloride, the suitable sulfonyl anhydride and mixed anhydride or with condensation agent to afford the prodrug such as the acyloxy derivatives or sulfonyoxy derivatives. Examples of the prodrug are $CH_3COO-$、$C_2H_5COO-$、$t-BuCOO-$、$C_{15}H_{31}COO-$、$PhCOO-$、$(m-NaOOCPh)COO-$、$NaOOCCH_2CH_2COO-$、$CH_3CH(NH_2)COO-$、$CH_2N(CH_3)_2COO-$、$CH_3SO_3-$、$CH_3CH_2SO_3-$、$CF_3SO_3-$、$CH_2FSO_3-$、$CF_3CH_2SO_3-$、$p-CH_3-O-PhSO_3-$、$PhSO_3-$、$p-CH_3PhSO_3-$.

The general procedures for the compounds of the invention are described below. The procedures for the compounds of the invention are not limited to the general procedures described below. The compounds of the invention can be prepared by the knowledge of organic chemistry methods known in the art.

Methods for the preparation of the compound of the formula (I):

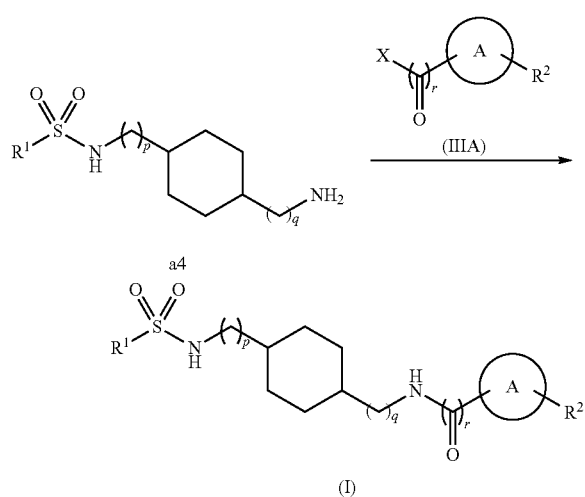

wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p, q and r are each independently 0 or 1, ring A is oxadiazole, $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and X is halogen or trihalogenomethyl.

The compound of the formula (I) can be prepared by reacting a solution of Compound a4 with a compound of the formula (IIIA) in the presence of a base.

Compound a4 can be prepared according to the method described in Patent Document 8 (WO2009/54434).

Examples of the reaction solvent include DMF, NMP, methylene chloride, ethanol and the like.

Examples of the base include DIEA, triethylamine, pyridine, potassium carbonate and the like, the amount of the base is 1 to 5 equivalent(s), and preferably 2 to 3 equivalents to Compound a4.

The temperature for such reaction may be about $-20°$ C. to $50°$ C., or $0°$ C. to room temperature.

Reaction may be conducted for 0.1 to 5 hours.

(1) Methods for the preparation of a compound of the formula (III):

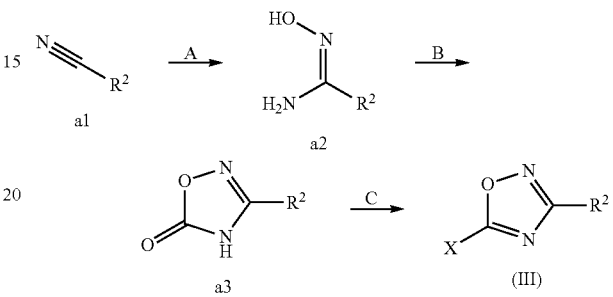

wherein $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and X is halogen.

Step A

Compound a2 can be prepared by reacting Compound a1 with hydroxyamine or its hydrochloride.

The amount of the hydroxyamine or its hydrochloride is 1 to 5 equivalent(s) to Compound a1.

Examples of the reaction solvent include methanol, ethanol, 2-propanol and the like.

Examples of the base include sodium hydroxide, potassium hydroxide, potassium carbonate, cesium carbonate and the like, and the amount of the base is 1 to 5 equivalent(s) to Compound a1.

The temperature for such reaction may be $-20°$ C. to $60°$ C. and preferably $0°$ C. to room temperature.

Reaction may be conducted for 0.1 to 24 hours and preferably for 1 to 12 hour(s).

Step B

Compound a3 may be prepared by reacting Compound a2 with cyclizing reagent in the presence of a base.

Examples of the cyclizing reagent include triphosgene, carbonyldiimidazole, ethyl chloroformate, diethyl carbonate and the like, the amount of the cyclizing reagent is 0.1 to 2 equivalents, and preferably 0.2 to 1.2 equivalents to Compound a2.

Examples of the base include DIEA, triethylamine, pyridine and the like, the amount of the base is 1 to 5 equivalent(s), and preferably 1.5 to 3 equivalents to Compound a2.

Examples of the reaction solvent include THF, DMF, DMA and the like.

The temperature for such reaction may be $50°$ C. to heat refluxing, and preferably heat refluxing.

Reaction may be conducted for 0.5 to 5 hours, preferably 1 to 3 hour(s).

Step C

The compound of the formula (III) can be prepared by reacting Compound a3 with halogenating reagent in the presence of a base.

Examples of the base include pyridine, triethylamine, DIEA and the like, the amount of the base is 1 to 3 equivalent(s) and preferably 1 to 1.5 equivalent(s) to Compound a3.

Examples of the halogenating reagent include phosphoryl chloride, phosphorous pentachloride and the like, the amount of the halogenating reagent is 5 to 30 equivalents and preferably 10 to 20 equivalents to Compound a3.

The temperature for such reaction may be 50° C. to 150° C., preferably 100° C. to 150° C.

Reaction may be conducted for 0.5 to 5 hours, and preferably 1 to 3 hour(s).

(2) Methods for the preparation of the compound of the formula (III):

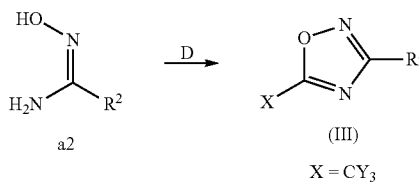

wherein $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, X is $CY_3$, and Y is halogen.

Step D

The compound of the formula (III) may be prepared by reacting Compound a2 with cyclizing reagent in the presence of a base.

Examples of the base include pyridine, triethylamine, DIEA and the like, the amount of the base is 1 to 3 equivalent(s), and preferably 1 to 1.5 equivalent(s) to Compound a2.

Examples of the cyclizing reagent include trihalogenoacetic anhydride (For example, trichloroacetic anhydride and the like), the amount of the cyclizing reagent is 5 to 30 equivalents, and preferably 10 to 20 equivalents to Compound a2.

The temperature for such reaction may be 50° C. to 150° C., and preferably 100° C. to 150° C.

Reaction may be conducted for 0.5 to 5 hours, and preferably 1 to 3 hour(s).

The compound of the formula (III) described above is a useful compound as intermediates for the compound of the formula (I). $R^2$ is preferably substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl. Especially preferable examples in $R^2$ are substituted or unsubstituted haloalkyl, substituted or unsubstituted cycloalkyl, substituted or unsubstituted aryl, substituted or unsubstituted heteroaryl or substituted or unsubstituted heterocyclyl. Furthermore, $R^2$ are preferably substituted or unsubstituted haloalkyl or substituted or unsubstituted cycloalkyl. When $R^2$ is substituted aryl, $R^2$ is preferably a group of the formula:

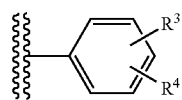

wherein $R^3$ is halogen, alkylsulfonyl, haloalkyl or haloalkyloxy, and $R^4$ is hydrogen, halogen, alkylsulfonyl, haloalkyl or haloalkyloxy.

Methods for the preparation of a compound of the formula (I'):

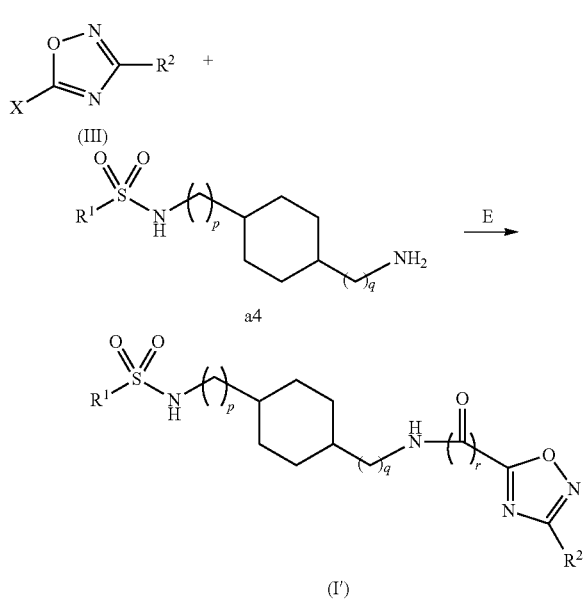

wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted or unsubstituted amino, p, q and r are each independently 0 or 1, $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and X is halogen or trihalogenomethyl.

Step E

The compound of the formula (I') can be prepared by reacting a solution of Compound a4 with a compound of the formula (III) in the presence of a base.

Compound a4 can be prepared according to the method described in Patent Document 8 (WO2009/54434).

Examples of the reaction solvent include DMF, NMP, methylene chloride, ethanol and the like.

Examples of the base include DIEA, triethylamine, pyridine, potassium carbonate and the like, the amount of the base is 1 to 5 equivalent(s), and preferably 2 to 3 equivalents to Compound a4.

The temperature for such reaction may be about −20° C. to 50° C., or 0° C. to room temperature.

Reaction may be conducted for 0.1 to 5 hours.

A compound of the formula (I') wherein r is 1 can be synthesized by using a compound of the formula (III) wherein X is trihalogenomethyl.

A compound of the formula (I') wherein r is 0 can be synthesized by using a compound of the formula (III) wherein X is halogen.

Methods for the preparation of a compound of the formula (I'''):

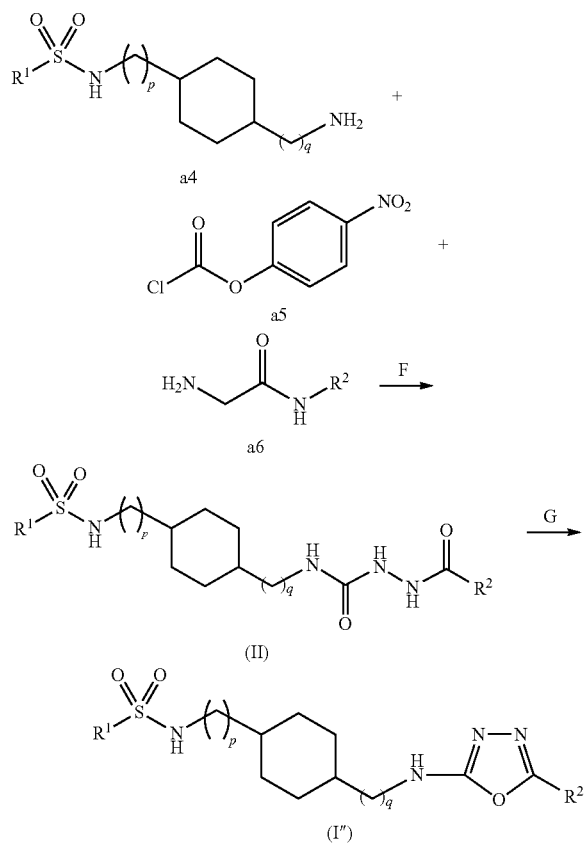

wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p, q and r are each independently 0 or 1, and R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

Step F

The compound of the formula (II) can be prepared by reacting a dichloromethane solution of Compound a4 with Compound a5 in the presence of a base A, and reacting the above mixture with base B and a solution of Compound a6.

Examples of the reaction solvent include acetonitrile, THF, DMF, NMP, DMA, and the like.

Examples of the base A include pyridine, triethylamine, DIEA. The amount of the base A can be 0.1 to 1 equivalent(s), and preferably 0.1 to 0.3 equivalents to Compound a4.

Examples of the base B include triethylamine, DIEA, pyridine, potassium carbonate and the like. The amount of the base B can be 1.5 to 3 equivalents to Compound a4.

The temperature for such reaction may be 0° C. to 50° C., and preferably 0° C. to room temperature.

Reaction may be conducted for 1 to 24 hour(s).

Step G

The compound of the formula (I'') can be prepared by reacting a dichloromethane solution of the compound of the formula (II) with triphenylphosphine and carbon tetrachloride in the presence of a base. The compound of the formula (I'') can be also prepared by reacting a dichloromethane solution of the compound of the formula (II) with Martin Sulfurane, Burgess reagent, para toluenesulfonic acid or phosphoryl chloride.

Examples of the reaction solvent include acetonitrile, THF, DMF, NMP, DMA, and the like.

Examples of the base include triethylamine, DIEA, pyridine and the like, and the amount of the base can be 1 to 10 equivalent(s) to Compound a4.

The temperature for such reaction may be 0° C. to 50° C., preferably 0° C. to room temperature.

Reaction may be conducted for 1 to 24 hour(s).

The compounds of the formula (II) described above are useful as intermediates for the compounds of the formula (I). R² is preferably substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl. Especially preferable examples in R² are substituted or substituted cycloalkyl, substituted or unsubstituted aryl, substituted or unsubstituted heteroaryl or substituted or unsubstituted heterocyclyl. When R² is substituted aryl, R² is preferably a group of the formula:

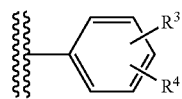

wherein R³ is halogen, alkylsulfonyl, haloalkyl or haloalkyloxy, and

R⁴ is hydrogen, halogen, alkylsulfonyl, haloalkyl or haloalkyloxy.

Methods for the preparation of Compound a8:

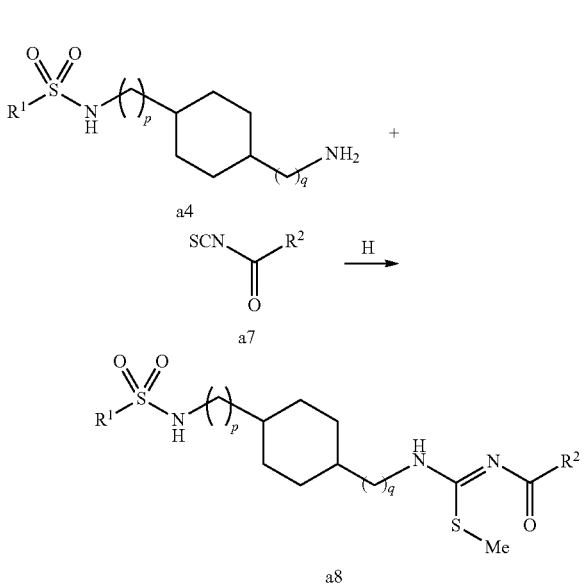

wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p and q are each independently 0 or 1, and R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

Step H

Compound a8 can be prepared by reacting Compound a4 with Compound a7, and reacting the mixture with iodomethane and a base.

Examples of the reaction solvent include methylene chloride, tetrahydrofuran and the like.

The amount of Compound a7 can be 0.7 to 1 equivalents to Compound a4.

The amount of the iodomethane can be 1 to 1.5 equivalent(s) to Compound a4.

Examples of the base include sodium hydroxide, potassium carbonate, cesium carbonate and the like, and the amount of the base can be 1 to 5 equivalent(s) to Compound a4.

The temperature for such reaction may be 0° C. to 50° C. and preferably 0° C. to room temperature.

Reaction may be conducted for 0.1 to 5 hours and preferably 0.2 to 1 hour(s).

Methods for the preparation of a compound of the formula (I'''):

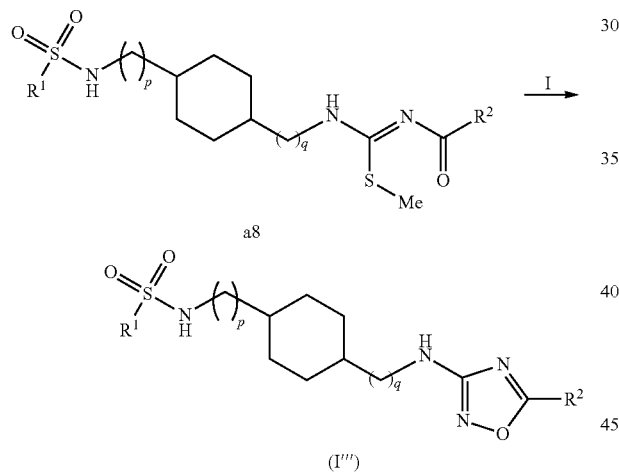

wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p and q are each independently 0 or 1, and R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

Step I

The compound of the formula (I''') can be prepared by reacting with hydroxyamine with Compound a8.

Examples of the reaction solvent include ethanol, methanol, acetonitrile and the like.

The amount of the hydroxyamine can be 10 to 100 equivalents, and preferably 50 to 75 equivalents to Compound a8.

The temperature for such reaction may be about 50° C. to heat refluxing, and preferably heat refluxing.

Reaction may be conducted for 1 to 12 hour(s), and preferably for 2 to 5 hours.

The compounds of the invention can be prepared by the reaction described below, as well as the reaction described above.

For example, the compounds of the present invention wherein r is 1 can be prepared by reacting Compound a4 with the acid chloride of oxadiazole of the following formula:

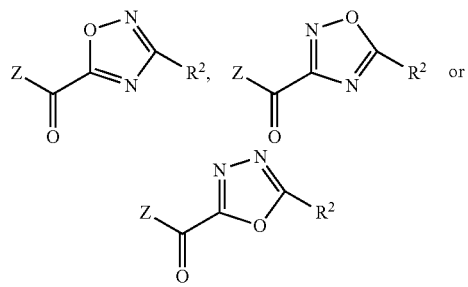

wherein R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and Z is halogen.

Methods for the preparation of Compound a10:

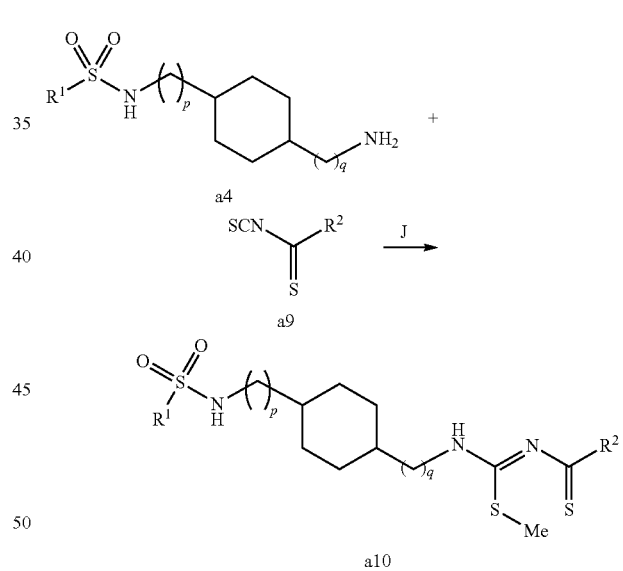

wherein R¹ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p and q are each independently 0 or 1, and R² is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

Step J

Compound a10 can be prepared by reacting Compound a4 with Compound a9, and reacting the mixture with iodomethane and a base.

Examples of the reaction solvent include methylene chloride, tetrahydrofuran and the like.

The amount of Compound a9 can be 0.7 to 1 equivalent(s) to Compound a4.

The amount of the iodomethane can be 1 to 1.5 equivalent(s) to Compound a4.

Examples of the base include sodium hydroxide, potassium carbonate, cesium carbonate and the like, and the amount of the base can be 1 to 5 equivalent(s) to Compound a4.

The temperature for such reaction may be 0° C. to 50° C., and preferably 0° C. to room temperature.

Reaction may be conducted for 0.1 to 1.5 hours, and preferably for 0.2 to 1 hour(s).

Methods for the preparation of a compound of the formula (I''''):

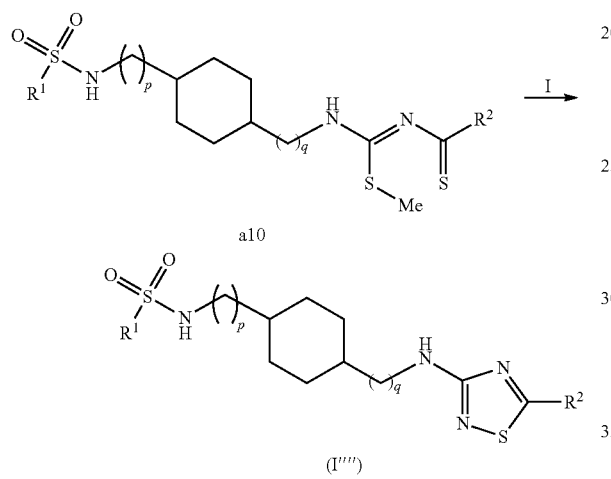

wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, p and q are each independently 0 or 1, and $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

Step I

The compound of the formula (I'''') can be prepared by reacting Compound a10 with hydroxythioamine.

Examples of the reaction solvent include ethanol, methanol, acetonitrile and the like.

The amount of the hydroxythioamine can be 10 to 100 equivalents, and preferably 50 to 75 equivalents to Compound a8.

The temperature for such reaction may be about 50° C. to heat refluxing, and preferably heat refluxing.

Reaction may be conducted for 1 to 12 hour(s), and preferably for 2 to 5 hours.

The compounds of the invention can be prepared by the reaction described below, as well as the reaction described above.

For example, the compounds of the invention wherein r is 1 can be prepared by reacting Compound a4 with the acid chloride of thiadiazole of the following formula:

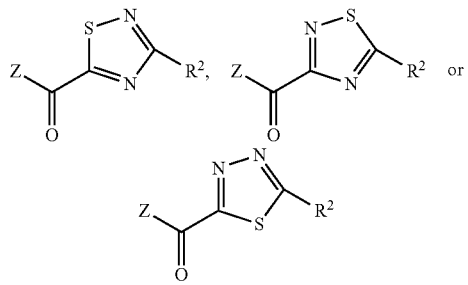

wherein $R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl, and Z is halogen.

Methods for the preparation of a compound of the formula (IV):

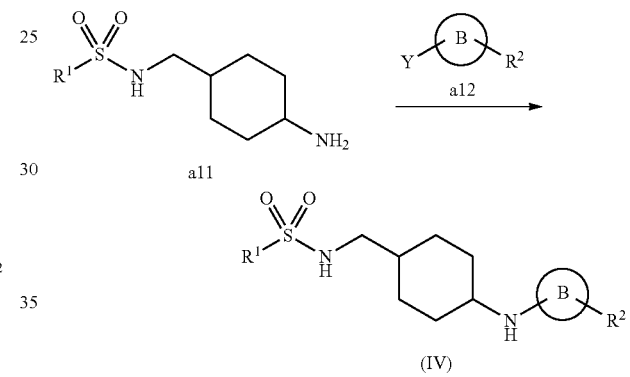

wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino, ring B is 5-membered aromatic heterocycle, $R^2$ is substituted or unsubstituted haloalkyl, substituted or unsubstituted cycloalkyl, substituted or unsubstituted cycloalkenyl or substituted or unsubstituted heterocyclyl, and Y is leaving group (halogen etc.).

The compound of the formula (IV) can be prepared by reacting a solution of Compound a11 with Compound a12 in the presence of a base.

Compound a11 can be prepared according to the method described in Patent Document 8 (WO2009/54434).

Examples of the reaction solvent include DMF, NMP, dichloromethane, ethanol and the like.

Examples of the base include DIEA, triethylamine, pyridine, potassium carbonate and the like, the amount of the base can be 1 to 5 equivalent(s), and preferably 2 to 3 equivalents to Compound a11.

The temperature for such reaction may be about −20° C. to 50° C., or 0° C. to room temperature.

Reaction may be conducted for 0.1 to 5 hours.

The compounds of the invention afforded in this way can be purified by recrystallization with various solvents. Examples of solvents are alcohol (methanol, ethanol, isopropylalcohol, n-butanol and the like), ether (diethylether, diisopropylether and the like), methyl acetate, ethyl acetate, chloroform, methylene chloride, tetrahydrofuran, N,N-dimethylformamide, toluene, benzene, xylene, acetonitrile, hexane, dioxane, dimethoxyethane, water, or the mixture solvent thereof. The compounds of the invention are dissolved in these solvents on heating, then the impurities are removed. The solution is gradually cooled, the deposited solids or crystals can be filtered to afford the compounds of the invention.

The compound of the invention is very useful as a medicine especially for preventing or treating a disease associated with NPY Y5, e.g. feeding disorder, obesity, hyperorexia, sexual disorder, impaired fertility, depression, epileptic seizure, hypertension, cerebral hemorrhage, congestive heart failure or sleep disorders. Moreover, the antagonist is effective for preventing or treating the diseases in which obesity acts as a risk factor, for example, diabetes, hypertension, hyperlipemia, atherosclerosis and acute coronary syndrome. Especially it is useful to the prevention and/or treatment of obesity, or the weight management for obesity. Moreover, the antagonist is effective for preventing or treating the diseases in which obesity acts as a risk factor, for example, diabetes, hypertension, hyperlipemia, atherosclerosis and acute coronary syndrome.

Furthermore, a compound of this invention has not only NPY Y5 receptor antagonistic activity but also usefulness as a medicine and any or all good characters selected from the followings.
a) weak CYP (e.g., CYP1A2, CYP2C9, CYP3A4 and the like) enzyme inhibition.
b) good drug disposition such as high bioavailability, appropriate clearance and the like.
c) low toxicity of anemia-inducing activity or the like.
d) high metabolic stability.
e) high water solubility.
f) high transportability through the blood-brain barrier.
g) no gastrointestinal injury such as hemorrhagic enteritis, gastrointestinal tract ulcer, gastrointestinal bleeding and the like.

In addition, the compound of the invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the NPY Y5 receptor antagonist has a low risk of inducing side effects based on the peripheral vasoconstriction, and a pharmaceutical composition comprising the compound of this invention as an active ingredient is able to be suitably used as a safe medicine.

The pharmaceutical composition comprising the compound of the invention shows an anti-obesity effect by suppressing food intake. Therefore, it is one of the features of the pharmaceutical composition not to induce side effects such as dyspepsia caused by an anti-obesity agent which inhibits digestion and absorption, or central nervous system side-effects such as an antidepressant effect due to a serotonin transporter inhibitor that shows an anti-obesity effect.

The pharmaceutical composition of the invention can be administered orally or parenterally as an anti-obesity agent or anorectic agent. In the case of oral administration, it may be in any usual form such as tablets, granules, powders, capsules, pills, solutions, syrups, buccal tablets, sublingual tablets and the like. When the compound is parenterally administered, any usual form is preferable, for example, injections (e.g., intravenous, intramuscular), suppositories, endermic agents, inhalations and the like. Oral administration is especially preferable because the compounds of this invention show a high oral absorbability.

The pharmaceutical composition may be manufactured by mixing an effective amount of the compound of the invention with various pharmaceutical additives suitable for the administration form, such as excipients, binders, moistening agents, disintegrants, lubricants, diluents and the like. When the composition is of an injection, an active ingredient together with a suitable carrier can be sterilized to give a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate, macrogol and the like. Cacao oil, macrogol, methylcellulose or the like may be used as base materials of suppositories. When the composition is manufactured as solutions, emulsified injections or suspended injections, solubilizing agent, suspending agents, emulsifiers, stabilizers, preservatives, isotonic agents and the like which are usually used may be added. For oral administration, sweetening agents, flavors and the like which are usually used may be added.

Although the dosage of the pharmaceutical composition of the invention as an anti-obesity agent or anorectic agent should be determined in consideration of the patient's age and body weight, the type and degree of diseases, the administration route and the like, a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

The pharmaceutical composition of the present invention can be used in combination with other anti-obesity agent(s) (the pharmaceutical composition comprising compounds having anti-obesity effect, or the medicinal agent for obesity or for the weight management for obesity). For example, a combination treatment with a pharmaceutical composition comprising a compound having an anti-obesity effect and the compounds of the invention can be used for the prevention or treatment of obesity and/or the weight management for obesity.

A combination treatment with the pharmaceutical composition comprising the compounds of the invention and a pharmaceutical composition(s) comprising a compound having an anti-obesity effect can be used for the prevention or treatment of obesity and/or the weight management for obesity.

Furthermore, a method of treatment by administering the pharmaceutical composition of the invention can be used in combination of the dietary therapy, drug therapy, exercise and the like.

The present invention includes the following method.

A method for the prevention or treatment of obesity or an obesity-related disorder, or the weight management for obesity, characterized by administering a pharmaceutical composition comprising the compound of the invention or its pharmaceutically acceptable salt and another compound having an anti-obesity effect.

A method for the prevention or treatment of obesity or an obesity-related disorder, or the weight management for obesity, characterized by administering the pharmaceutical composition comprising compound having another anti-obesity effect to the patient receiving the prevention or treatment with administering the present compound or its pharmaceutically acceptable salt.

Embodiments of the compound of the invention include compounds represented by the general formula (VI):

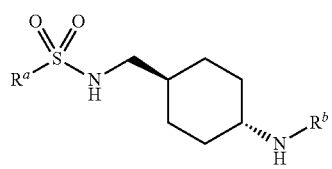
(VI)

TABLE 1

| $R^a$ | |
|---|---|
| $R^{a1}$ | Me |
| $R^{a2}$ | Et |
| $R^{a3}$ | i-Pr |
| $R^{a4}$ | t-Bu |
| $R^{a5}$ | i-Bu |
| $R^{a6}$ | cyclopropyl |

In the above Table, Me indicates methyl, Et indicates ethyl, i-Pr indicates isopropyl, t-Bu indicates tert-butyl, cyclopropyl indicates cyclopropyl.

| ($R^b$) |
|---|
| 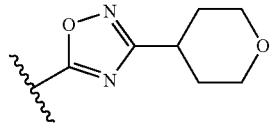 [SMILES: *c1nc(C2CCOCC2)no1] ($R^{b1}$) |
| 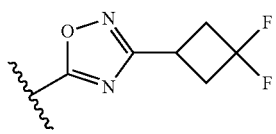 [SMILES: *c1nc(C2CC(F)(F)C2)no1] ($R^{b2}$) |
| 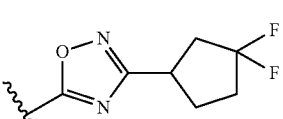 ($R^{b3}$) |
| 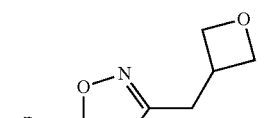 ($R^{b4}$) |
| 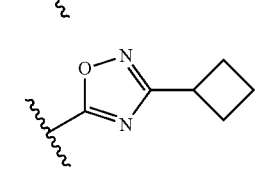 ($R^{b5}$) |

-continued

| ($R^b$) |
|---|
| 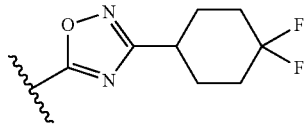 [SMILES: *c1nc(C2CCC(F)(F)CC2)no1] ($R^{b6}$) |
| 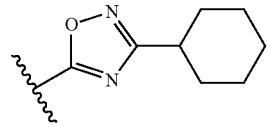 [SMILES: *c1nc(C2CCCCC2)no1] ($R^{b7}$) |
| 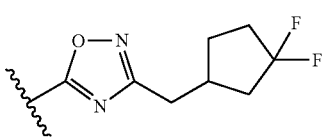 [SMILES: *c1nc(CC2CCC(F)(F)C2)no1] ($R^{b8}$) |
| 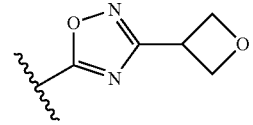 [SMILES: *c1nc(C2COC2)no1] ($R^{b9}$) |
| 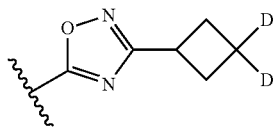 [SMILES: *c1nc(C2CC([2H])([2H])C2)no1] ($R^{b10}$) |
| 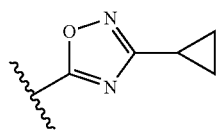 [SMILES: *c1nc(C2CC2)no1] ($R^{b11}$) |
| 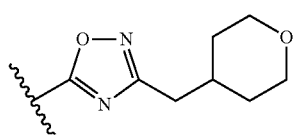 [SMILES: *c1nc(CC2CCOCC2)no1] ($R^{b12}$) |
| 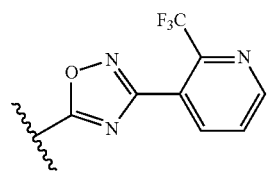 [SMILES: *c1nc(-c2cccnc2C(F)(F)F)no1] ($R^{b13}$) |
| 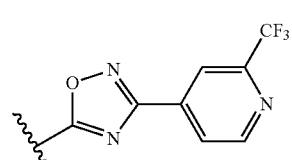 ($R^{b14}$) |
| 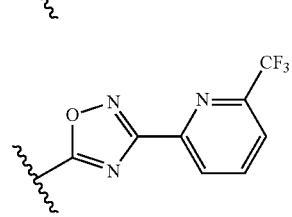 ($R^{b15}$) |

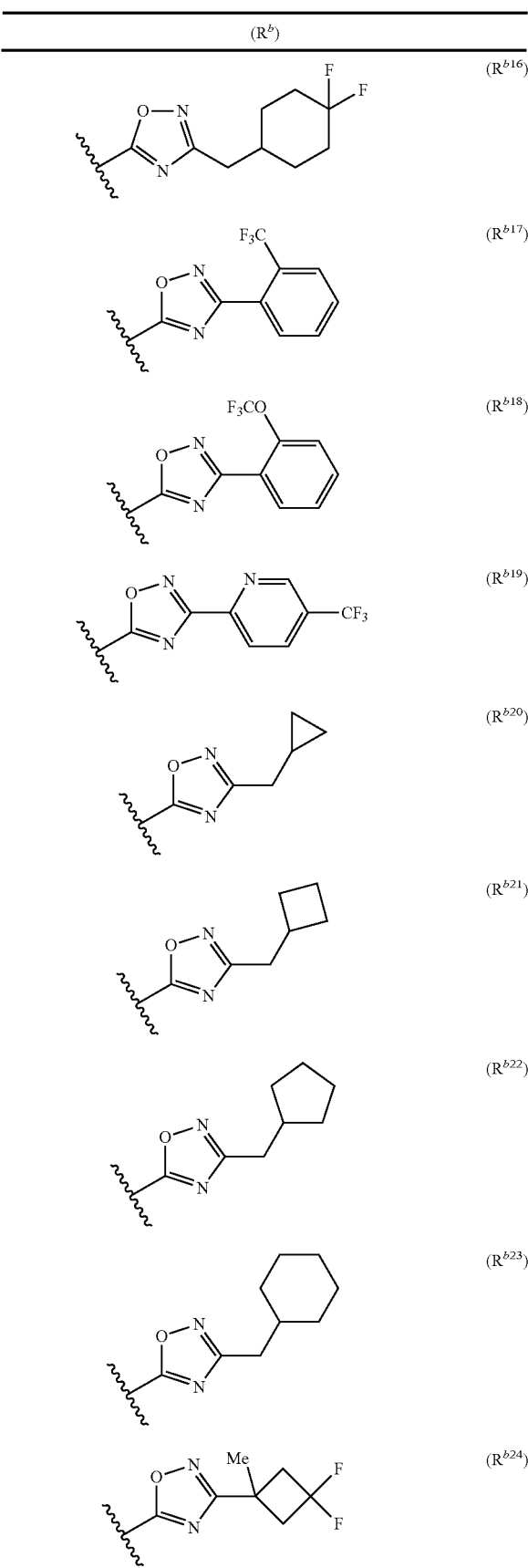
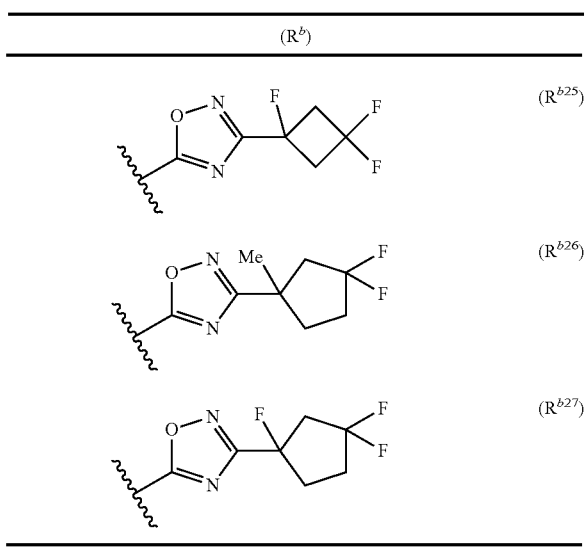

The compounds represented by the following ($R^a$, $R^b$) which shows the combination of $R^a$ and $R^b$ are exemplified: ($R^a$, $R^b$)=($R^{a1}$, $R^{b1}$), ($R^{a1}$, $R^{b2}$), ($R^{a1}$, $R^{b3}$), ($R^{a1}$, $R^{b4}$), ($R^{a1}$, $R^{b5}$), ($R^{a1}$, $R^{b6}$), ($R^{a1}$, $R^{b7}$), ($R^{a1}$, $R^{b8}$), ($R^{a1}$, $R^{b9}$), ($R^{a1}$, $R^{b10}$), ($R^{a1}$, $R^{b11}$), ($R^{a1}$, $R^{b12}$), ($R^{a1}$, $R^{b13}$), ($R^{a1}$, $R^{b14}$), ($R^{a1}$, $R^{b15}$), ($R^{a1}$, $R^{b16}$), ($R^{a1}$, $R^{b17}$), ($R^{a1}$, $R^{b18}$), ($R^{a1}$, $R^{b19}$), ($R^{a1}$, $R^{b20}$), ($R^{a1}$, $R^{b21}$), ($R^{a1}$, $R^{b22}$), ($R^{a1}$, $R^{b23}$), ($R^{a1}$, $R^{b24}$), ($R^{a1}$, $R^{b25}$), ($R^{a1}$, $R^{b26}$), ($R^{a1}$, $R^{b27}$), ($R^{a2}$, $R^{b1}$),($R^{a2}$, $R^{b2}$), ($R^{a2}$, $R^{b3}$), ($R^{a2}$, $R^{b4}$), ($R^{a2}$, $R^{b5}$), ($R^{a2}$, $R^{b6}$), ($R^{a2}$, $R^{b7}$), ($R^{a2}$, $R^{b8}$), ($R^{a2}$, $R^{b9}$), ($R^{a2}$, $R^{b10}$), ($R^{a2}$, $R^{b11}$), ($R^{a2}$, $R^{b12}$), ($R^{a2}$, $R^{b13}$), ($R^{a2}$, $R^{b14}$), ($R^{a2}$, $R^{b15}$), ($R^{a2}$, $R^{b16}$), ($R^{a2}$, $R^{b17}$), ($R^{a2}$, $R^{b18}$), ($R^{a2}$, $R^{b19}$), ($R^{a2}$, $R^{b20}$), ($R^{a2}$, $R^{b21}$), ($R^{a2}$, $R^{b22}$), ($R^{a2}$, $R^{b23}$), ($R^{a2}$, $R^{b24}$), ($R^{a2}$, $R^{b25}$), ($R^{a2}$, $R^{b26}$), ($R^{a2}$, $R^{b27}$), ($R^{a3}$, $R^{b1}$), ($R^{a3}$, $R^{b2}$), ($R^{a3}$, $R^{b3}$), ($R^{a3}$, $R^{b4}$), ($R^{a3}$, $R^{b5}$), ($R^{a3}$, $R^{b6}$), ($R^{a3}$, $R^{b7}$), ($R^{a3}$, $R^{b8}$), ($R^{a3}$, $R^{b9}$), ($R^{a3}$, $R^{b10}$), ($R^{a3}$, $R^{b11}$), ($R^{a3}$, $R^{b12}$), ($R^{a3}$, $R^{b13}$), ($R^{a3}$, $R^{b14}$), ($R^{a3}$, $R^{b15}$), ($R^{a3}$, $R^{b16}$), ($R^{a3}$, $R^{b17}$), ($R^{a3}$, $R^{b18}$), ($R^{a3}$, $R^{b19}$), ($R^{a3}$, $R^{b20}$), ($R^{a3}$, $R^{b21}$), ($R^{a3}$, $R^{b22}$), ($R^{a3}$, $R^{b23}$), ($R^{a3}$, $R^{b24}$), ($R^{a3}$, $R^{b25}$), ($R^{a3}$, $R^{b26}$), ($R^{a3}$, $R^{b27}$), ($R^{a4}$, $R^{b1}$), ($R^{a4}$, $R^{b2}$), ($R^{a4}$, $R^{b3}$), ($R^{a4}$, $R^{b4}$), ($R^{a4}$, $R^{b5}$), ($R^{a4}$, $R^{b6}$), ($R^{a4}$, $R^{b7}$), ($R^{a4}$, $R^{b8}$), ($R^{a4}$, $R^{b9}$), ($R^{a4}$, $R^{b10}$), ($R^{a4}$, $R^{b11}$), ($R^{a4}$, $R^{b12}$), ($R^{a4}$, $R^{b13}$), ($R^{a4}$, $R^{b14}$), ($R^{a4}$, $R^{b15}$), ($R^{a4}$, $R^{b16}$), ($R^{a4}$, $R^{b17}$), ($R^{a4}$, $R^{b18}$), ($R^{a4}$, $R^{b19}$), ($R^{a4}$, $R^{b20}$), ($R^{a4}$, $R^{b21}$), ($R^{a4}$, $R^{b22}$), ($R^{a4}$, $R^{b23}$), ($R^{a4}$, $R^{b24}$), ($R^{a4}$, $R^{b25}$), ($R^{a4}$, $R^{b26}$), ($R^{a4}$, $R^{b27}$), ($R^{a5}$, $R^{b1}$), ($R^{a5}$, $R^{b2}$), ($R^{a5}$, $R^{b3}$), ($R^{a5}$, $R^{b4}$), ($R^{a5}$, $R^{b5}$), ($R^{a5}$, $R^{b6}$), ($R^{a5}$, $R^{b7}$), ($R^{a5}$, $R^{b8}$), ($R^{a5}$, $R^{b9}$), $R^{a5}$, $R^{b10}$), ($R^{a5}$, $R^{b11}$), ($R^{a5}$, $R^{b12}$), ($R^{a5}$, $R^{b13}$), ($R^{a5}$, $R^{b14}$), ($R^{a5}$, $R^{b15}$), ($R^{a5}$, $R^{b16}$), ($R^{a5}$, $R^{b17}$), ($R^{a5}$, $R^{b18}$), ($R^{a5}$, $R^{b19}$), ($R^{a5}$, $R^{b20}$), ($R^{a5}$, $R^{b21}$), ($R^{a5}$, $R^{b22}$), ($R^{a5}$, $R^{b23}$), ($R^{a5}$, $R^{b24}$), ($R^{a5}$, $R^{b25}$), ($R^{a5}$, $R^{b26}$), ($R^{a5}$, $R^{b27}$), ($R^{a6}$, $R^{b1}$), ($R^{a6}$, $R^{b2}$), ($R^{a6}$, $R^{b3}$), ($R^{a6}$, $R^{b4}$), ($R^{a6}$, $R^{b5}$), ($R^{a6}$, $R^{b6}$), ($R^{a6}$, $R^{b7}$), ($R^{a6}$, $R^{b8}$), ($R^{a6}$, $R^{b9}$), ($R^{a6}$, $R^{b10}$), ($R^{a6}$, $R^{b11}$), ($R^{a6}$, $R^{b12}$), ($R^{a6}$, $R^{b13}$), ($R^{a6}$, $R^{b14}$), ($R^{a6}$, $R^{b15}$), ($R^{a6}$, $R^{b16}$), ($R^{a6}$, $R^{b17}$), ($R^{a6}$, $R^{b18}$), ($R^{a6}$, $R^{b19}$), ($R^{a6}$, $R^{b20}$), ($R^{a6}$, $R^{b21}$), ($R^{a6}$, $R^{b22}$), ($R^{a6}$, $R^{b23}$), ($R^{a6}$, $R^{b24}$), ($R^{a6}$, $R^{b25}$), ($R^{a6}$, $R^{b26}$), ($R^{a6}$, $R^{b27}$).

EXAMPLES

This invention is further explained by the following Examples, which are not intended to limit the scope of this invention.

The abbreviations used in the present description stand for the following meanings.
Me: methyl
Et: ethyl
Bu: butyl
Ph: phenyl
PPh₃, TPP: triphenylphosphine
AcOEt: ethyl aceate
DMF: N,N-dimethylformamide
TFA: trifluoroacetic acid
DMSO: dimethylsulfoxide
THF: tetrahydrofuran
DIEA, Hunig's Base: N,N-diisopropylethyl amine
TBAF: tetrabutylammonium fluoride
SEM: 2-(trimethylsilyl)ethoxymethyl
OAc: acetate group
mCPBA: m-chloroperoxybenzoic acid
NMP: 1-methylpyrrolidine-2-one
LAH: lithium aluminum hydride
DBU: 1,8-Diazabicyclo[5.4.0]undec-7-ene
DCM: methylene chloride
TEA: triethylamine $^1$H NMR spectra of the examples were measured on 300 MHz in d6-DMSO or CDCl₃.

"RT" in the specification represents "Retention Time" by LC/MS: Liquid Chromatography/Mass Spectrometry.

LC/MS data of the compounds were measured under the following condition.

Column: Shim-pack XR-ODS (2.2 μm、i.d.50×3.0 mm) (Shimadzu)
Flow rate: 1.6 mL/min
UV detection wavelength: 254 nm
Mobile phase: [A] is 0.1% formic acid-containing aqueous solution, and [B] is 0.1% formic acid-containing acetonitrile solution.
Gradient: Linear gradient of 10% to 100% solvent [B] for 3 minutes was performed, and 100% solvent [B] was maintained for 1 minute.

Example 1

Preparation of Compound I-020

Step 1

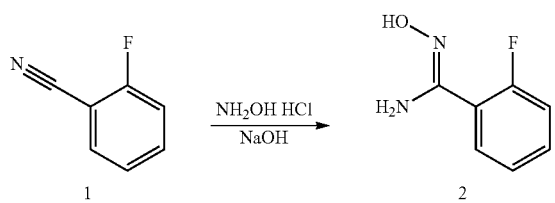

To ethanol solution (5 mL) of Compound 1 (500 mg, 4.13 mmol), were added hydroxylamine hydrochloride (287 mg, 4.13 mmol) and 14 mol/L aqueous sodium hydroxide (0.30 ml、4.13 mmol), and the mixture was stirred at room temperature overnight. The precipitated solid was filtered off and the filtrate was condensed under reduced pressure. The residue was purified by silica gel chromatography (chloroform:methanol=100:0→95:5) to afford Compound 2 (382 mg, yield 60%) as colorless oil.

Step 2

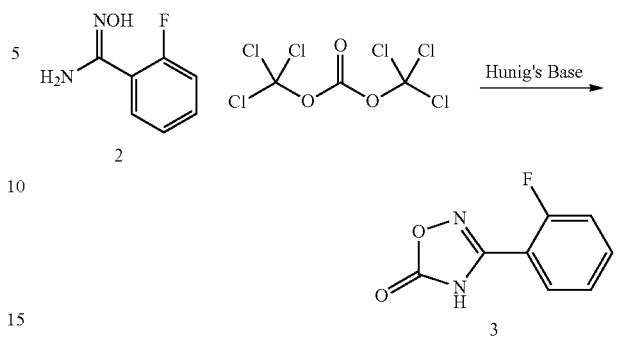

To THF solution (5 mL) of Compound 2 (380 mg, 2.47 mmol) obtained in Step 1, Hunig's base (0.86 ml、4.93 mmol) and triphosgene (293 mg, 0.986 mmol) were added, and the mixture was refluxed for 1 hour. The reaction solution was condensed under reduced pressure. To the residue, was added water (30 mL), and the water layer was extracted with ethyl acetate. The organic layer was extracted with pH14 alkaline aqueous solution, and the water layer was acidized. The water layer was extracted with chloroform. The organic layer was dried over magnesium sulfate and condensed under reduced pressure to afford Compound 3 (350 mg, yield 79%) as white solid.

Step 3

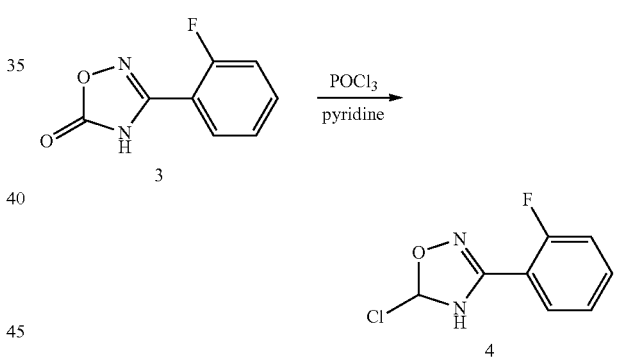

To Compound 3 obtained in Step 2, was added phosphoryl chloride (3 ml, 32.3 mmol). To the mixture was added pyridine (0.13 ml, 1.59 mmol) dropwise and the mixture was stirred at 130° C. for 1.5 hours. The reaction solution was cooled at room temperature and poured into ice. The precipitated solid was filtered off and dried under reduced pressure to afford the desired compound 4 (205 mg, yield 72%) as white solid.

LC (RT): 2.05 min

Step 4

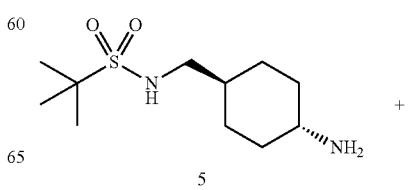

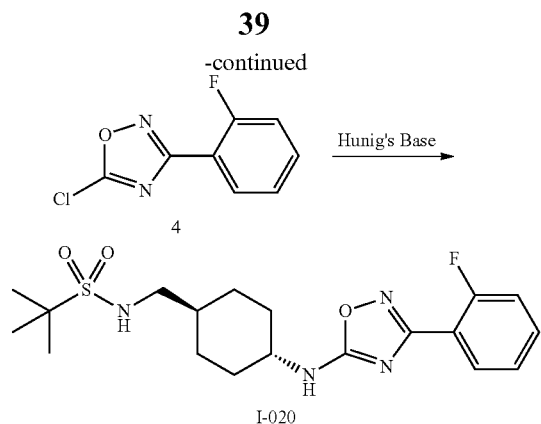

To DMF solution (3 mL) of Compound 5 (50 mg, 0.20 mmol), Compound 4 (50 mg, 0.24 mmol) obtained in Step 3 and Hunig's base (0.07 ml、0.40 mmol) were added at 0° C., and the mixture was stirred for 15 minutes. To the reaction solution, water was added dropwise slowly. The precipitated solid was filtered off to afford Compound I-20 (62 mg, yield 75%).

Example 2

Preparation of Compound I-003

Step 1

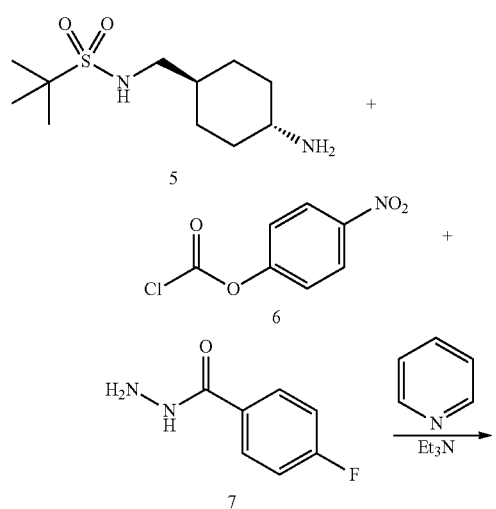

To methylene chloride solution (5 mL) of Compound 5 (100 mg、0.40 mmol), pyridine (0.065 ml、0.805 mmol) was added, then Compound 6 (138 mg、0.684 mmol) was added under ice-cooling. The mixture was stirred for 30 minutes. To the reaction solution, Compound 7 (155 mg, 1.00 mmol), triethylamine (0.14 ml, 1.00 mmol) and acetonitrile (6 ml) were added, the mixture was stirred at room temperature overnight. To the reaction solution, was added water. The water layer was extracted with ethyl acetate. The organic layer was washed with saturated sodium bicarbonate solution, 1 mmol/L hydrochloric acid and saturated brine. The organic layer was dried over magnesium sulfate and condensed under reduced pressure. The residue was washed with isopropyl ether to afford the desired Compound 8 (160 mg, yield 93%) as white solid.

LC(RT): 1.21 min

Step 2

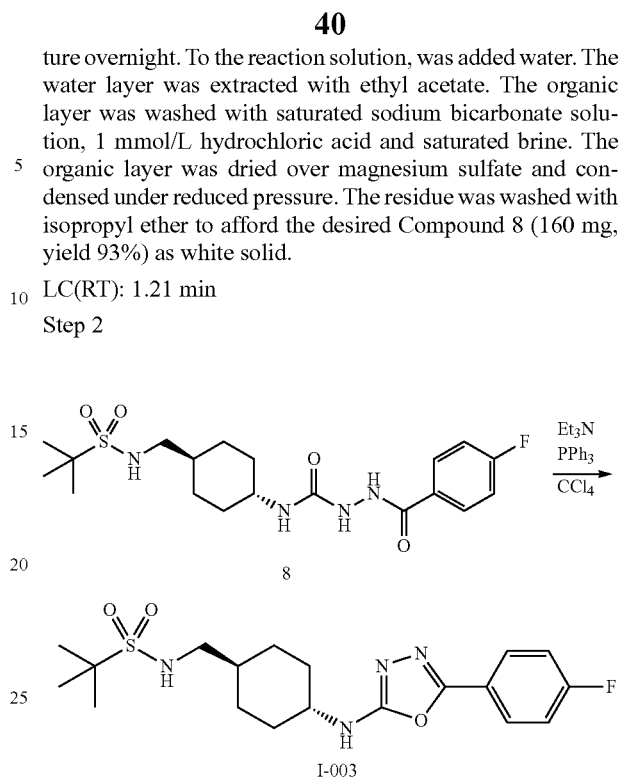

To methylene chloride solution (5 mL) of Compound 8 (100 mg, 0.23 mmol) obtained in Step 2, triphenylphosphine (122 mg, 0.47 mmol), carbon tetrachloride (0.068 ml, 0.70 mmol) and triethylamine (0.26 ml, 1.87 mmol) were added, the mixture was stirred at 80° C. for 30 minutes. Water was poured into the reaction solution, the water layer was extracted with ethyl acetate. The organic layer was washed with saturated brine. The organic layer was dried over anhydrous magnesium sulfate. The solvent was removed under reduced pressure and the residue was purified by silica gel chromatography (chloroform:methanol=100:0→95:5) to afford Compound I-003 (42 mg, yield 44%) as white solid.

Example 3

Preparation of Compound I-007

Step 1

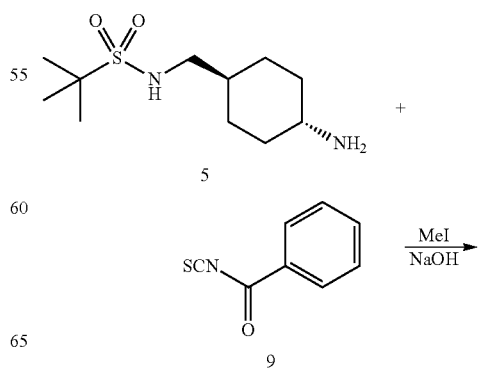

-continued

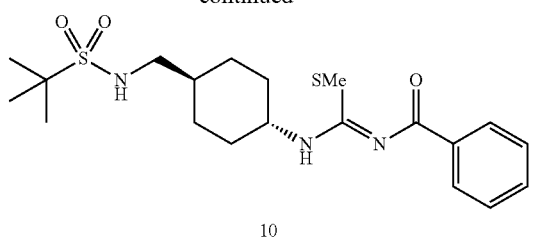

To methylene chloride solution (5 ml) of Compound 10 (100 mg, 0.40 mmol), was added Compound 9 (49 mg, 0.30 mmol), the mixture was stirred room temperature for 30 minutes. To the reaction mixture, was added iodomethane (0.019 ml, 0.40 mmol) and 1 mol/L sodium hydroxide (0.40 ml, 0.40 mmol), the mixture was stirred room temperature overnight. To the reaction mixture, were added iodomethane (0.019 ml, 0.40 mmol) and 1 mol/L sodium hydroxide (0.40 ml, 0.40 mmol), the mixture was stirred room temperature for 10 minutes. Water was poured into the reaction solution, the water layer was extracted with ethyl acetate. The organic layer was washed with 1 mol/L hydrochloric acid and saturated brine. The organic layer was dried over anhydrous magnesium sulfate. The solvent was removed under reduced pressure and the residue was purified by silica gel chromatography (hexane: AcOEt=100:0→60:40) to afford Compound 9 (48 mg, yield 56%) as white solid.

Step 2

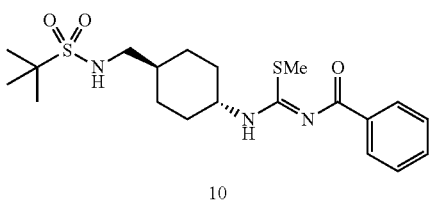

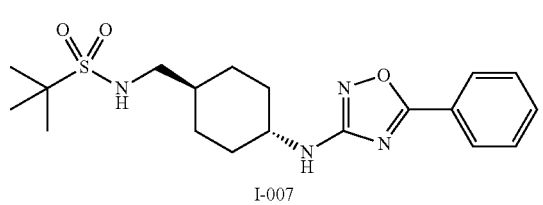

To ethanol solution (3 ml) of Compound 10 (48 mg, 0.11 mmol) obtained in Step 1, was added hydroxylamine (0.069 ml, 1.13 mmol), the mixture was refluxed for 2 hours. To the reaction mixture, was added hydroxylamine (0.346 ml, 5.64 mmol), the mixture was refluxed for 1.5 hours. Water was poured into the reaction solution, the mixture was extracted with ethyl acetate. The organic layer was washed with saturated brine and dried over anhydrous magnesium sulfate. The solvent was removed under reduced pressure and the residue was purified by silica gel chromatography (hexane: AcOEt=100:0→30:70) to afford Compound I-007 (2 mg, yield 5%) as white solid.

Example 4

Preparation of Compound I-146

Step 1

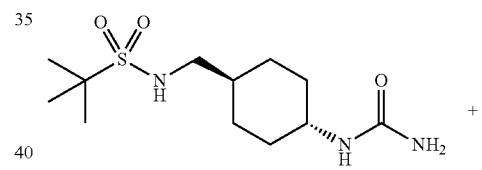

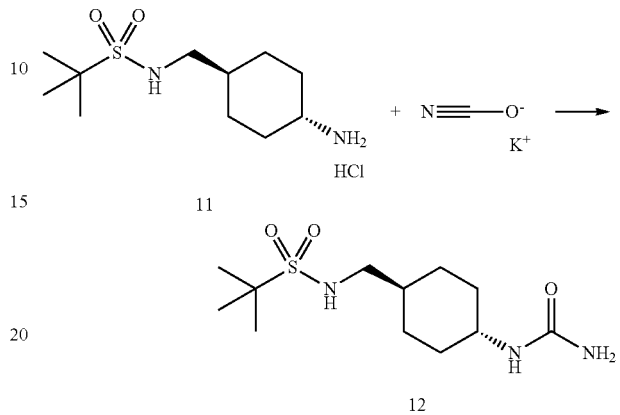

To Compound 11 (2000 mg, 7.02 mmol), was added water (10 ml) to be suspension. To the suspension, was added potassium cyanate (626 mg, 7.7 mmol), the mixture was stirred at 85° C. The reaction solution was cooled to room temperature, and the precipitated solid was filtered off. The filtrate was washed with water and dried under reduced pressure to afford Compound 12 (1670 mg, yield 82%) as white solid.

Step 2

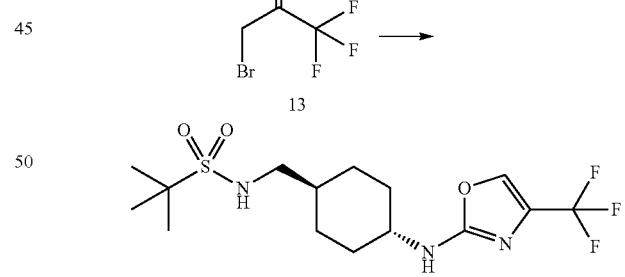

To Compound 12 (1670 mg, 5.74 mmol), were added N-methylpyrolidone (17 ml) and Compound 13 (1200 mg, 6.03 mmol), and the mixture was stirred at 80° C. The reaction solution was cooled to room temperature, and added diethyl ether. The mixture was washed water and saturated brine and dried over magnesium sulfate and condensed under reduced pressure. The precipitated solid was filtered off to give Compound I-146 (830 mg, yield 37%).

Following compounds were synthesized according to the Examples described above.

TABLE 2

| No. | Structure | NMR data/LC/MS data (RT, MS) |
|---|---|---|
| I-001 | 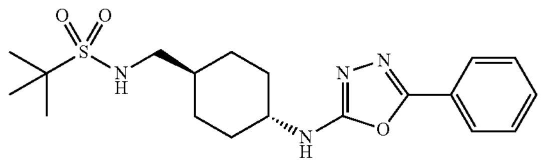 [SMILES: CC(C)(C)S(=O)(=O)NC[C@H]1CC[C@H](Nc2nnc(-c3ccccc3)o2)CC1] | 1H-NMR (DMSO-d6) δ: 0.98-1.04 (2H, m), 1.23-1.33 (12H, m), 1.80-1.83 (2H, m), 2.04-2.07 (2H, m), 2.89 (2H, t, J = 6.3 Hz), 3.35-3.36 (1H, m), 6.87 (1H, t, J = 5.8 Hz), 7.51-7.55 (3H, m), 7.73 (1H, d, J = 7.6 Hz), 7.79-7.81 (2H, m). |
| I-002 | 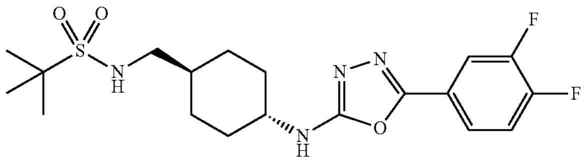 [SMILES: CC(C)(C)S(=O)(=O)NC[C@H]1CC[C@H](Nc2nnc(-c3ccc(F)c(F)c3)o2)CC1] | 1H-NMR (DMSO-d6) δ: 1.00-1.03 (2H, m), 1.22-1.34 (12H, m), 1.80-1.83 (2H, m), 2.03-2.05 (2H, m), 2.89 (2H, t, J = 6.3 Hz), 3.35-3.36 (1H, m), 6.87 (1H, t, J = 5.8 Hz), 7.61-7.64 (2H, m), 7.77-7.82 (2H, m). |
| I-003 | 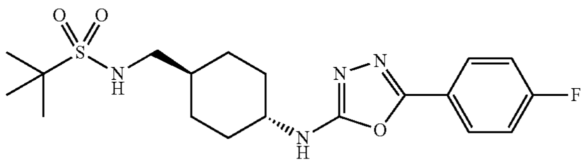 [SMILES: CC(C)(C)S(=O)(=O)NC[C@H]1CC[C@H](Nc2nnc(-c3ccc(F)cc3)o2)CC1] | 1H-NMR (DMSO-d6) δ: 0.98-1.01 (2H, m), 1.24-1.26 (12H, m), 1.80-1.83 (2H, m), 2.05-2.06 (2H, m), 2.89 (2H, t, J = 6.3 Hz), 3.35-3.36 (1H, m), 6.87 (1H, t, J = 5.8 Hz), 7.35-7.40 (2H, m), 7.73 (1H, d, J = 7.6 Hz), 7.84-7.85 (2H, m). |
| I-004 | 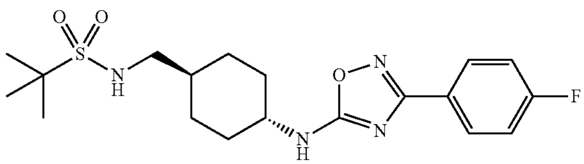 [SMILES: CC(C)(C)S(=O)(=O)NC[C@H]1CC[C@H](Nc2nc(-c3ccc(F)cc3)no2)CC1] | 1H-NMR (DMSO-d6) δ: 0.99-1.05 (2H, m), 1.24-1.34 (12H, m), 1.81-1.83 (2H, m), 2.01-2.03 (2H, m), 2.89 (2H, t, J = 6.1 Hz), 3.45-3.46 (1H, m), 6.87 (1H, t, J = 6.1 Hz), 7.34 (2H, t, J = 8.9 Hz), 7.91-7.95 (2H, m), 8.42 (1H, d, J = 7.6 Hz). |
| I-005 | 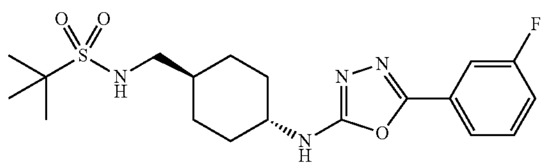 [SMILES: CC(C)(C)S(=O)(=O)NC[C@H]1CC[C@H](Nc2nnc(-c3cccc(F)c3)o2)CC1] | 1H-NMR (DMSO-d6) δ: 0.98-1.05 (2H, m), 1.21-1.36 (12H, m), 1.80-1.83 (2H, m), 2.03-2.06 (2H, m), 2.89 (2H, t, J = 6.3 Hz), 3.34-3.38 (1H, m), 6.87 (1H, t, J = 6.1 Hz), 7.36-7.38 (1H, m), 7.53-7.65 (3H, m), 7.82 (1H, d, J = 7.6 Hz). |

TABLE 3

| No. | Structure | NMR data/LC/MS data (RT, MS) |
|---|---|---|
| I-006 | 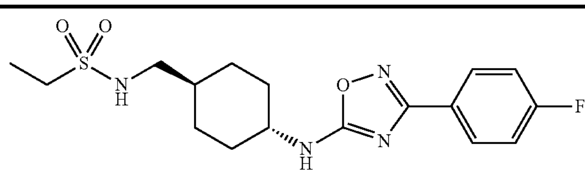 | 1H-NMR (DMSO-d6) δ: 1.00-1.07 (2H, m), 1.22-1.33 (6H, m), 1.80-1.83 (2H, m), 2.01-2.02 (2H, m), 2.78 (2H, t, J = 6.3 Hz), 2.98 (2H, q, J = 7.3 Hz), 3.44-3.47 (1H, m), 7.02 (1H, t, J = 6.1 Hz), 7.34 (2H, t, J = 8.9 Hz), 7.92-7.94 (2H, m), 8.43 (1H, d, J = 7.6 Hz). |
| I-007 | 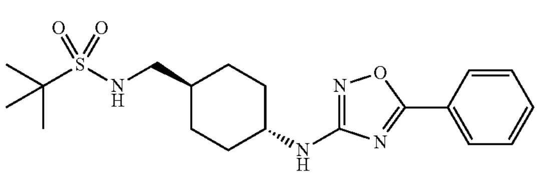 [SMILES: CC(C)(C)S(=O)(=O)NC[C@H]1CC[C@H](Nc2noc(-c3ccccc3)n2)CC1] | 1H-NMR (DMSO-d6) δ: 0.97-1.03 (2H, m), 1.16-1.38 (13H, m), 1.79-1.82 (2H, m), 2.01-2.03 (2H, m), 2.88 (2H, t, J = 6.3 Hz), 3.19-3.22 (1H, m), 6.84-6.91 (2H, m), 7.60-7.67 (3H, m), 7.94-8.00 (2H, m). |
| I-008 | 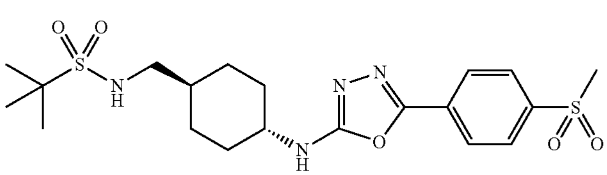 [SMILES: CC(C)(C)S(=O)(=O)NC[C@H]1CC[C@H](Nc2nnc(-c3ccc(S(C)(=O)=O)cc3)o2)CC1] | 1H-NMR (DMSO-d6) δ: 0.99-1.06 (2H, m), 1.26-1.33 (13H, m), 1.82-1.83 (2H, m), 2.05-2.07 (2H, m), 2.89 (2H, t, J = 6.3 Hz), 3.17 (1H, d, J = 5.1 Hz), 3.27 (3H, s), 3.38-3.42 (1H, m), 6.87 (1H, t, J = 5.8 Hz), 7.95 (1H, d, J = 7.6 Hz), 8.02-8.08 (4H, m). |

TABLE 3-continued

| No. | Structure | NMR data/LC/MS data (RT, MS) |
|---|---|---|
| I-009 | 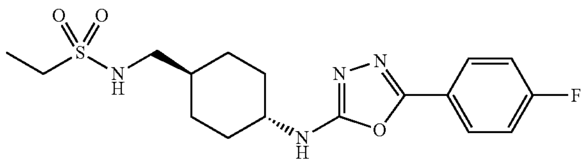 [SMILES: CCS(=O)(=O)NC[C@H]1CC[C@H](Nc2nnc(-c3ccc(F)cc3)o2)CC1] | 1H-NMR (DMSO-d6) δ: 0.98-1.05 (2H, m), 1.18-1.25 (5H, m), 1.37-1.38 (1H, m), 1.80-1.83 (2H, m), 2.03-2.06 (2H, m), 2.78 (2H, t, J = 6.3 Hz), 2.98 (2H, q, J = 7.4 Hz), 3.35-3.37 (1H, m), 7.01 (1H, t, J = 6.1 Hz), 7.35-7.40 (2H, m), 7.73 (1H, d, J = 7.6 Hz), 7.83-7.86 (2H, m). |
| I-010 | 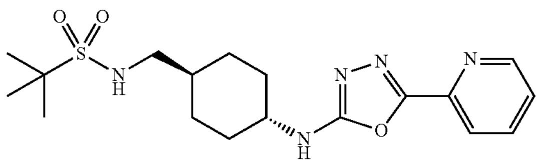 [SMILES: CC(C)(C)S(=O)(=O)NC[C@H]1CC[C@H](Nc2nnc(-c3ccccn3)o2)CC1] | 1H-NMR (DMSO-d6) δ: 1.00-1.03 (2H, m), 1.25-1.33 (12H, m), 1.81-1.83 (2H, m), 2.04-2.07 (2H, m), 2.89 (2H, t, J = 6.1 Hz), 3.36-3.38 (1H, m), 6.87 (1H, t, J = 5.8 Hz), 7.48-7.52 (1H, m), 7.91-7.96 (3H, m), 8.66-8.67 (1H, m). |

TABLE 4

| No. | Structure | NMR data/LC/MS data (RT, MS) |
|---|---|---|
| I-011 | 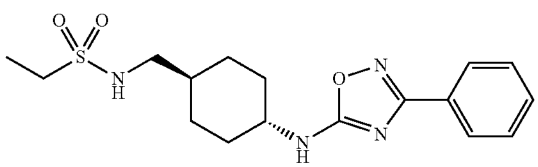 [SMILES: CCS(=O)(=O)NC[C@H]1CC[C@H](Nc2nc(-c3ccccc3)no2)CC1] | 1H-NMR (DMSO-d6) δ: 1.02-1.05 (2H, m), 1.17-1.40 (6H, m), 1.80-1.83 (2H, m), 2.00-2.04 (2H, m), 2.78 (2H, t, J = 6.3 Hz), 2.98 (2H, q, J = 7.3 Hz), 3.44-3.48 (1H, m), 7.01 (1H, t, J = 6.1 Hz), 7.49-7.51 (3H, m), 7.87-7.90 (2H, m), 8.40 (1H, d, J = 8.1 Hz). |
| I-012 | 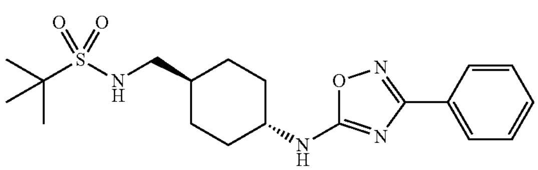 [SMILES: CC(C)(C)S(=O)(=O)NC[C@H]1CC[C@H](Nc2nc(-c3ccccc3)no2)CC1] | 1H-NMR (DMSO-d6) δ: 1.00-1.06 (2H, m), 1.22-1.38 (12H, m), 1.81-1.84 (2H, m), 2.01-2.04 (2H, m), 2.89 (2H, t, J = 6.1 Hz), 3.44-3.48 (1H, m), 6.87 (1H, t, J = 5.8 Hz), 7.48-7.52 (3H, m), 7.88-7.90 (2H, m), 8.39 (1H, d, J = 7.6 Hz). |
| I-013 | 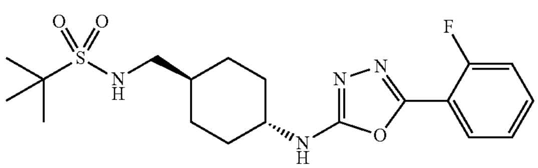 [SMILES: CC(C)(C)S(=O)(=O)NC[C@H]1CC[C@H](Nc2nnc(-c3ccccc3F)o2)CC1] | 1H-NMR (DMSO-d6) δ: 0.97-1.02 (2H, m), 1.19-1.38 (12H, m), 1.80-1.83 (2H, m), 2.04-2.07 (2H, m), 2.89 (2H, t, J = 6.3 Hz), 3.36-3.38 (1H, m), 6.87 (1H, t, J = 6.1 Hz), 7.34-7.43 (2H, m), 7.55-7.60 (1H, m), 7.81-7.87 (2H, m). |
| I-014 | 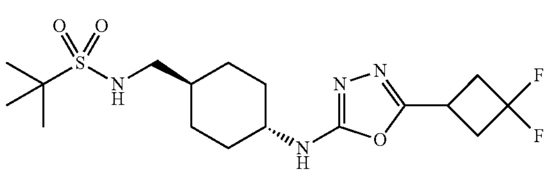 [SMILES: CC(C)(C)S(=O)(=O)NC[C@H]1CC[C@H](Nc2nnc(C3CC(F)(F)C3)o2)CC1] | 1H-NMR (DMSO-d6) δ: 0.89-1.02 (2H, m), 1.12-1.39 (12H, m), 1.75-1.83 (2H, m), 1.96-2.04 (2H, m), 2.80-2.92 (4H, m), 2.97-3.09 (2H, m), 3.19-3.29 (1H, m), 3.45-3.52 (1H, m), 6.85 (1H, t, J = 5.8 Hz), 7.45 (1H, d, J = 8.1 Hz). |
| I-015 | 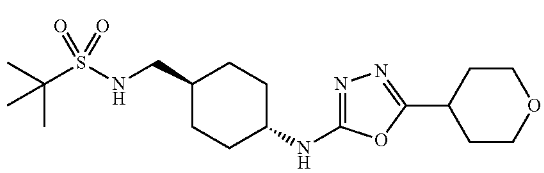 [SMILES: CC(C)(C)S(=O)(=O)NC[C@H]1CC[C@H](Nc2nnc(C3CCOCC3)o2)CC1] | 1H-NMR (DMSO-d6) δ: 0.90-1.01 (2H, m), 1.13-1.38 (12H, m), 1.59-1.69 (2H, m), 1.75-1.87 (4H, m), 1.96-2.03 (2H, m), 2.87 (2H, t, J = 6.3 Hz), 2.97-3.05 (1H, m), 3.16-3.27 (1H, m), 3.39-3.45 (2H, m), 3.83-3.89 (2H, m), 6.85 (1H, t, J = 5.8 Hz), 7.34 (1H, d, J = 8.0 Hz) |

TABLE 5

| No. | Structure | NMR data/LC/MS data (RT, MS) |
|---|---|---|
| I-016 | 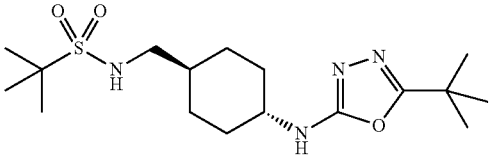 [SMILES: CC(C)(C)c1nnc(N[C@H]2CC[C@H](CNS(=O)(=O)C(C)(C)C)CC2)o1] | 1H-NMR (DMSO-d6) δ: 0.90-1.01 (2H, m), 1.10-1.38 (21H, m), 1.75-1.82 (2H, m), 1.96-2.04 (2H, m), 2.87 (2H, t, J = 6.3 Hz), 3.17-3.26 (1H, m), 6.85 (1H, t, J = 5.8 Hz), 7.30 (1H, d, J = 7.6 Hz). |
| I-017 | 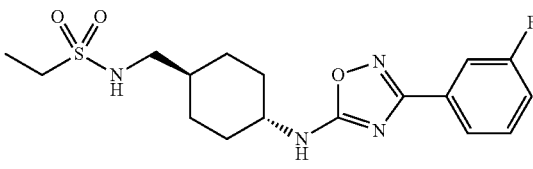 | 1H-NMR (DMSO-d6) δ: 1.00-1.06 (2H, m), 1.17-1.38 (6H, m), 1.80-1.83 (2H, m), 1.99-2.04 (2H, m), 2.78 (2H, t, J = 6.3 Hz), 2.98 (2H, q, J = 7.4 Hz), 3.45-3.47 (1H, m), 7.02 (1H, t, J = 6.1 Hz), 7.37-7.41 (1H, m), 7.54-7.62 (2H, m), 7.74 (1H, d, J = 8.1 Hz), 8.49 (1H, d, J = 7.6 Hz). |
| I-018 | 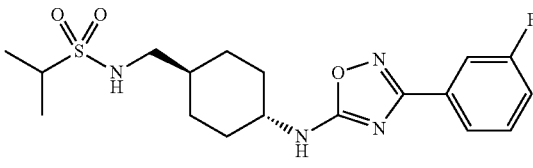 | 1H-NMR (DMSO-d6) δ: 1.00-1.06 (2H, m), 1.21-1.37 (9H, m), 1.80-1.83 (2H, m), 2.00-2.02 (2H, m), 2.81 (2H, t, J = 6.3 Hz), 3.14-3.16 (1H, m), 3.46-3.47 (1H, m), 6.98 (1H, t, J = 6.1 Hz), 7.38-7.40 (1H, m), 7.54-7.62 (2H, m), 7.74 (1H, d, J = 7.6 Hz), 8.49 (1H, d, J = 8.1 Hz). |
| I-019 | 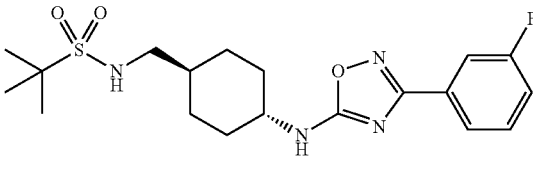 | 1H-NMR (DMSO-d6) δ: 1.01-1.06 (2H, m), 1.30 (12H, tt, J = 26.6, 6.3 Hz), 1.81-1.84 (2H, m), 2.00-2.03 (2H, m), 2.89 (2H, t, J = 6.3 Hz), 3.44-3.48 (1H, m), 6.87 (1H, t, J = 5.8 Hz), 7.38-7.40 (1H, m), 7.56-7.60 (2H, m), 7.74 (1H, d, J = 7.6 Hz), 8.48 (1H, d, J = 7.6 Hz). |
| I-020 | 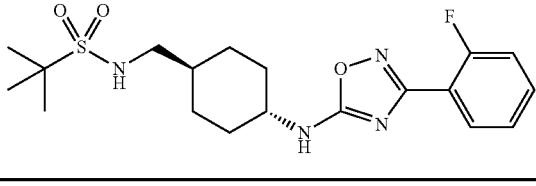 | 1H-NMR (DMSO-d6) δ: 1.00-1.05 (2H, m), 1.22-1.37 (12H, m), 1.80-1.83 (2H, m), 2.00-2.03 (2H, m), 2.89 (2H, t, J = 6.1 Hz), 3.43-3.47 (1H, m), 6.87 (1H, t, J = 5.8 Hz), 7.33-7.39 (2H, m), 7.55-7.61 (1H, m), 7.90-7.92 (1H, m), 8.46 (1H, d, J = 7.6 Hz). |

TABLE 6

| No. | Structure | NMR data/LC/MS data (RT, MS) |
|---|---|---|
| I-021 | 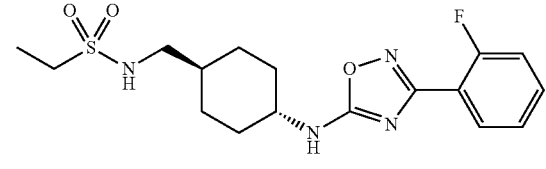 [SMILES: CCS(=O)(=O)NC[C@H]1CC[C@H](Nc2nc(-c3ccccc3F)no2)CC1] | 1H-NMR (DMSO-d6) δ: 1.02-1.05 (2H, m), 1.17-1.39 (6H, m), 1.80-1.83 (2H, m), 2.00-2.02 (2H, m), 2.78 (2H, t, J = 6.3 Hz), 2.98 (2H, q, J = 7.3 Hz), 3.43-3.47 (1H, m), 7.02 (1H, t, J = 6.1 Hz), 7.34-7.38 (2H, m), 7.55-7.61 (1H, m), 7.90-7.92 (1H, m), 8.47 (1H, d, J = 7.6 Hz). |
| I-022 | 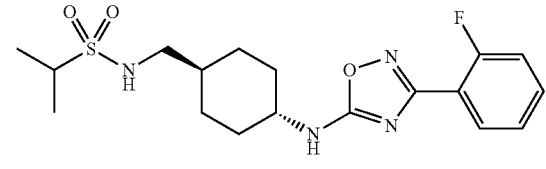 [SMILES: CC(C)S(=O)(=O)NC[C@H]1CC[C@H](Nc2nc(-c3ccccc3F)no2)CC1] | 1H-NMR (DMSO-d6) δ: 1.01-1.05 (2H, m), 1.25-1.33 (9H, m), 1.80-1.83 (2H, m), 2.01-2.03 (2H, m), 2.81 (2H, t, J = 6.3 Hz), 3.14-3.16 (1H, m), 3.44-3.46 (1H, m), 6.98 (1H, t, J = 6.1 Hz), 7.34-7.38 (2H, m), 7.56-7.59 (1H, m), 7.90-7.92 (1H, m), 8.46 (1H, d, J = 7.6 Hz). |

TABLE 6-continued

| No. | Structure | NMR data/LC/MS data (RT, MS) |
|---|---|---|
| I-023 | 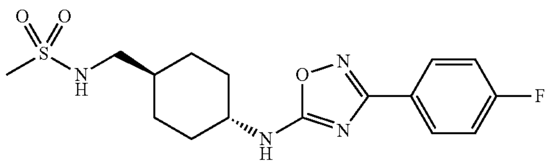 [SMILES: CS(=O)(=O)NC[C@H]1CC[C@H](Nc2nc(-c3ccc(F)cc3)no2)CC1] | 1H-NMR (DMSO-d6) δ: 1.00-1.05 (2H, m), 1.23-1.39 (3H, m), 1.81 (2H, d, J = 13.2 Hz), 2.02 (2H, d, J = 10.1 Hz), 2.80 (2H, t, J = 6.6 Hz), 2.88 (3H, s), 3.45-3.46 (1H, m), 6.98 (1H, t, J = 6.1 Hz), 7.34 (2H, t, J = 8.9 Hz), 7.93 (2H, dd, J = 8.6, 5.6 Hz), 8.43 (1H, d, J = 8.1 Hz). LC/MS (RT) = 1.80 LC/MS (MS) = 369.30 |
| I-024 | 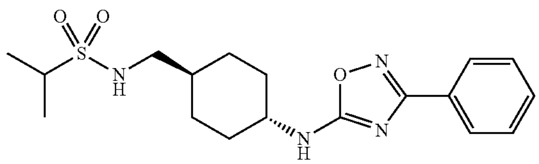 [SMILES: CC(C)S(=O)(=O)NC[C@H]1CC[C@H](Nc2nc(-c3ccccc3)no2)CC1] | 1H-NMR (DMSO-d6) δ: 1.00-1.06 (2H, m), 1.21-1.38 (9H, m), 1.81-1.83 (2H, m), 2.01-2.03 (2H, m), 2.81 (2H, t, J = 6.3 Hz), 3.12-3.18 (1H, m), 3.44-3.48 (1H, m), 6.98 (1H, t, J = 6.1 Hz), 7.47-7.53 (3H, m), 7.88-7.89 (2H, m), 8.40 (1H, d, J = 8.1 Hz). |

TABLE 7

| No. | Structure | NMR data/LC/MS data (RT, MS) |
|---|---|---|
| I-025 | 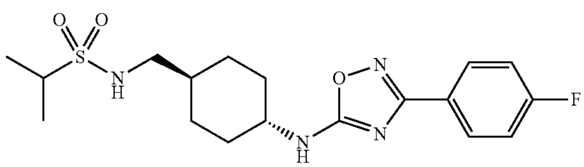 [SMILES: CC(C)S(=O)(=O)NC[C@H]1CC[C@H](Nc2nc(-c3ccc(F)cc3)no2)CC1] | 1H-NMR (DMSO-d6) δ: 0.99-1.06 (2H, m), 1.21-1.38 (9H, m), 1.80-1.83 (2H, m), 2.00-2.02 (2H, m), 2.81 (2H, t, J = 6.3 Hz), 3.12-3.16 (1H, m), 3.43-3.47 (1H, m), 6.98 (1H, t, J = 6.1 Hz), 7.32-7.36 (2H, m), 7.92-7.94 (2H, m), 8.43 (1H, d, J = 7.6 Hz). |
| I-026 | 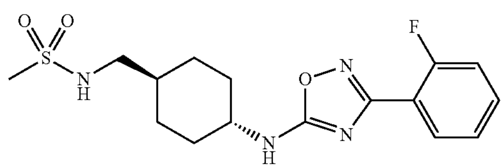 [SMILES: CS(=O)(=O)NC[C@H]1CC[C@H](Nc2nc(-c3ccccc3F)no2)CC1] | 1H-NMR (DMSO-d6) δ: 1.01-1.08 (2H, m), 1.24-1.39 (3H, m), 1.81-1.82 (2H, m), 1.99-2.04 (2H, m), 2.80 (2H, t, J = 6.3 Hz), 2.88 (3H, s), 3.43-3.47 (1H, m), 6.99 (1H, t, J = 6.1 Hz), 7.33-7.39 (2H, m), 7.56-7.59 (1H, m), 7.90-7.92 (1H, m), 8.47 (1H, d, J = 8.1 Hz). |
| I-027 | 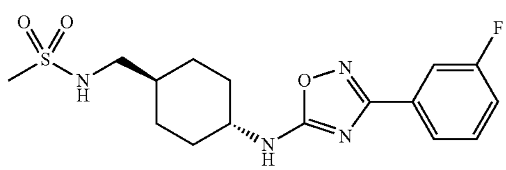 [SMILES: CS(=O)(=O)NC[C@H]1CC[C@H](Nc2nc(-c3cccc(F)c3)no2)CC1] | 1H-NMR (DMSO-d6) δ: 1.03-1.06 (2H, m), 1.24-1.39 (3H, m), 1.80-1.83 (2H, m), 1.99-2.03 (2H, m), 2.80 (2H, t, J = 6.6 Hz), 2.88 (3H, s), 3.46-3.48 (1H, m), 6.99 (1H, t, J = 6.1 Hz), 7.38-7.40 (1H, m), 7.54-7.62 (2H, m), 7.74 (1H, d, J = 8.1 Hz), 8.49 (1H, d, J = 7.6 Hz). |
| I-028 | 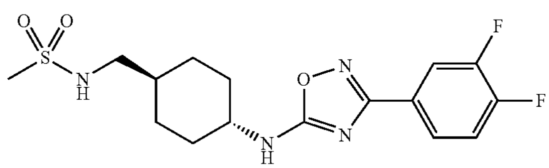 [SMILES: CS(=O)(=O)NC[C@H]1CC[C@H](Nc2nc(-c3ccc(F)c(F)c3)no2)CC1] | 1H-NMR (DMSO-d6) δ: 1.01-1.06 (2H, m), 1.26-1.39 (3H, m), 1.81-1.82 (2H, m), 1.99-2.03 (2H, m), 2.80 (2H, t, J = 6.3 Hz), 2.88 (3H, s), 3.45-3.47 (1H, m), 6.99 (1H, t, J = 6.1 Hz), 7.57-7.62 (1H, m), 7.73-7.86 (2H, m), 8.51 (1H, d, J = 8.1 Hz). |
| I-029 | 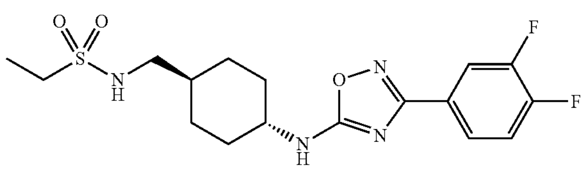 [SMILES: CCS(=O)(=O)NC[C@H]1CC[C@H](Nc2nc(-c3ccc(F)c(F)c3)no2)CC1] | 1H-NMR (DMSO-d6) δ: 1.02-1.05 (2H, m), 1.22-1.32 (6H, m), 1.80-1.83 (2H, m), 2.00-2.02 (2H, m), 2.78 (2H, t, J = 6.3 Hz), 2.98 (2H, q, J = 7.3 Hz), 3.44-3.48 (1H, m), 7.02 (1H, t, J = 6.1 Hz), 7.57-7.60 (1H, m), 7.73-7.85 (2H, m), 8.51 (1H, d, J = 8.1 Hz). |

TABLE 8

| No. | Structure | NMR data/LC/MS data (RT, MS) |
|---|---|---|
| I-030 | 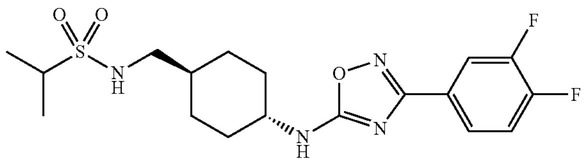 [SMILES: CC(C)S(=O)(=O)NC[C@H]1CC[C@H](Nc2nc(-c3ccc(F)c(F)c3)no2)CC1] | 1H-NMR (DMSO-d6) δ: 1.01-1.05 (2H, m), 1.25-1.33 (9H, m), 1.80-1.83 (2H, m), 1.99-2.03 (2H, m), 2.81 (2H, t, J = 6.3 Hz), 3.14-3.16 (1H, m), 3.45-3.47 (1H, m), 6.98 (1H, t, J = 5.8 Hz), 7.57-7.60 (1H, m), 7.73-7.85 (2H, m), 8.51 (1H, d, J = 7.6 Hz). |
| I-031 | 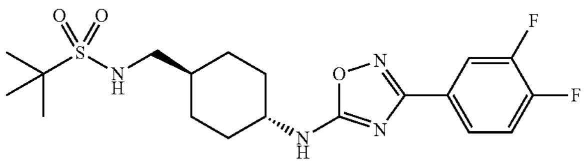 [SMILES: CC(C)(C)S(=O)(=O)NC[C@H]1CC[C@H](Nc2nc(-c3ccc(F)c(F)c3)no2)CC1] | 1H-NMR (DMSO-d6) δ: 0.99-1.03 (2H, m), 1.24-1.31 (12H, m), 1.81-1.83 (2H, m), 2.01-2.03 (2H, m), 2.89 (2H, t, J = 6.3 Hz), 3.45-3.47 (1H, m), 6.87 (1H, t, J = 5.8 Hz), 7.57-7.62 (1H, m), 7.73-7.86 (2H, m), 8.50 (1H, d, J = 7.6 Hz). |
| I-032 | 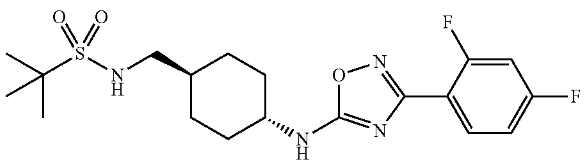 [SMILES: CC(C)(C)S(=O)(=O)NC[C@H]1CC[C@H](Nc2nc(-c3ccc(F)cc3F)no2)CC1] | 1H-NMR (DMSO-d6) δ: 0.95-1.05 (2H, m), 1.27-1.40 (12H, m), 1.78-1.86 (2H, m), 1.98-2.06 (2H, m), 2.89 (2H, dd, J = 7.1, 5.6 Hz), 3.42-3.46 (1H, m), 6.87 (1H, t, J = 6.1 Hz), 7.22-7.27 (1H, m), 7.41-7.47 (1H, m), 7.94-8.00 (1H, m), 8.49 (1H, d, J = 7.6 Hz). LC/MS (RT) = 2.15 LC/MS (MS) = 429.2 |
| I-033 | 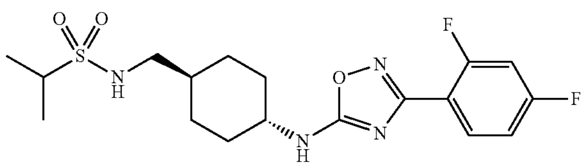 [SMILES: CC(C)S(=O)(=O)NC[C@H]1CC[C@H](Nc2nc(-c3ccc(F)cc3F)no2)CC1] | 1H-NMR (DMSO-d6) δ: 0.95-1.06 (2H, m), 1.20-1.42 (10H, m), 1.80-1.83 (2H, m), 2.00-2.04 (2H, m), 2.80 (2H, t, J = 6.3 Hz), 3.11-3.18 (1H, m), 3.39-3.49 (1H, m), 6.98 (1H, t, J = 6.1 Hz), 7.25 (1H, td, J = 8.5, 2.4 Hz), 7.41-7.47 (1H, m), 7.97 (1H, td, J = 8.4, 6.8 Hz), 8.49 (1H, d, J = 7.6 Hz). LC/MS (RT) = 2.02 LC/MS (MS) = 415.2 |

TABLE 9

| No. | Structure | NMR data/LC/MS data (RT, MS) |
|---|---|---|
| I-034 | 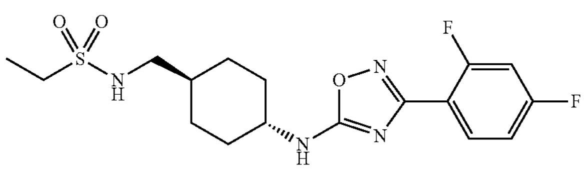 [SMILES: CCS(=O)(=O)NC[C@H]1CC[C@H](Nc2nc(-c3ccc(F)cc3F)no2)CC1] | 1H-NMR (DMSO-d6) δ: 0.96-1.06 (2H, m), 1.17-1.43 (6H, m), 1.80-1.83 (2H, m), 2.00-2.03 (2H, m), 2.78 (2H, t, J = 6.3 Hz), 2.98 (2H, q, J = 7.3 Hz), 3.39-3.49 (1H, m), 7.01 (1H, t, J = 5.8 Hz), 7.25 (1H, td, J = 8.5, 2.4 Hz), 7.41-7.47 (1H, m), 7.94-8.00 (1H, m), 8.49 (1H, d, J = 7.6 Hz). LC/MS (RT) = LC/MS (MS) = 401.2 |
| I-035 | 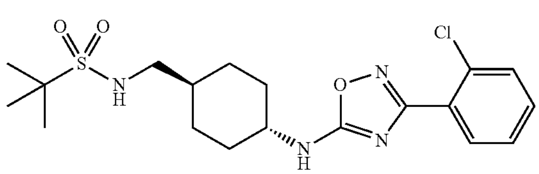 [SMILES: CC(C)(C)S(=O)(=O)NC[C@H]1CC[C@H](Nc2nc(-c3ccccc3Cl)no2)CC1] | 1H-NMR (DMSO-d6) δ: 0.94-1.04 (2H, m), 1.27-1.40 (12H, m), 1.78-1.85 (2H, m), 1.99-2.06 (2H, m), 2.88 (2H, t, J = 6.3 Hz), 3.38-3.46 (1H, m), 6.87 (1H, t, J = 5.8 Hz), 7.47 (1H, td, J = 7.5, 1.4 Hz), 7.54 (1H, td, J = 7.6, 1.9 Hz), 7.61 (1H, dd, J = 8.1, 1.5 Hz), 7.79 (1H, dd, J = 7.6, 1.5 Hz), 8.47 (1H, d, J = 7.6 Hz). |

TABLE 9-continued

| No. | Structure | NMR data/LC/MS data (RT, MS) |
|---|---|---|
| I-036 | 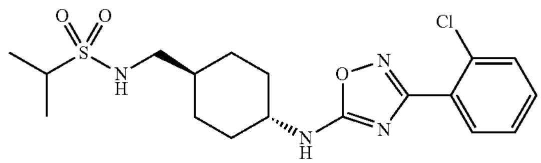 | 1H-NMR (DMSO-d6) δ: 0.94-1.05 (2H, m), 1.20-1.41 (9H, m), 1.78-1.85 (2H, m), 1.98-2.06 (2H, m), 2.80 (2H, t, J = 6.1 Hz), 3.11-3.18 (1H, m), 3.37-3.46 (1H, m), 6.98 (1H, t, J = 5.8 Hz), 7.47 (1H, td, J = 7.4, 1.4 Hz), 7.54 (1H, td, J = 7.6, 1.7 Hz), 7.61 (1H, dd, J = 7.9, 1.3 Hz), 7.79 (1H, dd, J = 7.6, 2.0 Hz), 8.47 (1H, d, J = 7.6 Hz). |
| I-037 | 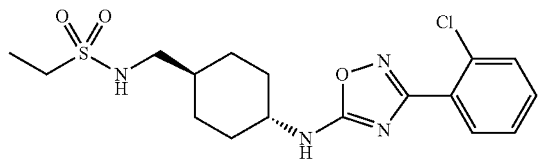 | 1H-NMR (DMSO-d6) δ: 0.95-1.05 (1H, m), 1.18 (3H, t, J = 7.4 Hz), 1.22-1.43 (3H, m), 1.78-1.85 (2H, m), 1.99-2.06 (2H, m), 2.77 (2H, t, J = 6.3 Hz), 2.97 (2H, q, J = 7.3 Hz), 3.38-3.47 (1H, m), 7.01 (1H, t, J = 6.1 Hz), 7.47 (1H, td, J = 7.5, 1.4 Hz), 7.54 (1H, td, J = 7.6, 1.9 Hz), 7.61 (1H, dd, J = 7.9, 1.3 Hz), 7.79 (1H, dd, J = 7.6, 1.5 Hz), 8.47 (1H, d, J = 7.6 Hz). |

TABLE 10

| No. | Structure | NMR data/LC/MS data (RT, MS) |
|---|---|---|
| I-038 | 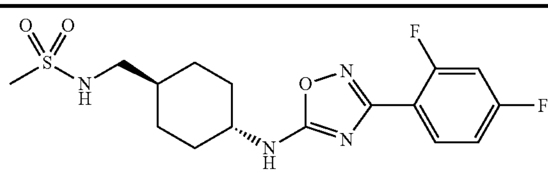 | 1H-NMR (DMSO-d6) δ: 0.97-1.07 (2H, m), 1.23-1.33 (2H, m), 1.34-1.43 (1H, m), 1.77-1.85 (2H, m), 1.98-2.06 (2H, m), 2.80 (2H, t, J = 6.6 Hz), 2.87 (4H, s), 3.39-3.50 (1H, m), 6.98 (1H, t, J = 6.1 Hz), 7.25 (1H, td, J = 8.5, 2.2 Hz), 7.41-7.47 (1H, m), 7.97 (1H, td, J = 8.5, 6.8 Hz), 8.49 (1H, d, J = 7.6 Hz). LC/MS(RT) = 1.79 LC/MS(MS) = 387.15 |
| I-039 | 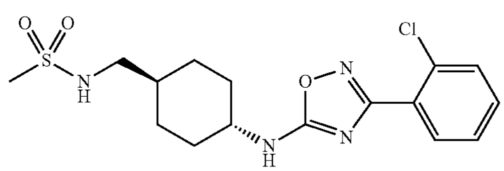 | 1H-NMR (DMSO-d6) δ: 0.96-1.06 (2H, m), 1.23-1.33 (2H, m), 1.34-1.42 (1H, m), 1.77-1.84 (2H, m), 1.98-2.06 (2H, m), 2.79 (2H, t, J = 6.3 Hz), 2.87 (3H, s), 3.39-3.46 (1H, m), 6.98 (1H, t, J = 6.1 Hz), 7.47 (1H, td, J = 7.5, 1.4 Hz), 7.54 (1H, td, J = 7.7, 1.9 Hz), 7.61 (1H, dd, J = 8.1, 1.5 Hz), 7.79 (1H, dd, J = 7.6, 1.5 Hz), 8.47 (1H, d, J = 7.6 Hz). |
| I-040 | 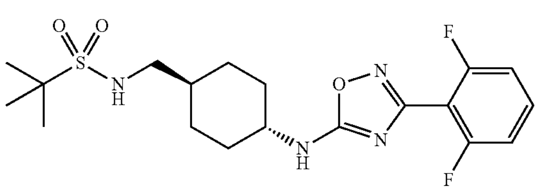 [SMILES: CC(C)(C)S(=O)(=O)NC[C@H]1CC[C@H](Nc2nc(-c3c(F)cccc3F)no2)CC1] | 1H-NMR (DMSO-d6) δ: 0.93-1.03 (2H, m), 1.26-1.39 (13H, m), 1.77-1.85 (2H, m), 1.97-2.05 (2H, m), 2.87 (2H, t, J = 6.3 Hz), 3.36-3.45 (1H, m), 6.86 (1H, t, J = 5.8 Hz), 7.28 (2H, t, J = 8.4 Hz), 7.62-7.69 (1H, m), 8.58 (1H, d, J = 7.6 Hz). LC/MS(RT) = 2.01 LC/MS(MS) = 429.2 |
| I-041 | 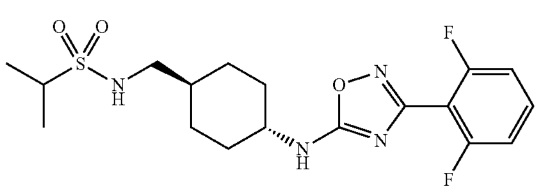 [SMILES: CC(C)S(=O)(=O)NC[C@H]1CC[C@H](Nc2nc(-c3c(F)cccc3F)no2)CC1] | 1H-NMR (DMSO-d6) δ: 0.93-1.03 (2H, m), 1.21 (6H, d, J = 6.6 Hz), 1.22-1.40 (3H, m), 3.10-3.17 (1H, m), 3.37-3.44 (1H, m), 6.98 (1H, t, J = 6.1 Hz), 7.28 (2H t, J = 8.4 Hz), 7.62-7.69 (1H, m), 8.58 (1H, d, J = 7.6 Hz). LC/MS(RT) = 1.87 LC/MS(MS) = 415.2 |

TABLE 11

| No. | Structure | NMR data/LC/MS data (RT, MS) |
|---|---|---|
| I-042 | 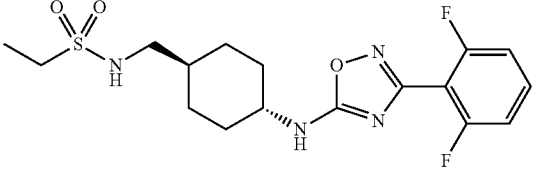 [SMILES: CCS(=O)(=O)NC[C@H]1CC[C@H](Nc2nc(-c3c(F)cccc3F)no2)CC1] | 1H-NMR (DMSO-d6) δ: 0.94-1.04 (2H, m), 1.18 (3H, t, J = 7.4 Hz), 1.22-1.41 (3H, m), 1.77-1.85 (2H, m), 1.97-2.04 (2H, m), 2.76 (2H, t, J = 6.3 Hz), 2.97 (2H, q, J = 7.4 Hz), 3.38-3.44 (1H, m), 7.01 (1H, t, J = 6.1 Hz), 7.28 (2H, t, J = 8.1 Hz), 7.62-7.69 (1H, m), 8.58 (1H, d, J = 7.6 Hz). LC/MS (RT) = 1.75 LC/MS (MS) = 401.2 |
| I-043 | 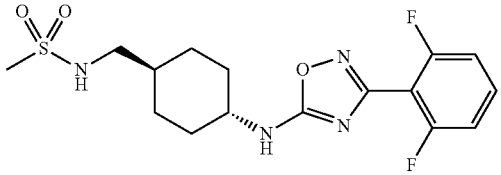 [SMILES: CS(=O)(=O)NC[C@H]1CC[C@H](Nc2nc(-c3c(F)cccc3F)no2)CC1] | 1H-NMR (DMSO-d6) δ: 0.95-1.05 (2H, m), 1.22-1.33 (2H, m), 1.34-1.41 (1H, m), 1.77-1.84 (2H, m), 1.97-2.04 (2H, m), 2.78 (2H, t, J = 6.3 Hz), 2.87 (3H, s), 3.37-3.45 (1H, m), 6.98 (1H, t, J = 6.1 Hz), 7.28 (2H, t, J = 8.4 Hz), 7.62-7.69 (1H, m), 8.58 (1H, d, J = 7.6 Hz). LC/MS (RT) = 1.64 LC/MS (MS) = 387.15 |
| I-044 | 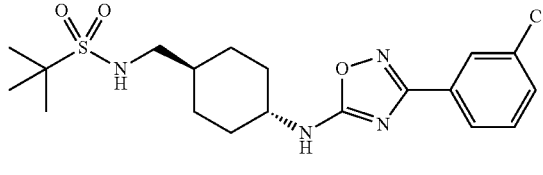 | 1H-NMR (DMSO-d6) δ: 0.98-1.06 (2H, m), 1.24-1.37 (13H, m), 1.82 (2H, d, J = 11.7 Hz), 2.03 (2H, d, J = 10.7 Hz), 2.89 (2H, t, J = 6.3 Hz), 3.48-3.50 (1H, m), 6.87 (1H, t, J = 5.6 Hz), 7.77 (1H, t, J = 7.9 Hz), 7.93 (1H, d, J = 8.1 Hz), 8.12 (1H, s), 8.19 (1H, d, J = 8.1 Hz), 8.54 (1H, d, J = 8.1 Hz). LC/MS (RT) = 2.44 LC/MS (MS) = 461.20 |
| I-045 | 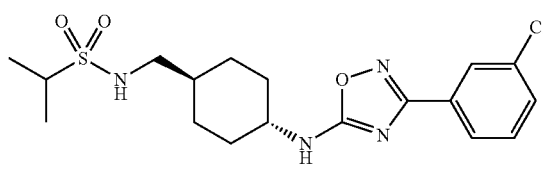 | 1H-NMR (DMSO-d6) δ: 0.99-1.07 (2H, m), 1.26-1.32 (9H, m), 1.82 (2H, d, J = 11.2 Hz), 2.03 (2H, d, J = 9.6 Hz), 2.81 (2H, t, J = 6.3 Hz), 3.11-3.18 (1H, m), 3.49-3.50 (1H, m), 6.98 (1H, t, J = 6.1 Hz), 7.77 (1H, t, J = 7.6 Hz), 7.92 (1H, d, J = 7.6 Hz), 8.12 (1H, s), 8.19 (1H, d, J = 7.6 Hz), 8.54 (1H, d, J = 7.6 Hz). LC/MS (RT) = 2.29 LC/MS (MS) = 447.35 |

TABLE 12

| No. | Structure | NMR data/LC/MS data (RT, MS) |
|---|---|---|
| I-046 | 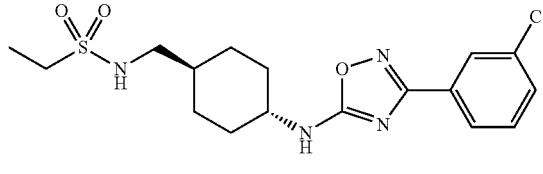 | 1H-NMR (DMSO-d6) δ: 0.99-1.06 (2H, m), 1.21-1.34 (6H, m), 1.82 (2H, d, J = 11.2 Hz), 2.02 (2H, d, J = 10.1 Hz), 2.78 (2H, t, J = 6.3 Hz), 2.98 (2H, q, J = 7.3 Hz), 3.49 (1H, d, J = 7.1 Hz), 7.02 (1H, t, J = 6.1 Hz), 7.77 (1H, t, J = 7.9 Hz), 7.92 (1H, d, J = 7.6 Hz), 8.12 (1H, s), 8.19 (1H, d, J = 7.6 Hz), 8.54 (1H, d, J = 8.1 Hz). LC/MS (RT) = 2.21 LC/MS (MS) = 433.15 |

TABLE 12-continued

| No. | Structure | NMR data/LC/MS data (RT, MS) |
|---|---|---|
| I-047 | 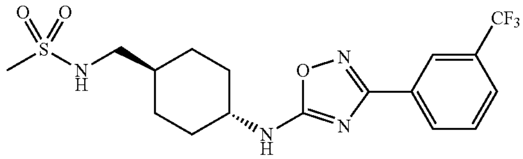 [SMILES: CS(=O)(=O)NC[C@H]1CC[C@H](Nc2nc(-c3cccc(C(F)(F)F)c3)no2)CC1] | 1H-NMR (DMSO-d6) δ: 0.98-1.06 (2H, m), 1.29-1.35 (3H, m), 1.82 (2H, d, J = 11.7 Hz), 2.03 (2H, d, J = 9.6 Hz), 2.80 (2H, t, J = 6.6 Hz), 2.88 (3H, d, J = 5.1 Hz), 3.49 (1H, t, J = 5.6 Hz), 6.99 (1H, t, J = 6.1 Hz), 7.77 (1H, t, J = 7.9 Hz), 7.92 (1H, d, J = 7.6 Hz), 8.12 (1H, s), 8.19 (1H, d, J = 7.6 Hz), 8.55 (1H, d, J = 8.1 Hz).<br>LC/MS (RT) = 2.09<br>LC/MS (MS) = 419.20 |
| I-048 | 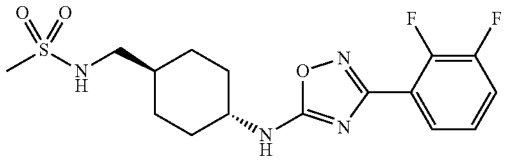 [SMILES: CS(=O)(=O)NC[C@H]1CC[C@H](Nc2nc(-c3cccc(F)c3F)no2)CC1] | 1H-NMR (DMSO-d6) δ: 1.01-1.05 (2H, m), 1.23-1.41 (3H, m), 1.80-1.83 (2H, m), 2.02-2.03 (2H, m), 2.80 (2H, t, J = 6.3 Hz), 2.88 (3H, s), 3.44-3.47 (1H, m), 6.99 (1H, t, J = 5.8 Hz), 7.34-7.39 (1H, m), 7.61-7.64 (1H, m), 7.72-7.74 (1H, m), 8.56 (1H, d, J = 7.6 Hz). |
| I-049 | 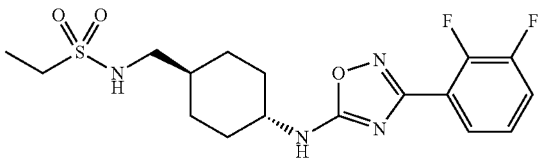 [SMILES: CCS(=O)(=O)NC[C@H]1CC[C@H](Nc2nc(-c3cccc(F)c3F)no2)CC1] | 1H-NMR (DMSO-d6) δ: 1.02-1.05 (2H, m), 1.17-1.39 (6H, m), 1.80-1.83 (2H, m), 2.01-2.04 (2H, m), 2.78 (2H, t, J = 6.3 Hz), 2.98 (2H, q, J = 7.4 Hz), 3.43-3.47 (1H, m), 7.02 (1H, t, J = 6.1 Hz), 7.36-7.38 (1H, m), 7.61-7.64 (1H, m), 7.72-7.74 (1H, m), 8.56 (1H, d, J = 7.6 Hz). |

TABLE 13

| No. | Structure | NMR data/LC/MS data (RT, MS) |
|---|---|---|
| I-050 | 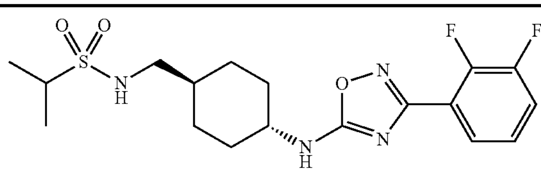 | 1H-NMR (DMSO-d6) δ: 0.97-1.04 (2H, m), 1.23-1.35 (9H, m), 1.80-1.83 (2H, m), 2.00-2.03 (2H, m), 2.81 (2H, t, J = 6.3 Hz), 3.11-3.18 (1H, m), 3.44-3.46 (1H, m), 6.98 (1H, t, J = 6.1 Hz), 7.35-7.37 (1H, m), 7.60-7.65 (1H, m), 7.72-7.74 (1H, m), 8.55 (1H, d, J = 7.6 Hz). |
| I-051 | 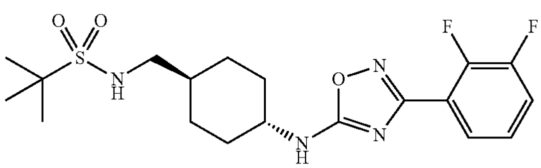 [SMILES: CC(C)(C)S(=O)(=O)NC[C@H]1CC[C@H](Nc2nc(-c3cccc(F)c3F)no2)CC1] | 1H-NMR (DMSO-d6) δ: 0.96-1.06 (2H, m), 1.23-1.37 (13H, m), 1.81-1.83 (2H, m), 2.00-2.03 (2H, m), 2.89 (2H, t, J = 6.3 Hz), 3.43-3.47 (1H, m), 6.87 (1H, t, J = 5.8 Hz), 7.33-7.39 (1H, m), 7.61-7.64 (1H, m), 7.17-7.75 (1H, m), 8.55 (1H, d, J = 7.6 Hz). |
| I-052 | 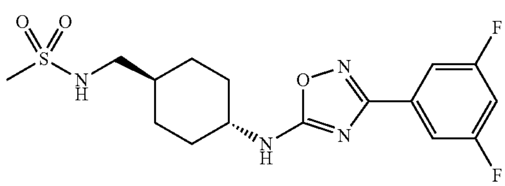 [SMILES: CS(=O)(=O)NC[C@H]1CC[C@H](Nc2nc(-c3cc(F)cc(F)c3)no2)CC1] | 1H-NMR (DMSO-d6) δ: 1.02-1.07 (2H, m), 1.23-1.40 (3H, m), 1.80-1.83 (2H, m), 2.00-2.02 (2H, m), 2.80 (2H, t, J = 6.3 Hz), 2.88 (3H, s), 3.45-3.49 (1H, m), 6.99 (1H, t, J = 6.1 Hz), 7.46-7.50 (3H, m), 8.57 (1H, d, J = 7.6 Hz). |
| I-053 | 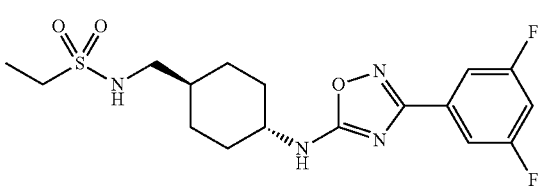 [SMILES: CCS(=O)(=O)NC[C@H]1CC[C@H](Nc2nc(-c3cc(F)cc(F)c3)no2)CC1] | 1H-NMR (DMSO-d6) δ: 1.02-1.05 (2H, m), 1.17-1.29 (6H, m), 1.80-1.84 (2H, m), 2.00-2.02 (2H, m), 2.78 (2H, t, J = 6.3 Hz), 2.98 (2H, q, J = 7.3 Hz), 3.46-3.48 (1H, m), 7.02 (1H, t, J = 5.8 Hz), 7.46-7.50 (3H, m), 8.57 (1H, d, J = 8.1 Hz). |

TABLE 13-continued

| No. | Structure | NMR data/LC/MS data (RT, MS) |
|---|---|---|
| I-054 | 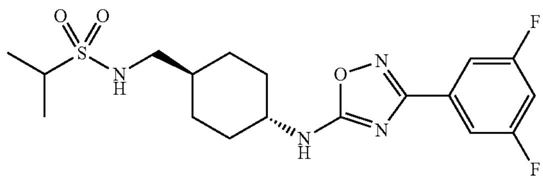 [SMILES: CC(C)S(=O)(=O)NC[C@H]1CC[C@H](Nc2nc(-c3cc(F)cc(F)c3)no2)CC1] | 1H-NMR (DMSO-d6) δ: 1.00-1.05 (2H, m), 1.25-1.32 (9H, m), 1.81-1.83 (2H, m), 2.00-2.02 (2H, m), 2.81 (2H, t, J = 6.3 Hz), 3.14-3.16 (1H, m), 3.45-3.47 (1H, m), 6.98 (1H, t, J = 6.1 Hz), 7.46-7.50 (3H, m), 8.57 (1H, d, J = 7.6 Hz). |

TABLE 14

| No. | Structure | NMR data/LC/MS data (RT, MS) |
|---|---|---|
| I-055 | 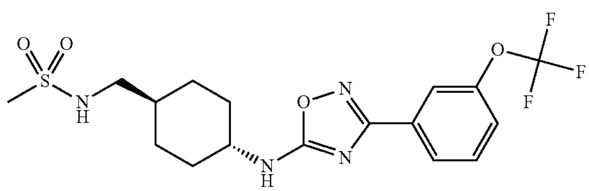 [SMILES: CS(=O)(=O)NC[C@H]1CC[C@H](Nc2nc(-c3cccc(OC(F)(F)F)c3)no2)CC1] | 1H-NMR (DMSO-d6) δ: 0.98-1.07 (2H, m), 1.24-1.39 (3H, m), 1.78-1.82 (2H, m), 1.98-2.05 (2H, m), 2.78-2.82 (2H, m), 2.88 (3H, s), 3.42-3.50 (1H, m), 6.98 (1.0H, s), 7.56 (1H, d, J = 8.1 Hz), 7.67 (1H, t, J = 7.8 Hz), 7.76 (1H, s), 7.92 (1H, d, J = 7.8 Hz), 8.53 (1H, d, J = 8.1 Hz). |
| I-056 | 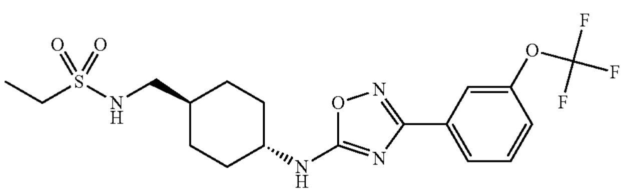 [SMILES: CCS(=O)(=O)NC[C@H]1CC[C@H](Nc2nc(-c3cccc(OC(F)(F)F)c3)no2)CC1] | 1H-NMR (DMSO-d6) δ: 0.98-1.10 (2H, m), 1.15-1.45 (6H, m), 1.77-1.85 (2H, m), 1.98-2.07 (2H, m), 2.75-2.82 (2H, m), 2.95-3.02 (2H, m), 3.42-3.52 (1H, m), 7.02 (1H, s), 7.57 (1H, d, J = 7.1 Hz), 7.67 (1H, t, J = 7.9 Hz), 7.76 (1H, s), 7.92 (1H, d, J = 7.6 Hz), 8.53 (1H, d, J = 7.1 Hz). |
| I-057 | 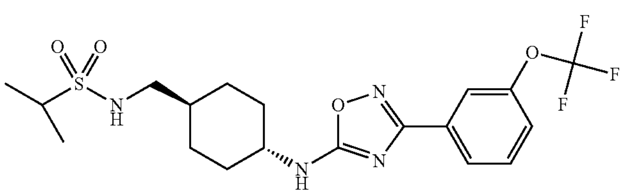 [SMILES: CC(C)S(=O)(=O)NC[C@H]1CC[C@H](Nc2nc(-c3cccc(OC(F)(F)F)c3)no2)CC1] | 1H-NMR (DMSO-d6) δ: 0.98-1.05 (2H, m), 1.19-1.42 (9H, m), 1.78-1.85 (2H, m), 1.98-2.05 (2H, m), 2.81 (2H, t, J = 6.3 Hz), 3.11-3.18 (1H, m), 3.40-3.52 (1H, m), 6.98 (1H, t, J = 6.1 Hz), 7.56 (1H, d, J = 6.6 Hz), 7.67 (1H, t, J = 8.1 Hz), 7.76 (1H, s), 7.92 (1H, d, J = 7.6 Hz), 8.53 (1H, d, J = 7.6 Hz). |
| I-058 | 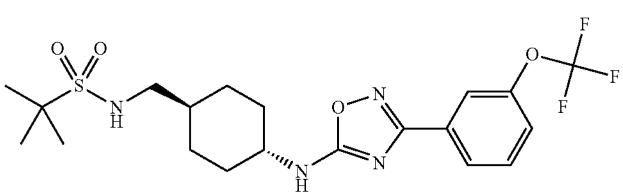 [SMILES: CC(C)(C)S(=O)(=O)NC[C@H]1CC[C@H](Nc2nc(-c3cccc(OC(F)(F)F)c3)no2)CC1] | 1H-NMR (DMSO-d6) δ: 0.97-1.10 (2H, m), 1.20-1.42 (12H, m), 1.78-1.85 (2.1H, d, J = 12.7 Hz), 1.98-2.05 (2H, m), 2.89 (2H, t, J = 6.3 Hz), 3.47 (1H, d, J = 7.6 Hz), 6.87 (1H, t, J = 5.8 Hz), 7.56 (1H, d, J = 8.1 Hz), 7.67 (1H, t, J = 8.1 Hz), 7.76 (1H, s), 7.92 (1H, d, J = 8.1 Hz), 8.53 (1H, d, J = 7.6 Hz). |

TABLE 15

| No. | Structure | NMR data/LC/MS data (RT, MS) |
|---|---|---|
| I-059 | 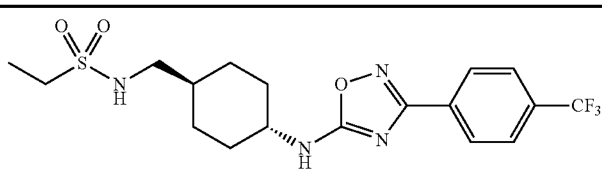 | 1H-NMR (DMSO-d6) δ: 0.98-1.07 (2H, m), 1.19 (3H, t, J = 7.3 Hz), 1.23-1.42 (3H, m), 1.79-1.85 (2H, m), 1.99-2.06 (2H, m), 2.77-2.80 (2H, m), 2.98 (2H, q, J = 7.3 Hz), 3.42-3.53 (1H, m), 7.00-7.03 (1H, m), 7.88 (2H, d, J = 8.1 Hz), 8.10 (2H, d, J = 8.1 Hz), 8.54 (1H, d, J = 8.1 Hz). |

TABLE 15-continued

| No. | Structure | NMR data/LC/MS data (RT, MS) |
|---|---|---|
| I-060 | 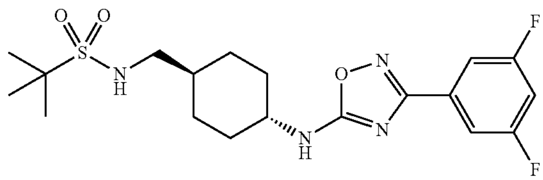 [SMILES: CC(C)(C)S(=O)(=O)NC[C@H]1CC[C@H](Nc2nc(-c3cc(F)cc(F)c3)no2)CC1] | 1H-NMR (DMSO-d6) δ: 0.94-1.06 (2H, m), 1.22-1.39 (12H, m), 1.81-1.84 (2H, m), 2.00-2.02 (2H, m), 2.89 (2H, t, J = 6.3 Hz), 3.45-3.47 (1H, m), 6.87 (1H, t, J = 5.8 Hz), 7.44-7.53 (3H, m), 8.56 (1H, d, J = 8.1 Hz). |
| I-061 | 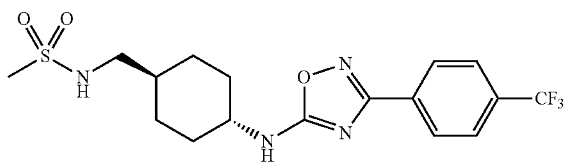 [SMILES: CS(=O)(=O)NC[C@H]1CC[C@H](Nc2nc(-c3ccc(C(F)(F)F)cc3)no2)CC1] | 1H-NMR (DMSO-d6) δ: 0.98-1.09 (2H, m), 1.23-1.44 (3H, m), 1.78-1.85 (2H, m), 1.99-2.06 (2H, m), 2.79-2.82 (2H, m), 2.88 (3H, s), 3.43-3.52 (1H, ,m), 6.99 (1H, t, J = 6.1 Hz), 7.88 (2H, d, J = 8.1 Hz), 8.10 (2H, d, J = 8.1 Hz), 8.55 (1H, d, J = 7.6 Hz). LC/MS (RT) = 2.10 LC/MS (MS) = 419.15 |
| I-062 | 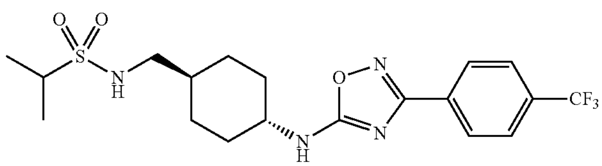 | 1H-NMR (DMSO-d6) δ: 0.97-1.07 (2H, m), 1.21-1.41 (9H, m), 1.79-1.86 (2H, m), 1.99-2.06 (2H, m), 2.79-2.83 (2H, m), 3.12-3.18 (1H, m), 3.44-3.52 (1H, m), 6.97-7.00 (1H, m), 7.88 (2H, d, J = 8.6 Hz), 8.10 (2H, d, J = 8.1 Hz), 8.54 (1H, d, J = 7.6 Hz). LC/MS (RT) = 2.30 LC/MS (MS) = 447.00 |

TABLE 16

| No. | Structure | NMR data/LC/MS data (RT, MS) |
|---|---|---|
| I-063 | 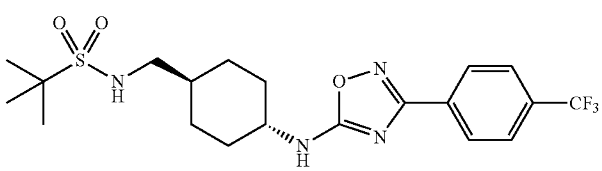 [SMILES: CC(C)(C)S(=O)(=O)NC[C@H]1CC[C@H](Nc2nc(-c3ccc(C(F)(F)F)cc3)no2)CC1] | 1H-NMR (DMSO-d6) δ: 0.97-1.07 (2H, m), 1.22-1.40 (12H, m), 1.79-1.85 (2H, m), 1.99-2.07 (2H, m), 2.88-2.91 (2H, m), 3.45-3.51 (1H, m), 6.87 (1H, t, J = 6.1 Hz), 7.88 (2H, d, J = 8.1 Hz), 8.10 (2H, d, J = 8.1 Hz), 8.54 (1H, d, J = 7.6 Hz). LC/MS (RT) = 2.42 LC/MS (MS) = 461.25 |
| I-064 | 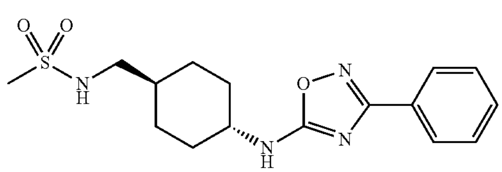 [SMILES: CS(=O)(=O)NC[C@H]1CC[C@H](Nc2nc(-c3ccccc3)no2)CC1] | 1H-NMR (DMSO-d6) δ: 1.01-1.07 (2H, m), 1.26-1.37 (3H, m), 1.80-1.83 (2H, m), 2.01-2.04 (2H, m), 2.80 (2H, t, J = 6.3 Hz), 2.88 (3H, s), 3.44-3.48 (1H, m), 6.98 (1H, t, J = 6.1 Hz), 7.47-7.53 (3H, m), 7.88-7.90 (2H, m), 8.40 (1H, d, J = 8.1 Hz). |
| I-065 | 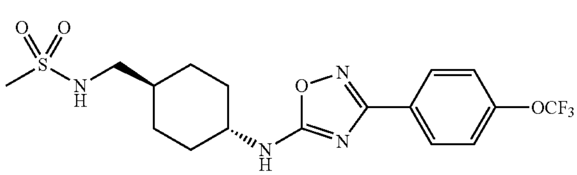 [SMILES: CS(=O)(=O)NC[C@H]1CC[C@H](Nc2nc(-c3ccc(OC(F)(F)F)cc3)no2)CC1] | 1H-NMR (DMSO-d6) δ: 0.98-1.05 (2H, m), 1.24-1.39 (3H, m), 1.81 (2H, d, J = 12.7 Hz), 2.02 (2H, d, J = 9.6 Hz), 2.80 (2H, t, J = 6.6 Hz), 2.88 (3H, s), 3.45-3.47 (1H, m), 6.99 (1H, t, J = 6.1 Hz), 7.50 (2H, d, J = 8.1 Hz), 8.01 (2H, t, J = 4.6 Hz), 8.49 (1H, d, J = 8.1 Hz). LC/MS (RT) = 2.17 LC/MS (MS) = 435.15 |

TABLE 16-continued

| No. | Structure | NMR data/LC/MS data (RT, MS) |
|---|---|---|
| I-066 | 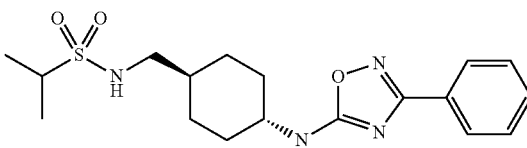 | 1H-NMR (DMSO-d6) δ: 0.95-1.03 (2H, m), 1.24-1.34 (9H, m), 1.82 (2H, d, J = 12.2 Hz), 2.02 (2H, d, J = 10.1 Hz), 2.81 (2H, t, J = 6.3 Hz), 3.11-3.18 (1H, m), 3.45-3.47 (1H, m), 6.98 (1H, t, J = 6.1 Hz), 7.50 (2H, d, J = 8.1 Hz), 8.01 (2H, d, J = 9.1 Hz), 8.48 (1H, d, J = 7.6 Hz). LC/MS (RT) = 2.36 LC/MS (MS) = 463.20 |

TABLE 17

| No. | Structure | NMR data/LC/MS data (RT, MS) |
|---|---|---|
| I-067 | 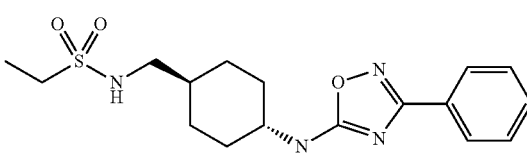 | 1H-NMR (DMSO-d6) δ: 0.96-1.05 (2H, m), 1.19 (3H, t, J = 7.4 Hz), 1.23-1.38 (3H, m), 1.82 (2H, d, J = 11.7 Hz), 2.02 (2H, d, J = 10.1 Hz), 2.78 (2H, t, J = 6.6 Hz), 2.98 (2H, q, J = 7.4 Hz), 3.45-3.47 (1H, m), 7.02 (1H, t, J = 6.1 Hz), 7.50 (2H, d, J = 8.1 Hz), 8.01 (2H, t, J = 4.3 Hz), 8.48 (1H, d, J = 8.1 Hz). LC/MS (RT) = 2.26 LC/MS (MS) = 449.20 |
| I-068 | 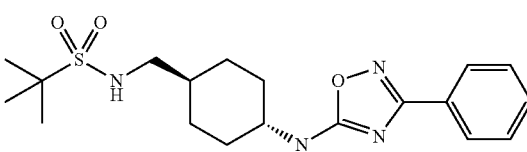 | 1H-NMR (DMSO-d6) δ: 0.96-1.06 (2H, m), 1.25-1.29 (12H, m), 1.82 (2H, d, J = 12.2 Hz), 2.03 (2H, d, J = 10.1 Hz), 2.89 (2H, t, J = 6.1 Hz), 3.46-3.48 (1H, m), 6.87 (1H, t, J = 5.6 Hz), 7.50 (2H, d, J = 8.1 Hz), 8.01 (2H, d, J = 8.6 Hz), 8.48 (1H, d, J = 8.1 Hz). LC/MS (RT) = 2.45 LC/MS (MS) = 477.50 |
| I-069 | 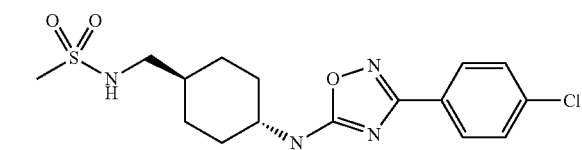 | 1H-NMR (DMSO-d6) δ: 0.95-1.05 (2H, m), 1.26-1.36 (3H, m), 1.81 (2H, d, J = 13.2 Hz), 2.02 (2H, d, J = 10.1 Hz), 2.80 (2H, t, J = 6.6 Hz), 2.88 (3H, s), 3.45-3.47 (1H, m), 6.99 (1H, t, J = 6.1 Hz), 7.57 (2H, d, J = 4.3 Hz), 7.89 (2H, d, J = 4.3 Hz), 8.47 (1H, d, J = 8.1 Hz). LC/MS (RT) = 2.00 LC/MS (MS) = 384.95 |
| I-070 | 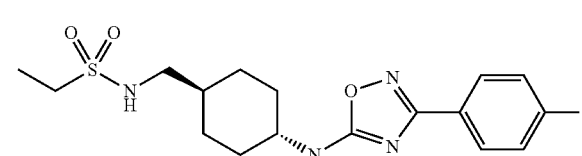 | 1H-NMR (DMSO-d6) δ: 0.96-1.03 (2H, m), 1.19 (3H, t, J = 7.4 Hz), 1.23-1.38 (3H, m), 1.82 (2H, d, J = 11.7 Hz), 2.02 (2H, d, J = 10.1 Hz), 2.78 (2H, t, J = 6.3 Hz), 2.98 (2H, q, J = 7.4 Hz), 3.45-3.47 (1H, m), 7.02 (1H, t, J = 5.8 Hz), 7.57 (2H, d, J = 8.6 Hz), 7.89 (2H, t, J = 4.3 Hz), 8.46 (1H, d, J = 7.6 Hz). LC/MS (RT) = 2.10 LC/MS (MS) = 398.95 |

TABLE 18

| No. | Structure | NMR data/LC/MS data (RT, MS) |
|---|---|---|
| I-071 | 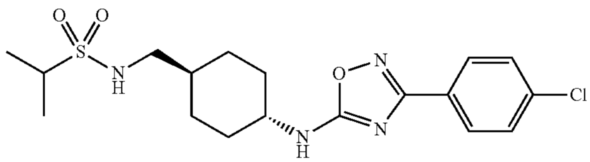 [SMILES: CC(C)S(=O)(=O)NC[C@H]1CC[C@H](Nc2nc(-c3ccc(Cl)cc3)no2)CC1] | 1H-NMR (DMSO-d6) δ: 0.94-1.03 (2H, m), 1.24-1.34 (9H, m), 1.82 (2H, d, J = 13.2 Hz), 2.02 (2H, d, J = 10.7 Hz), 2.81 (2H, t, J = 6.3 Hz), 3.11-3.18 (1H, m), 3.45-3.46 (1H, m), 6.98 (1H, t, J = 5.8 Hz), 7.57 (2H, d, J = 8.6 Hz), 7.89 (2H, d, J = 8.6 Hz), 8.46 (1H, d, J = 7.6 Hz).<br>LC/MS (RT) = 2.22<br>LC/MS (MS) = 413.00 |
| I-072 | 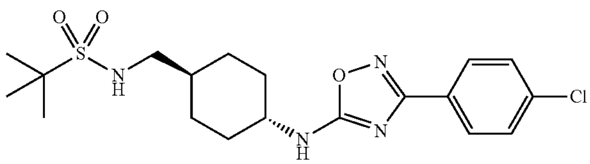 [SMILES: CC(C)(C)S(=O)(=O)NC[C@H]1CC[C@H](Nc2nc(-c3ccc(Cl)cc3)no2)CC1] | 1H-NMR (DMSO-d6) δ: 0.96-1.03 (2H, m), 1.25-1.34 (12H, m), 1.82 (2H, d, J = 11.7 Hz), 2.02 (2H, d, J = 9.6 Hz), 2.89 (2H, t, J = 6.1 Hz), 3.45-3.47 (1H, m), 6.87 (1H, t, J = 5.8 Hz), 7.56-7.59 (2H, m), 7.88-7.91 (2H, m), 8.46 (1H, d, J = 8.1 Hz).<br>LC/MS (RT) = 2.38<br>LC/MS (MS) = 427.20 |
| I-073 | 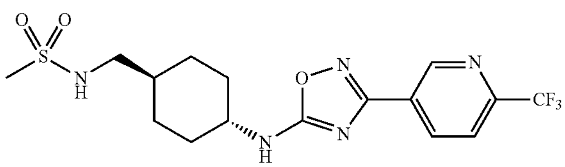 [SMILES: CS(=O)(=O)NC[C@H]1CC[C@H](Nc2nc(-c3ccc(C(F)(F)F)nc3)no2)CC1] | 1H-NMR (DMSO-d6) δ: 0.96-1.05 (2H, m), 1.25-1.40 (3H, m), 1.82 (2H, d, J = 12.7 Hz), 2.03 (2H, d, J = 9.6 Hz), 2.80 (2H, t, J = 6.6 Hz), 2.88 (3H, s), 3.48-3.52 (1H, m), 6.99 (1H, t, J = 6.3 Hz), 8.06 (1H, d, J = 8.1 Hz), 8.51 (1H, dd, J = 8.4, 1.8 Hz), 8.69 (1H, d, J = 7.6 Hz), 9.21 (1H, s).<br>LC/MS (RT) = 1.89<br>LC/MS (MS) = 420.15 |
| I-074 | 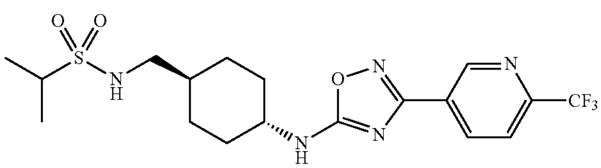 [SMILES: CC(C)S(=O)(=O)NC[C@H]1CC[C@H](Nc2nc(-c3ccc(C(F)(F)F)nc3)no2)CC1] | 1H-NMR (DMSO-d6) δ: 0.96-1.03 (2H, m), 1.24-1.35 (9H, m), 1.82 (2H, d, J = 11.2 Hz), 2.03 (2H, d, J = 10.1 Hz), 2.81 (2H, t, J = 6.3 Hz), 3.12-3.18 (1H, m), 3.48-3.50 (1H, m), 6.99 (1H, t, J = 6.1 Hz), 8.06 (1H, d, J = 8.1 Hz), 8.51 (1H, dd, J = 9.6, 4.8 Hz), 8.68 (1H, d, J = 7.6 Hz), 9.21 (1H, s).<br>LC/MS (RT) = 2.08<br>LC/MS (MS) = 448.00 |

TABLE 19

| No. | Structure | NMR data/LC/MS data (RT, MS) |
|---|---|---|
| I-075 | 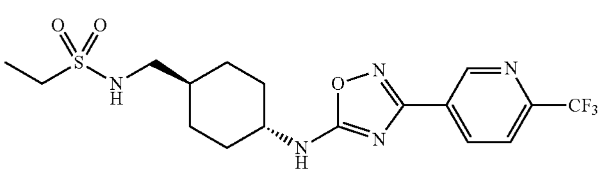 [SMILES: CCS(=O)(=O)NC[C@H]1CC[C@H](Nc2nc(-c3ccc(C(F)(F)F)nc3)no2)CC1] | 1H-NMR (DMSO-d6) δ: 0.99-1.03 (2H, m), 1.19 (3H, t, J = 7.4 Hz), 1.25-1.39 (3H, m), 1.83 (2H, d, J = 12.2 Hz), 2.03 (2H, d, J = 10.1 Hz), 2.79 (2H, t, J = 6.3 Hz), 2.98 (2H, q, J = 7.4 Hz), 3.49-3.51 (1H, m), 7.02 (1H, t, J = 6.1 Hz), 8.06 (1H, d, J = 8.6 Hz), 8.51 (1H, dd, J = 4.8, 2.4 Hz), 8.68 (1H, d, J = 7.6 Hz), 9.21 (1H, s).<br>LC/MS (RT) = 1.97<br>LC/MS (MS) = 434.20 |

TABLE 19-continued

| No. | Structure | NMR data/LC/MS data (RT, MS) |
|---|---|---|
| I-076 | 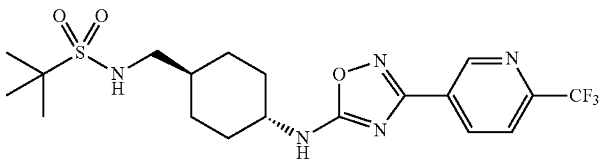 [SMILES: CC(C)(C)S(=O)(=O)NC[C@H]1CC[C@H](Nc2nc(-c3ccc(C(F)(F)F)nc3)no2)CC1] | 1H-NMR (DMSO-d6) δ: 0.97-1.03 (2H, m), 1.29-1.32 (12H, m), 1.83 (2H, d, J = 11.7 Hz), 2.05 (2H, d, J = 10.4 Hz), 2.89 (2H, t, J = 6.3 Hz), 3.49-3.51 (1H, m), 6.88 (1H, t, J = 5.8 Hz), 8.06 (1H, d, J = 8.1 Hz), 8.51 (1H, dd, J = 8.1, 4.1 Hz), 8.68 (1H, d, J = 7.6 Hz), 9.20 (1H, s). LC/MS (RT) = 2.20 LC/MS (MS) = 462.05 |
| I-077 | 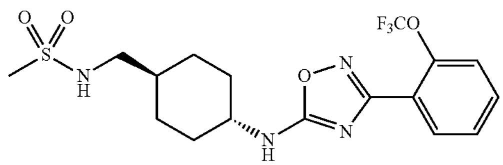 [SMILES: CS(=O)(=O)NC[C@H]1CC[C@H](Nc2nc(-c3ccccc3OC(F)(F)F)no2)CC1] | 1H-NMR (DMSO-d6) δ: 0.99-1.06 (2H, m), 1.26-1.39 (3H, m), 1.81-1.82 (2H, m), 2.02-2.03 (2H, m), 2.80 (2H, t, J = 6.3 Hz), 2.88 (3H, s), 3.44-3.45 (1H, m), 6.98 (1H, t, J = 6.1 Hz), 7.52-7.58 (2H, m), 7.66-7.68 (1H, m), 7.98-8.00 (1H, m), 8.48 (1H, d, J = 7.6 Hz). |
| I-078 | 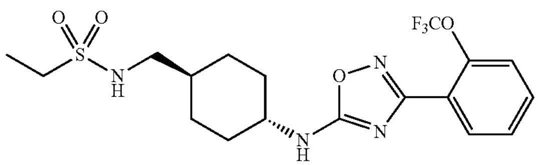 [SMILES: CCS(=O)(=O)NC[C@H]1CC[C@H](Nc2nc(-c3ccccc3OC(F)(F)F)no2)CC1] | 1H-NMR (DMSO-d6) δ: 1.00-1.04 (2H, m), 1.21-1.33 (6H, m), 1.81-1.83 (2H, m), 2.02-2.04 (2H, m), 2.78 (2H, t, J = 6.3 Hz), 2.98 (2H, q, J = 7.4 Hz), 3.42-3.46 (1H, m), 7.02 (1H, t, J = 6.1 Hz), 7.52-7.57 (2H, m), 7.66-7.68 (1H, m), 7.98-8.00 (1H, m), 8.48 (1H, d, J = 7.6 Hz). |

TABLE 20

| No. | Structure | NMR data/LC/MS data (RT, MS) |
|---|---|---|
| I-079 | 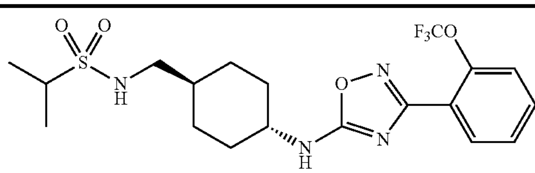 | 1H-NMR (DMSO-d6) δ: 0.99-1.04 (2H, m), 1.20-1.38 (9H, m), 1.80-1.83 (2H, m), 2.02-2.03 (2H, m), 2.80 (2H, t, J = 6.3 Hz), 3.12-3.15 (1H, m), 3.42-3.45 (1H, m), 6.98 (1H, t, J = 6.1 Hz), 7.53-7.57 (2H, m), 7.66-7.68 (1H, m), 7.98-8.00 (1H, m), 8.48 (1H, d, J = 7.6 Hz). |
| I-080 | 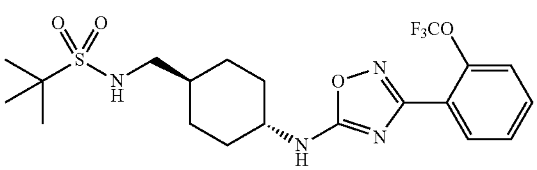 [SMILES: CC(C)(C)S(=O)(=O)NC[C@H]1CC[C@H](Nc2nc(-c3ccccc3OC(F)(F)F)no2)CC1] | 1H-NMR (DMSO-d6) δ: 0.98-1.04 (2H, m), 1.22-1.37 (12H, m), 1.81-1.83 (2H, m), 2.02-2.04 (2H, m), 2.89 (2H, t, J = 6.3 Hz), 3.42-3.46 (1H, m), 6.87 (1H, t, J = 5.8 Hz), 7.52-7.57 (2H, m), 7.66-7.68 (1H, m), 7.98-8.00 (1H, m), 8.47 (1H, d, J = 7.6 Hz). |
| I-081 | 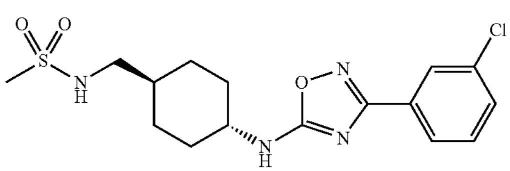 [SMILES: CS(=O)(=O)NC[C@H]1CC[C@H](Nc2nc(-c3cccc(Cl)c3)no2)CC1] | 1H-NMR (DMSO-d6) δ: 1.02-1.06 (2H, m), 1.23-1.41 (3H, m), 1.80-1.83 (2H, m), 1.99-2.04 (2H, m), 2.80 (2H, t, J = 6.3 Hz), 2.88 (3H, s), 3.45-3.49 (1H, m), 6.99 (1H, t, J = 6.1 Hz), 7.53-7.63 (2H, m), 7.84-7.86 (2H, m), 8.50 (1H, d, J = 8.1 Hz). |
| I-082 | 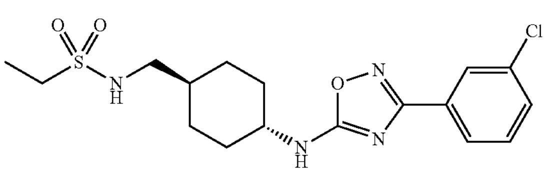 [SMILES: CCS(=O)(=O)NC[C@H]1CC[C@H](Nc2nc(-c3cccc(Cl)c3)no2)CC1] | 1H-NMR (DMSO-d6) δ: 1.03-1.06 (2H, m), 1.22-1.34 (6H, m), 1.80-1.83 (2H, m), 2.00-2.02 (2H, m), 2.78 (2H, t, J = 6.3 Hz), 2.98 (2H, q, J = 7.4 Hz), 3.45-3.49 (1H, m), 7.02 (1H, t, J = 6.1 Hz), 7.53-7.63 (2H, m), 7.84-7.86 (2H, m), 8.50 (1H, d, J = 8.1 Hz). |

TABLE 20-continued

| No. | Structure | NMR data/LC/MS data (RT, MS) |
|---|---|---|
| I-083 | 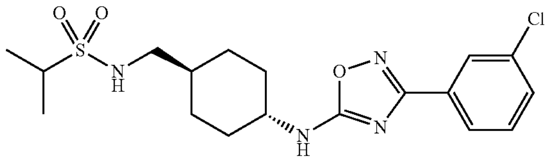 [SMILES: CC(C)S(=O)(=O)NC[C@H]1CC[C@H](Nc2nc(-c3cccc(Cl)c3)no2)CC1] | 1H-NMR (DMSO-d6) δ: 1.02-1.04 (2H, m), 1.21-1.38 (9H, m), 1.80-1.84 (2H, m), 1.99-2.03 (2H, m), 2.81 (2H, t, J = 6.3 Hz), 3.11-3.18 (1H, m), 3.45-3.49 (1H, m), 6.98 (1H, t, J = 5.8 Hz), 7.56-7.60 (2H, m), 7.84-7.86 (2H, m), 8.50 (1H, d, J = 7.6 Hz). |

TABLE 21

| 実施例 No. | 化学構造 | NMRデータ, LC/MSデータ (RT, MS) |
|---|---|---|
| I-084 | | 1H-NMR (DMSO-d6) δ: 0.97-(2H, m), 1.28-1.33 (12H, m), 1.81-1.84 (2H, m), 2.02-2.03 (2H, m), 2.89 (2H, t, J = 6.3 Hz), 3.45-3.49 (1H, m), 6.87 (1H, t, J = 5.8 Hz), 7.53-7.63 (2H, m), 7.84-7.86 (2H, m), 8.50 (1H, d, J = 7.6 Hz). |
| I-085 | | 1H-NMR (DMSO-d6) δ: 0.94-1.06 (2H, m), 1.14-1.27 (11H, m), 1.30-1.40 (1H, m), 1.73-1.82 (2H, m), 1.91-1.99 (2H, m), 2.78 (2H, t, J = 6.3 Hz), 2.87 (3H, s), 6.96 (1H, t, J = 6.1 Hz), 8.08 (1H, d, J = 8.1 Hz). 1H overlap with solvent. |
| I-086 | | 1H-NMR (DMSO-d6) δ: 0.93-1.06 (2H, m), 1.06-1.26 (14H, m), 1.29-1.39 (1H, m), 1.75-1.82 (2H, m), 1.91-1.99 (2H, m), 2.76 (2H, t, J = 6.3 Hz), 2.97 (2H, q, J = 7.3 Hz), 6.99 (1H, t, J = 5.8 Hz), 8.07 (1H, d, J = 7.6 Hz). 1H overlap with solvent. |
| I-087 | | 1H-NMR (DMSO-d6) δ: 0.93-1.06 (2H, m), 1.15-1.25 (17H, m), 1.28-1.39 (1H, m), 1.74-1.83 (2H, m), 1.91-1.99 (2H, m), 2.79 (2H, t, J = 6.3 Hz), 3.09-3.19 (1H, m), 6.96 (1H, t, J = 5.8 Hz), 8.07 (1H, d, J = 7.6 Hz). 1H overlap with solvent |
| I-088 | | 1H-NMR (DMSO-d6) δ: 0.91-1.06 (2H, m), 1.13-1.39 (21H, m), 1.28-1.39 (1H, m), 1.74-1.83 (2H, m), 1.92-1.99 (2H, m), 2.87 (2H, t, J = 6.3 Hz), 6.85 (1H, t, J = 5.8 Hz), 8.07 (1H, d, J = 8.1 Hz). 1H overlap with solvent. |

TABLE 22

| No. | Structure | NMR data/LC/MS data (RT, MS) |
|---|---|---|
| I-089 | 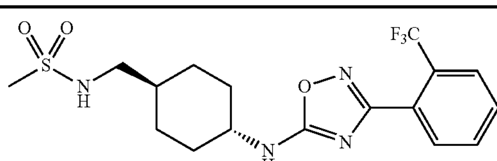 | 1H-NMR (DMSO-d6) δ: 0.97-1.01 (2H, m), 1.23-1.36 (3H, m), 1.80 (2H, d, J = 12.2 Hz), 2.02 (2H, d, J = 10.1 Hz), 2.79 (2H, t, J = 6.3 Hz), 2.87 (3H, s), 3.40-3.41 (1H, m), 6.98 (1H, t, J = 6.1 Hz), 7.74-7.82 (3H, m), 7.90 (1H, d, J = 7.6 Hz), 8.49 (1H, d, J = 7.1 Hz). LC/MS (RT) = 1.85 LC/MS (MS) = 419.15 |

TABLE 22-continued

| No. | Structure | NMR data/LC/MS data (RT, MS) |
|---|---|---|
| I-090 | 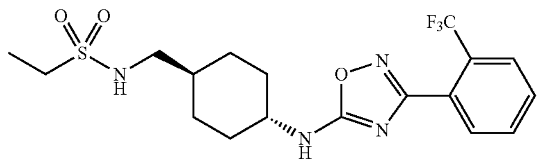 | 1H-NMR (DMSO-d6) δ: 0.96-1.02 (2H, m), 1.18 (3H, t, J = 7.4 Hz), 1.23-1.37 (3H, m), 1.81 (2H, d, J = 11.2 Hz), 2.02 (2H, d, J = 10.1 Hz), 2.77 (2H, t, J = 6.3 Hz), 2.97 (2H, q, J = 7.4 Hz), 3.39-3.41 (1H, m), 7.01 (1H, t, J = 6.1 Hz), 7.74-7.82 (3H, m), 7.90 (1H, d, J = 7.6 Hz), 8.49 (1H, d, J = 7.6 Hz). LC/MS (RT) = 1.95 LC/MS (MS) = 433.20 |
| I-091 | 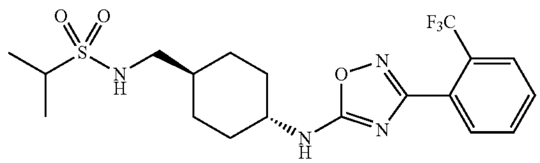 [SMILES: CC(C)S(=O)(=O)NC[C@H]1CC[C@H](Nc2nc(-c3ccccc3C(F)(F)F)no2)CC1] | 1H-NMR (DMSO-d6) δ: 0.96-1.03 (2H, m), 1.25-1.31 (9H, m), 1.81 (2H, d, J = 13.2 Hz), 2.02 (2H, d, J = 10.1 Hz), 2.79 (2H, t, J = 6.3 Hz), 3.10-3.17 (1H, m), 3.40 (1H, d, J = 7.6 Hz), 6.98 (1H, t, J = 6.1 Hz), 7.74-7.82 (3H, m), 7.90 (1H, d, J = 7.6 Hz), 8.49 (1H, d, J = 7.6 Hz). LC/MS (RT) = 2.04 LC/MS (MS) = 447.40 |
| I-092 | 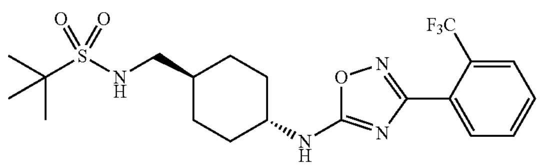 | 1H-NMR (DMSO-d6) δ: 0.96-1.03 (2H, m), 1.25-1.30 (12H, m), 1.81 (2H, d, J = 12.2 Hz), 2.02 (2H, d, J = 9.6 Hz), 2.88 (2H, t, J = 6.3 Hz), 3.39-3.41 (1H, m), 6.87 (1H, t, J = 5.8 Hz), 7.76-7.80 (3H, m), 7.90 (1H, d, J = 8.1 Hz), 8.49 (1H, d, J = 7.6 Hz). LC/MS (RT) = 2.16 LC/MS (MS) = 461.40 |

TABLE 23

| No. | Structure | NMR data/LC/MS data (RT, MS) |
|---|---|---|
| I-093 | 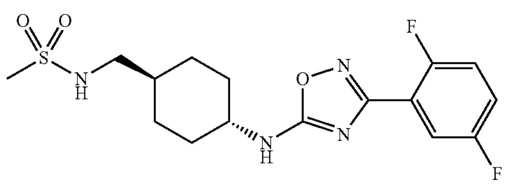 [SMILES: CS(=O)(=O)NC[C@H]1CC[C@H](Nc2nc(-c3cc(F)ccc3F)no2)CC1] | 1H-NMR (DMSO-d6) δ: 1.03-1.06 (2H, m), 1.25-1.36 (3H, m), 1.80-1.82 (2H, m), 2.00-2.02 (2H, m), 2.80 (2H, t, J = 6.3 Hz), 2.88 (3H, s), 3.44-3.46 (1H, m), 6.98 (1H, t, J = 6.1 Hz), 7.45-7.46 (2H, m), 7.63-7.67 (1H, m), 8.55 (1H, d, J = 7.6 Hz). |
| I-094 | 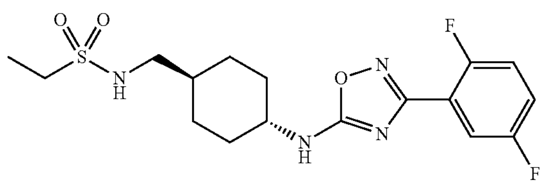 [SMILES: CCS(=O)(=O)NC[C@H]1CC[C@H](Nc2nc(-c3cc(F)ccc3F)no2)CC1] | 1H-NMR (DMSO-d6) δ: 0.99-1.05 (2H, m), 1.17-1.41 (6H, m), 1.80-1.83 (2H, m), 1.99-2.03 (2H, m), 2.78 (2H, t, J = 6.3 Hz), 2.98 (2H, q, J = 7.4 Hz), 3.42-3.49 (1H, m), 7.02 (1H, t, J = 6.1 Hz), 7.45-7.46 (2H, m), 7.63-7.67 (1H, m), 8.55 (1H, d, J = 7.6 Hz). |
| I-095 | 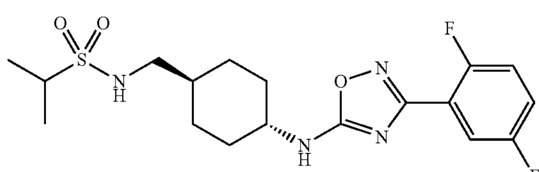 | 1H-NMR (DMSO-d6) δ: 0.99-1.06 (2H, m), 1.24-1.34 (9H, m), 1.81-1.83 (2H, m), 1.99-2.04 (2H, m), 2.80 (2H, t, J = 6.3 Hz), 3.14-3.15 (1H, m), 3.43-3.47 (1H, m), 6.98 (1H, t, J = 6.1 Hz), 7.45-7.46 (2H, m), 7.63-7.67 (1H, m), 8.55 (1H, d, J = 8.1 Hz). |

TABLE 23-continued

| No. | Structure | NMR data/LC/MS data (RT, MS) |
|---|---|---|
| I-096 | 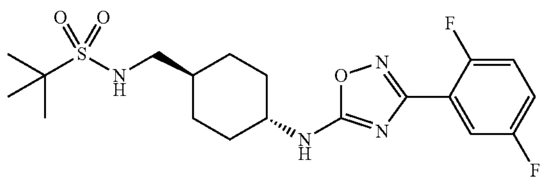 [SMILES: CC(C)(C)S(=O)(=O)NC[C@H]1CC[C@H](Nc2nc(-c3cc(F)ccc3F)no2)CC1] | 1H-NMR (DMSO-d6) δ: 0.98-1.04 (2H, m), 1.22-1.38 (12H, m), 1.80-1.84 (2H, m), 1.99-2.03 (2H, m), 2.89 (2H, t, J = 6.1 Hz), 3.44-3.47 (1H, m), 6.87 (1H, t, J = 5.8 Hz), 7.45-7.46 (2H, m), 7.63-7.67 (1H, m), 8.54 (1H, d, J = 8.1 Hz). |
| I-097 | 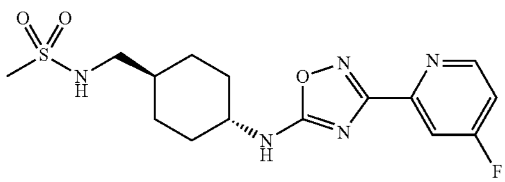 [SMILES: CS(=O)(=O)NC[C@H]1CC[C@H](Nc2nc(-c3cc(F)ccn3)no2)CC1] | 1H-NMR (DMSO-d6) δ: 0.98-1.03 (2H, m), 1.24-1.39 (3H, m), 1.82 (2H, d, J = 12.2 Hz), 2.02 (2H, d, J = 10.1 Hz), 2.80 (2H, t, J = 6.3 Hz), 2.88 (3H, s), 3.46-3.48 (1H, m), 6.99 (1H, t, J = 6.1 Hz), 7.88 (1H, td, J = 8.6, 3.0 Hz), 8.02 (1H, dd, J = 8.6, 4.6 Hz), 8.48 (1H, d, J = 8.1 Hz), 8.70 (1H, d, J = 2.5 Hz). LC/MS (RT) = 1.41 LC/MS (MS) = 370.15 |

TABLE 24

| No. | Structure | NMR data/LC/MS data (RT, MS) |
|---|---|---|
| I-098 | 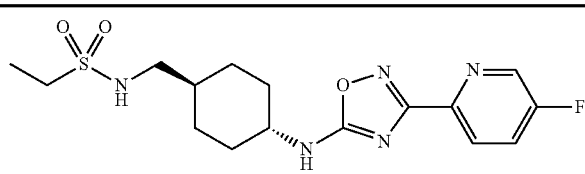 | 1H-NMR (DMSO-d6) δ: 0.96-1.03 (2H, m), 1.19 (3H, t, J = 7.4 Hz), 1.24-1.38 (3H, m), 1.82 (2H, d, J = 11.7 Hz), 2.02 (2H, d, J = 9.6 Hz), 2.78 (2H, t, J = 6.3 Hz), 2.98 (2H, q, J = 7.4 Hz), 3.45-3.47 (1H, m), 7.02 (1H, t, J = 5.8 Hz), 7.88 (1H, td, J = 8.7, 2.70 Hz), 8.02 (1H, dd, J = 8.6, 4.6 Hz), 8.48 (1H, d, J = 7.6 Hz), 8.70 (1H, d, J = 3.0 Hz). LC/MS(RT) = 1.52 LC/MS(MS) = 384.20 |
| I-099 | 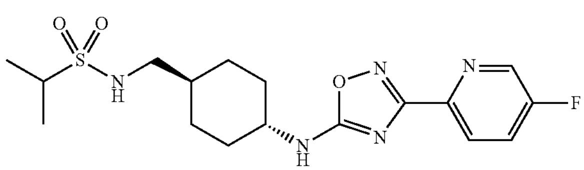 | 1H-NMR (DMSO-d6) δ: 0.96-1.02 (2H, m), 1.24-1.34 (9H, m), 1.82 (2H, d, J = 11.2 Hz), 2.02 (2H, d, J = 10.7 Hz), 2.81 (2H, t, J = 6.3 Hz), 3.11-3.18 (1H, m), 3.46-3.47 (1H, m), 6.99 (1H, t, J = 6.1 Hz), 7.88 (1H, td, J = 8.7, 2.7 Hz), 8.02 (1H, dd, J = 8.6, 4.6 Hz), 8.48 (1H, d, J = 7.6 Hz), 8.70 (1H, d, J = 3.0 Hz). LC/MS(RT) = 1.65 LC/MS(MS) = 398.20 |
| I-100 | 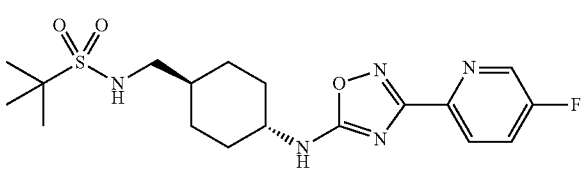 | 1H-NMR (DMSO-d6) δ: 0.97-1.02 (2H, m), 1.25-1.34 (12H, m), 1.82 (2H, d, J = 12.7 Hz), 2.03 (2H, d, J = 10.1 Hz), 2.89 (2H, t, J = 6.1 Hz), 3.46-3.48 (1H, m), 6.88 (1H, t, J = 5.8 Hz), 7.88 (1H, td, J = 8.7, 2.7 Hz), 8.02 (1H, dd, J = 8.6, 4.6 Hz), 8.48 (1H, d, J = 7.6 Hz), 8.70 (1H, d, J = 2.5 Hz). LC/MS(RT) = 1.77 LC/MS(MS) = 412.30 |
| I-101 | 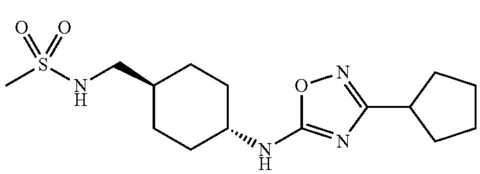 [SMILES: CS(=O)(=O)NC[C@H]1CC[C@H](Nc2nc(C3CCCC3)no2)CC1] | 1H-NMR (DMSO-d6) δ: 0.93-1.04 (2H, m), 1.15-1.27 (2H, m), 1.30-1.41 (1H, m), 1.53-1.73 (6H, m), 1.74-1.81 (2H, m), 1.83-1.99 (4H, m), 2.78 (2H, t, J = 6.6 Hz), 2.87 (3H, s), 2.89-2.96 (1H, m), 6.96 (1H, t, J = 5.8 Hz), 8.09 (1H, d, J = 7.6 Hz). 1H overlap with solvent. |

TABLE 25

| No. | Structure | NMR data/LC/MS data (RT, MS) |
|---|---|---|
| I-102 | 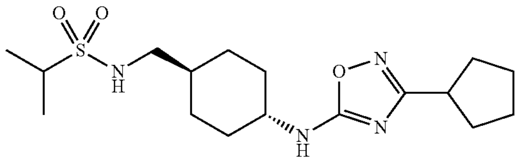 [SMILES: CC(C)S(=O)(=O)NC[C@H]1CC[C@H](Nc2nc(C3CCCC3)no2)CC1] | 1H-NMR (DMSO-d6) δ: 0.91-1.03 (2H, m), 1.16-1.26 (5H, m), 1.29-1.39 (1H, m), 1.53-1.72 (6H, m), 1.61-1.66 (6H, m), 1.75-1.82 (2H, m), 1.88-1.99 (4H, m), 2.76 (2H, t, J = 6.3 Hz), 2.89-2.99 (3H, m), 7.00 (1H, t, J = 6.1 Hz), 8.08 (1H, d, J = 7.6 Hz). 1H overlap with solvent. |
| I-103 | 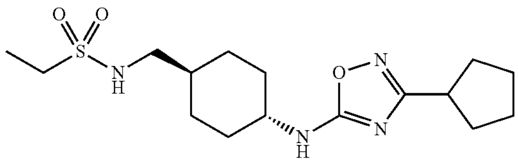 [SMILES: CCS(=O)(=O)NC[C@H]1CC[C@H](Nc2nc(C3CCCC3)no2)CC1] | 1H-NMR (DMSO-d6) δ: 0.90-1.05 (2H, m), 1.15-1.25 (8H, m), 1.28-1.39 (1H, m), 1.52-1.72 (6H, m), 1.75-1.83 (2H, m), 1.84-1.99 (4H, m), 2.78 (2H, t, J = 6.3 Hz), 2.89-2.96 (1H, m), 3.08-3.19 (1H, m), 6.96 (1H, t, J = 6.1 Hz), 8.08 (1H, d, J = 7.6 Hz). 1H overlap with solvent. |
| I-104 | 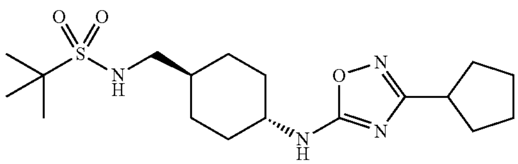 [SMILES: CC(C)(C)S(=O)(=O)NC[C@H]1CC[C@H](Nc2nc(C3CCCC3)no2)CC1] | 1H-NMR (DMSO-d6) δ: 0.91-1.04 (2H, m), 1.15-1.38 (12H, m), 1.53-1.72 (6H, m), 1.75-1.82 (2H, m), 1.84-1.99 (4H, m), 2.85-2.96 (3H, m), 6.85 (1H, t, J = 5.8 Hz), 8.08 (1H, d, J = 7.6 Hz). 1H overlap with solvent. |
| I-105 | 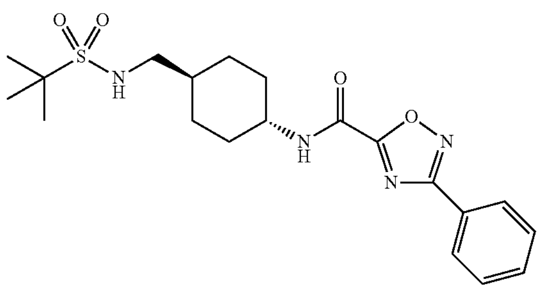 [SMILES: CC(C)(C)S(=O)(=O)NC[C@H]1CC[C@H](NC(=O)c2nc(-c3ccccc3)no2)CC1] | 1H-NMR (DMSO-d6) δ: 0.98-1.04 (2H, m), 1.34-1.37 (12H, m), 1.81-1.89 (4H, m), 2.89 (2H, t, J = 6.3 Hz), 3.75-3.77 (1H, m), 6.87 (1H, t, J = 5.8 Hz), 7.60-7.63 (3H, m), 8.06-8.08 (2H, m), 9.33 (1H, d, J = 8.6 Hz). |

TABLE 26

| No. | Structure | NMR |
|---|---|---|
| I-106 | 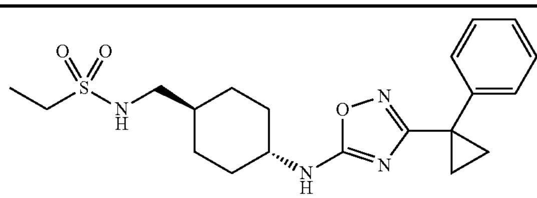 | 1H-NMR (DMSO-d6) δ: 0.91-1.03 (2H, m), 1.14-1.25 (7H, m), 1.29-1.42 (3H, m), 1.73-1.81 (2H, m), 1.88-1.99 (2H, m), 2.75 (2H, t, J = 6.1 Hz), 2.96 (2H, q, J = 7.3 Hz), 6.94-7.00 (1H, m), 7.21-7.37 (5H, m), 8.12 (1H, d, J = 8.1 Hz). 1H overlap with solvent. |
| I-107 | 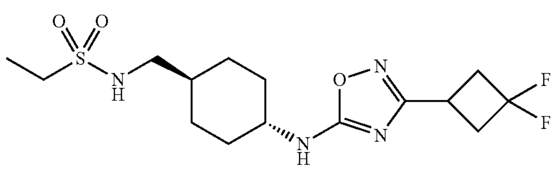 | 1H-NMR (DMSO-d6) δ: 0.93-1.04 (2H, m), 1.16-1.28 (5H, m), 1.30-1.40 (1H, m), 1.75-1.83 (2H, m), 1.92-2.00 (2H, m), 2.71-2.84 (4H, m), 2.90-3.01 (4H, m), 6.98 (1H, t, J = 6.1 Hz), 8.28 (1H, d, J = 7.6 Hz). 2H overlap with solvent. |
| I-108 | 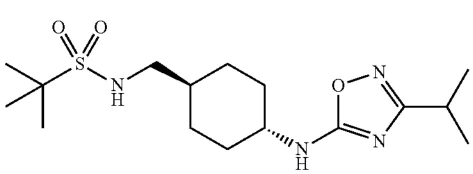 [SMILES: CC(C)c1noc(N[C@H]2CC[C@H](CNS(=O)(=O)C(C)(C)C)CC2)n1] | 1H-NMR (DMSO-d6) δ: 0.92-1.01 (2H, m), 1.13-1.38 (18H, m), 1.75-1.82 (2H, m), 1.92-2.00 (2H, m), 2.73-2.82 (1H, m), 2.8 (2H, t, J = 6.3 Hz), 6.83 (1H, t, J = 5.8 Hz), 8.07 (1H, d, J = 8.1 Hz). 1H overlap with solvent peak. |

TABLE 26-continued

| No. | Structure | NMR |
|---|---|---|
| I-109 | 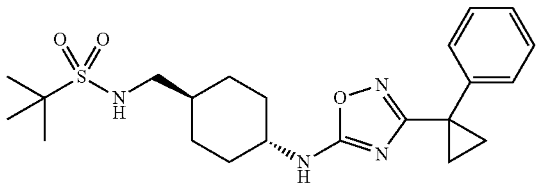 [SMILES: CC(C)(C)S(=O)(=O)NC[C@H]1CC[C@H](Nc2nc(C3(c4ccccc4)CC3)no2)CC1] | 1H-NMR (DMSO-d6) δ: 0.91-1.04 (2H, m), 1.14-1.25 (10H, m), 1.27-1.41 (3H, m), 1.73-1.82 (2H, m), 1.89-1.96 (2H, m), 2.78 (2H, t, J = 6.3 Hz), 3.08-3.18 (1H, m), 6.94 (1H, t, J = 5.8 Hz), 7.22-7.36 (5H, m), 8.11 (1H, d, J = 7.6 Hz). 1H overlap with solvent. |
| I-110 | 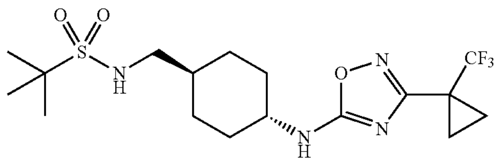 [SMILES: CC(C)(C)S(=O)(=O)NC[C@H]1CC[C@H](Nc2nc(C3(C(F)(F)F)CC3)no2)CC1] | 1H-NMR (DMSO-d6) δ: 0.91-1.04 (2H, m), 1.15-1.45 (16H, m), 1.74-1.83 (2H, m), 1.90-1.99 (2H, m), 2.87 (2H, t, J = 6.1 Hz), 6.83 (1H, t, J = 5.6 Hz), 8.41 (1H, d, J = 8.1 Hz). 1H overlap with solvent. |

TABLE 27

| No. | Structure | NMR |
|---|---|---|
| I-111 | 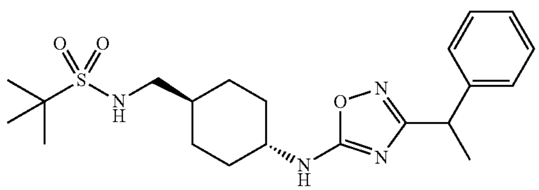 [SMILES: CC(c1ccccc1)c1noc(N[C@H]2CC[C@H](CNS(=O)(=O)C(C)(C)C)CC2)n1] | 1H-NMR (DMSO-d6) δ: 0.90-1.00 (2H, m), 1.14-1.34 (12H, m), 1.49 (3H, d, J = 7.1 Hz), 1.73-1.80 (2H, m), 1.8-1.95 (2H, m), 2.85 (2H, t, J = 6.1 Hz), 4.03 (1H, q, J = 7.1 Hz), 6.82 (1H, t, J = 5.6 Hz), 7.20-7.35 (5H, m), 8.14 (1H, d, J = 7.6 Hz). 1H overlap with solvent peak. |
| I-112 | 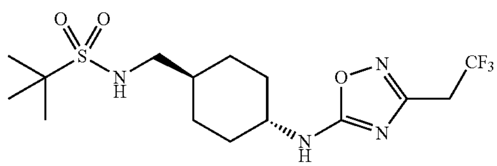 [SMILES: CC(C)(C)S(=O)(=O)NC[C@H]1CC[C@H](Nc2nc(CC(F)(F)F)no2)CC1] | 1H-NMR (DMSO-d6) δ: 0.91-1.04 (2H, m), 1.16-1.40 (12H, m), 1.80 (2H, d, J = 12 Hz), 1.96 (2H, t, J = 15 Hz), 2.87 (2H, t, J = 6.1 Hz), 3.72 (2H, q, J = 11 Hz), 6.84 (1H, t, J = 5.8 Hz), 8.44 (1H, d, J = 7.6 Hz). 1H overlaps with solvent peak |
| I-113 | 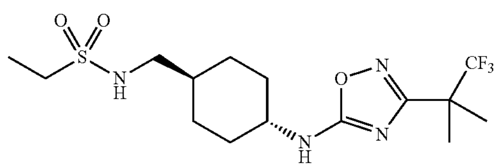 [SMILES: CCS(=O)(=O)NC[C@H]1CC[C@H](Nc2nc(C(C)(C)C(F)(F)F)no2)CC1] | 1H-NMR (DMSO-d6) δ: 0.93-1.05 (2H, m), 1.19 (3H, t, J = 7.4Hz), 1.20-1.40 (3H, m), 1.47 (6H, s), 1.79 (2H, d, J = 12 Hz), 1.96 (2H, d, J = 10 Hz), 2.76 (2H, t, J = 6.3 Hz), 2.97 (2H, q, J = 7.3 Hz), 6.98 (1H, t, J = 6.1 Hz), 8.42 (1H, d, J = 7.6 Hz). 1H overlaps with solvent peak |
| I-114 | 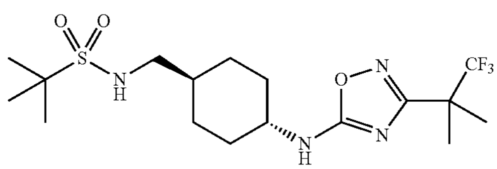 [SMILES: CC(C)(c1noc(N[C@H]2CC[C@H](CNS(=O)(=O)C(C)(C)C)CC2)n1)C(F)(F)F] | 1H-NMR (DMSO-d6) δ: 0.93-1.02 (2H, m), 1.16-1.38 (12H, m), 1.47 (6H, s), 1.79 (2H, d, J = 12 Hz), 1.96 (2H, d, J = 12 Hz), 2.87 (2H, t, J = 6.1 Hz), 6.83 (1H, t, J = 5.8 Hz), 8.42 (1H, d, J = 7.6 Hz). 1H overlaps with solvent peak |
| I-115 | 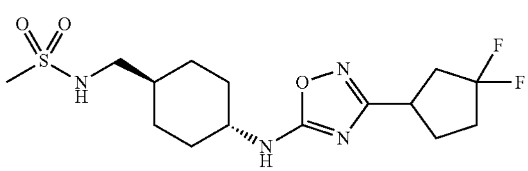 [SMILES: CS(=O)(=O)NC[C@H]1CC[C@H](Nc2nc(C3CCC(F)(F)C3)no2)CC1] | 1H-NMR (DMSO-d6) δ: 0.92-1.02 (2H, m), 1.17-1.40 (3H, m), 1.75-1.83 (2H, m), 1.89-2.00 (3H, m), 2.07-2.34 (4H, m), 2.78 (2H, t, J = 6.3 Hz), 2.86 (3H, s), 6.95 (1H, t, J = 6.1 Hz), 8.22 (1H, d, J = 7.6 Hz). 3H overlap with solvent peak. |

TABLE 28

| No. | Structure | NMR |
|---|---|---|
| I-116 | 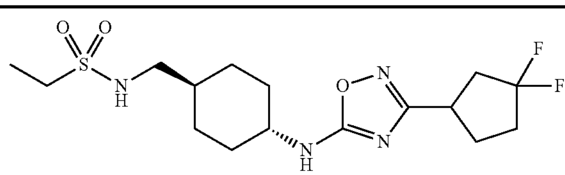 | 1H-NMR (DMSO-d6) δ: 0.92-1.02 (2H, m), 1.27-1.40 (6H, m), 1.75-1.83 (2H, m), 1.88-1.99 (3H, m), 2.09-2.35 (4H, m), 2.76 (2H, t, J = 6.6 Hz), 2.97 (2H, q, J = 7.3 Hz), 6.98 (1H, t, J = 5.8 Hz), 8.22 (1H, d, J = 8.1 Hz). 3H overlap with solvent |

TABLE 28-continued

| ID | Structure | NMR |
|---|---|---|
| I-117 | 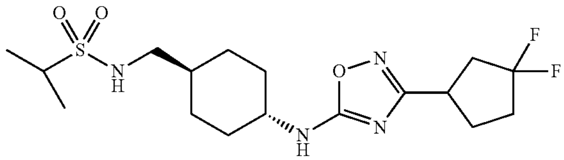 [SMILES: CC(C)S(=O)(=O)NC[C@H]1CC[C@H](Nc2nc(C3CCC(F)(F)C3)no2)CC1] | 1H-NMR (DMSO-d6) δ: 0.92-1.02 (2H, m), 1.18-1.40 (9H, m), 1.75-1.83 (2H, m), 1.88-2.00 (3H, m), 2.07-2.35 (4H, m), 2.79 (2H, t, J = 6.3 Hz), 3.10-3.17 (1H, m), 6.94 (1H, t, J = 6.1 Hz), 8.22 (1H, d, J = 7.6 Hz). 3H overlap with solvent peak. |
| I-118 | 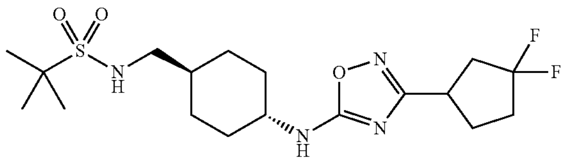 [SMILES: CC(C)(C)S(=O)(=O)NC[C@H]1CC[C@H](Nc2nc(C3CCC(F)(F)C3)no2)CC1] | 1H-NMR (DMSO-d6) δ: 0.93-1.01 (2H, m), 1.17-1.36 (12H, m), 1.75-1.83 (2H, m), 1.88-1.99 (3H, m), 2.21-2.37 (4H, m), 2.87 (2H, t, J = 6.3 Hz), 6.83 (1H, t, J = 5.8 Hz), 8.22 (1H, d, J = 7.6 Hz). 3H overlap with solvent peak. |
| I-119 | 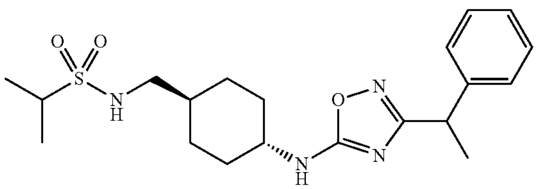 [SMILES: CC(c1ccccc1)c1noc(N[C@H]2CC[C@H](CNS(=O)(=O)C(C)C)CC2)n1] | 1H-NMR (DMSO-d6) δ: 0.90-1.00 (2H, m), 1.10-1.25 (8H, m), 1.25-1.4 (1H, m), 1.49 (3H, d, J = 7.1 Hz), 1.72-1.81 (2H, m), 1.85-1.92 (2H, m), 2.77 (2H, t, J = 6.1 Hz), 3.10-3.17 (1H, m), 4.03 (1H, q, J = 7.1 Hz), 6.94 (1H, t, J = 5.6 Hz), 7.19-7.35 (5H, m), 8.15 (1H, d, J = 7.6 H). 1H overlap with solvent peak. |
| I-120 | 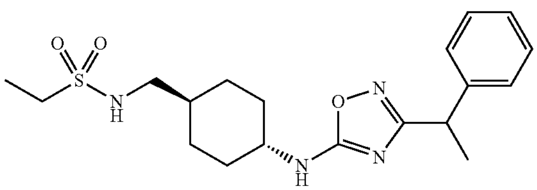 [SMILES: CCS(=O)(=O)NC[C@H]1CC[C@H](Nc2nc(C(C)c3ccccc3)no2)CC1] | 1H-NMR (DMSO-d6) δ: 0.85-1.00 (2H, m), 1.13-1.25 (5H, m), 1.25-1.40 (1H, m), 1.49 (3H, d, J = 7.1 Hz), 1.72-1.82 (2H, m), 1.87-1.97 (2H, m), 2.75 (2H, d, J = 7.1 Hz), 2.96 (2H, q, J = 7.4 Hz), 4.03 (1H, q, J = 7.1 Hz), 6.97 (1H, brs), 7.20-7.35 (5H, m), 8.15 (1H, brs). 1H overlap with solvent peak. |

TABLE 29

| ID | Structure | NMR |
|---|---|---|
| I-121 | 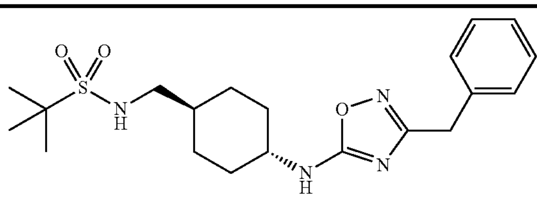 | 1H-NMR (DMSO-d6) δ: 0.88-1.00 (2H, m), 1.14-1.34 (12H, m), 1.72-1.91 (2H, m), 1.88-1.96 (2H, m), 2.85 (2H, t, J = 6.1 Hz), 3.79 (2H, s), 6.82 (1H, t, J = 5.6 Hz), 7.20-7.35 (5H, m), 8.16 (1H, d, J = 7.6 Hz). 1H overlap with solvent peak |
| I-122 | 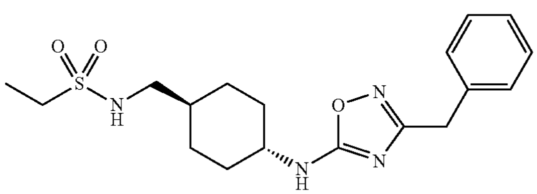 [SMILES: CCS(=O)(=O)NC[C@H]1CC[C@H](Nc2nc(Cc3ccccc3)no2)CC1] | 1H-NMR (DMSO-d6) δ: 0.88-1.00 (2H, m), 1.14-1.25 (5H, m), 1.24-1.40 (1H, m), 1.72-1.82 (2H, m), 1.88-1.96 (2H, m), 2.72-2.78 (2H, m), 2.96 (2H, q, J = 7.3 Hz), 3.79 (2H, s), 6.97 (1H, brs), 7.20-7.35 (5H, m), 8.16 (1H, d, J = 7.6 Hz). 1H overlap with solvent peak. |
| I-123 | 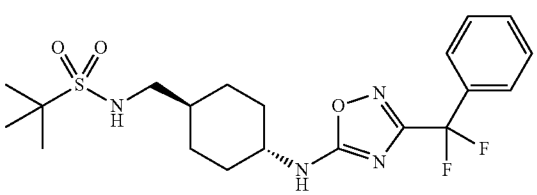 [SMILES: CC(C)(C)S(=O)(=O)NC[C@H]1CC[C@H](Nc2nc(C(F)(F)c3ccccc3)no2)CC1] | 1H-NMR (DMSO-d6) δ: 0.92-1.03 (2H, m), 1.18-1.42 (12H, m), 1.75-1.82 (2H, m), 1.90-2.00 (2H, m), 2.86 (2H, t, J = 6.1 Hz), 6.83 (1H, t, J = 5.8 Hz), 7.52-7.61 (5H, m), 8.73 (1H, d, J = 7.1 Hz). 1H overlap with solvent peak. |
| I-124 | 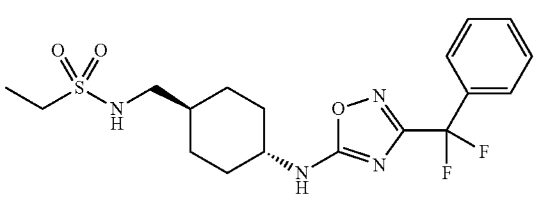 [SMILES: CCS(=O)(=O)NC[C@H]1CC[C@H](Nc2nc(C(F)(F)c3ccccc3)no2)CC1] | 1H-NMR (DMSO-D6) δ: 0.91-1.05 (2H, m), 1.13-1.41 (6H, m), 1.73-1.82 (2H, m), 1.89-1.99 (2H, m), 2.71-2.79 (2H, m), 2.96 (2H, q, J = 7.3 Hz), 6.98 (1H, br s), 7.51-7.62 (5H, m), 8.74 (1H, d, J = 3.0 Hz). 1H overlap with solvent peak. |

TABLE 29-continued

| | | |
|---|---|---|
| I-125 | 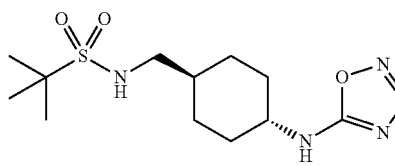 | 1H-NMR (DMSO-D6) δ: 0.89-1.01 (2H, m), 1.12-1.38 (12H, m), 1.71-1.82 (2H, m), 1.88-1.98 (2H, m), 2.82-2.89 (2H, m), 3.80 (2H, s), 6.82 (1H, s), 7.10-7.16 (2H, m), 7.29-7.34 (2H, m), 8.18 (1H, d, J = 7.6 Hz). 1H overlap with solvent peak. |

TABLE 30

| | | |
|---|---|---|
| I-126 | 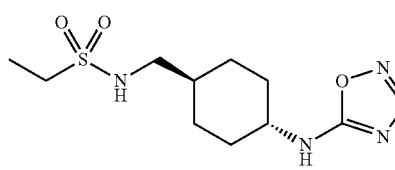 | 1H-NMR (DMSO-D6) δ: 0.89-1.02 (2H, m), 1.12-1.26 (5H, m), 1.27-1.40 (1H, m), 1.73-1.81 (2H, m), 1.88-1.96 (2H, m), 2.72-2.78 (2H, m), 2.96 (2H, q, J = 7.4 Hz), 3.80 (2H, s), 6.97 (1H, br s), 7.13 (2H, t, J = 8.9 Hz), 7.31 (2H, dd, J = 8.6, 5.6 Hz), 8.18 (1H, d, J = 8.1 Hz). 1H overlap with solvent peak. |
| I-127 | 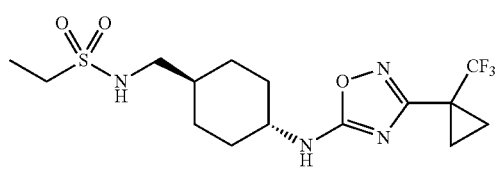 [SMILES: CCS(=O)(=O)NC[C@H]1CC[C@H](Nc2nc(C3(C(F)(F)F)CC3)no2)CC1] | 1H-NMR (DMSO-d6) δ: 0.93-1.05 (2H, m), 1.13-1.28 (5H, m), 1.28-1.46 (5H, m), 1.78 (2H, d, J = 12 Hz), 1.94 (2H, d, J = 10 Hz), 2.76 (2H, t, J = 6.3 Hz), 2.97 (2H, q, J = 7.4 Hz), 6.98 (1H, t, J = 5.8 Hz), 8.42 (1H, d, J = 7.6 Hz). 1H overlaps with solvent peak |
| I-128 | 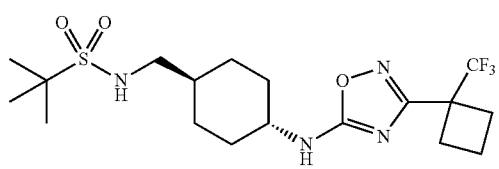 [SMILES: CC(C)(C)S(=O)(=O)NC[C@H]1CC[C@H](Nc2nc(C3(C(F)(F)F)CCC3)no2)CC1] | 1H-NMR (DMSO-d6) δ: 0.93-1.05 (2H, m), 1.19-1.42 (12H, m), 1.79 (2H, d, J = 13 Hz), 1.93-2.05 (4H, m), 2.50-2.56 (4H, m), 2.87 (2H, t, J = 6.3 Hz), 3.30-3.40 (1H, m), 6.83 (1H, t, J = 5.8 Hz), 8.44 (1H, d, J = 7.6 Hz). |
| I-129 | 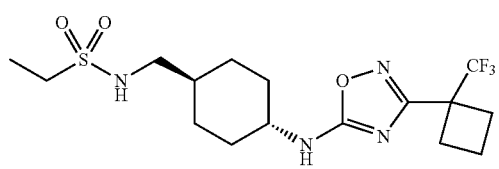 [SMILES: CCS(=O)(=O)NC[C@H]1CC[C@H](Nc2nc(C3(C(F)(F)F)CCC3)no2)CC1] | 1H-NMR (DMSO-d6) δ: 0.95-1.04 (2H, m), 1.18 (3H, t, 7.4 Hz), 1.23 (2H, q, J = 12 Hz), 1.30-1.40 (1H, m), 1.79 (2H, d, J = 12 Hz), 1.92-2.03 (4H, m), 2.50-2.57 (4H, m), 2.76 (2H, t, J = 6.6 Hz), 2.97 (2H, q, J = 7.4 Hz), 3.33-3.40 (1H, m), 6.98 (1H, t, J = 6.1 Hz), 8.45 (1H, d, J = 7.6 Hz). |
| I-130 | 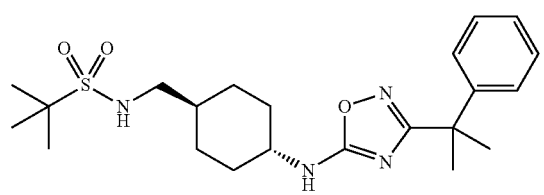 | 1H-NMR (CDCl3) δ: 0.88-1.01 (2H, m), 1.11-1.37 (12H, m), 1.59 (6H, s), 1.71-1.81 (2H, m), 1.86-1.96 (2H, m), 2.85 (2H, t, J = 6.3 Hz), 6.81 (1H, t, J = 5.6 Hz), 7.20 (1H, dd, J = 8.9, 4.3 Hz), 7.27-7.33 (4H, m), 8.10 (1H, d, J = 8.1 Hz). 1H overlap with solvent peak. |

TABLE 31

| | | |
|---|---|---|
| I-131 | 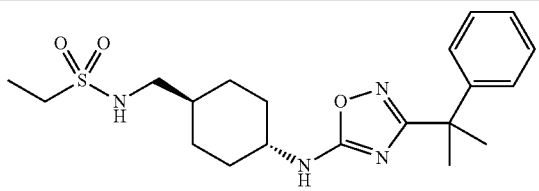 [SMILES: CCS(=O)(=O)NC[C@H]1CC[C@H](Nc2nc(C(C)(C)c3ccccc3)no2)CC1] | 1H-NMR (DMSO-D6) δ: 0.88-1.01 (2H, m), 1.10-1.25 (5H, m), 1.26-1.39 (1H, m), 1.59 (6H, s), 1.71-1.80 (2H, m), 1.86-1.96 (2H, m), 2.70-2.77 (2H, m), 2.95 (2H, q, J = 7.3 Hz), 6.96 (1H, s), 7.17-7.24 (1H, m), 7.28-7.32 (4H, m), 8.10 (1H, d, J = 7.6 Hz). 1H overlap with solvent peak. |

TABLE 31-continued

| | | |
|---|---|---|
| I-132 | (structure) | 1H-NMR (DMSO-d6) δ: 0.92-1.04 (2H, m), 1.18-1.40 (12H, m), 1.79 (2H, d, J = 12 Hz), 1.96 (2H, d, J = 9.6 Hz), 2.71-2.83 (2H, m), 2.87 (2H, t, J = 6.34), 2.91-3.01 (2H, m), 6.83 (1H, t, J = 5.6 Hz), 8.27 (1H, d, J = 7.6 Hz). 2H overlap with solvent peak. |
| I-133 | (structure) | 1H-NMR (DMSO-d6) δ: 0.91-1.05 (2H, m), 1.16-1.37 (9H, m), 1.75-1.83 (2H, m), 1.93-2.00 (2H, m), 2.75-2.83 (4H, m), 2.90-3.01 (2H, m), 3.08-3.19 (1H, m), 6.95 (1H, t, J = 5.8 Hz), 8.28 (1H, d, J = 8.1 Hz). 2H overlap with solvent peak. |
| I-134 | (structure) | 1H-NMR (DMSO-D6) δ: 0.92-1.05 (2H, m), 1.18-1.40 (12H, m), 1.75-1.84 (2H, m), 1.89-2.02 (5H, m), 2.87 (2H, t, J = 6.6 Hz), 6.84 (1H, t, J = 5.6 Hz), 8.69 (1H, d, J = 7.1 Hz). 1H overlap with solvent peak. |
| I-135 | (structure) | 1H-NMR (DMSO-d6) δ: 0.37-0.51 (4H, m), 0.93-1.05 (2H, m), 1.17-1.40 (12H, m), 1.75-1.83 (2H, m), 1.93-2.00 (2H, m), 2.25-2.30 (2H, m), 2.40-2.47 (2H, m), 2.87 (2H, t, J = 6.1 Hz), 3.46-3.55 (1H, m), 6.85 (1H, t, 5.8 Hz), 8.13 (1H, d, J = 7.6 Hz). 1H overlaps with solvent peak |

TABLE 32

| | | |
|---|---|---|
| I-136 | (structure) | 1H-NMR (DMSO-D6) δ: 0.93-1.06 (2H, m), 1.14-1.41 (12H, m), 1.74-1.86 (2H, m), 1.93-2.03 (2H, m), 2.84-2.90 (2H, m), 6.84 (1H, t, J = 5.8 Hz), 9.07 (1H, br s). 1H overlap with solvent peak. |
| I-137 | (structure) | 1H-NMR (DMSO-d6) δ: 0.92-1.03 (2H, m), 1.15-1.42 (12H, m), 1.75-1.83 (2H, m), 1.93-2.00 (2H, m), 2.83-3.01 (6H, m), 4.79-4.83 (2H, m), 6.85 (1H, t, J = 5.3 Hz), 8.16 (1H, d, J = 7.6 Hz). 2H overlap with solvent peak. |
| I-138 | (structure) | 1H-NMR (DMSO-d6) δ: 0.92-1.02 (2H, m), 1.16-1.35 (6H, m), 1.75-1.85 (6H, m), 1.93-2.15 (6H, m), 2.76 (2H, t, J = 6.3 Hz), 2.97 (2H, q, J = 7.3 Hz), 7.00 (1H, t, J = 5.8 Hz), 8.37 (1H, d, J = 7.6 Hz). 1H overlap with solvent peak. |
| I-139 | (structure) | 1H-NMR (DMSO-d6) δ: 0.92-1.02 (2H, m), 1.20-1.40 (9H, m), 1.70-1.90 (6H, m), 1.93-2.20 (6H, m), 2.79 (2H, t, J = 6.3 Hz), 3.10-3.17 (1H, m), 6.96 (1H, t, J = 6.1 Hz), 8.37 (1H, d, J = 7.6 Hz). 1H overlap with solvent peak. |
| I-140 | (structure) | 1H-NMR (DMSO-d6) δ: 0.92-1.02 (2H, m), 1.18-1.40 (12H, m), 1.70-1.90 (6H, m), 1.90-2.20 (6H, m), 2.87 (2H, t, J = 6.3 Hz), 6.85 (1H, t, J = 5.8 Hz), 8.37 (1H, d, J = 8.1 Hz). 1H overlap with solvent peak. |

TABLE 33

| | | |
|---|---|---|
| I-141 | (structure) | 1H-NMR (DMSO-D6) δ: 0.94-1.07 (2H, m), 1.14-1.43 (6H, m), 1.75-1.86 (2H, m), 1.92-2.03 (2H, m), 2.73-2.79 (2H, m), 2.97 (2H, q, J = 7.3 Hz), 3.36-3.48 (1H, m), 7.00 (1H, t, J = 6.1 Hz), 9.09 (1H, br s). |
| I-142 | (structure) | 1H-NMR (DMSO-d6) δ: 0.93-1.05 (2H, m), 1.16-1.40 (6H, m), 1.50 (3H, s), 1.75-1.83 (2H, m), 1.93-2.00 (2H, m), 2.59-2.70 (2H, m), 2.76 (2H, t, J = 6.3 Hz), 2.95-3.05 (4H, m), 6.99 (1H, t, J = 6.1 Hz), 8.28 (1H, d, J = 7.6 Hz). 1H overlap with solvent peak. |
| I-143 | (structure) | 1H-NMR (DMSO-d6) δ: 0.92-1.04 (2H, m), 1.18-1.40 (12H, m), 1.50 (3H, s), 1.75-1.83 (2H, m), 1.93-2.00 (2H, m), 2.58-2.68 (2H, m), 2.87 (2H, t, J = 6.3 Hz), 3.00 (2H, q, J = 14 Hz), 6.84 (1H, t, J = 5.8 Hz), 8.28 (1H, 7.6 Hz). 1H overlap with solvent peak. |
| I-144 | (structure) | 1H-NMR (DMSO-D6) δ: 0.92-1.05 (2H, m), 1.15-1.40 (9H, m), 1.47 (6H, s), 1.74-1.84 (2H, m), 1.91-2.00 (2H, m), 2.74-2.84 (2H, m), 3.08-3.19 (1H, m), 6.96 (1H, t, J = 6.1 Hz), 8.43 (1H, d, J = 7.6 Hz). 1H overlap with solvent peak. |
| I-145 | (structure) | 1H-NMR (DMSO-D6) δ: 0.93-1.06 (2H, m), 1.17-1.42 (9H, m), 1.75-1.85 (2H, m), 1.93-2.02 (2H, m), 2.76-2.82 (2H, m), 3.09-3.20 (1H, m), 6.97 (1H, t, J = 5.8 Hz), 9.09 (1H, br s). 1H overlap with solvent peak. |

TABLE 34

| | | |
|---|---|---|
| I-146 | (structure) | 1H-NMR (DMSO-d6) δ: 0.90-1.05 (2H, m), 1.12-1.40 (12H, m), 1.79 (2H, d, J = 11 Hz), 1.97 (2H, d, J = 12 Hz), 2.87 (2H, t, J = 6.1 Hz), 6.85 (1H, t, J = 5.8 Hz), 7.65 (1H, d, J = 7.6 Hz), 8.09 (1H, d, J = 2.0 Hz). 1H overlap with solvent peak. |
| I-147 | (structure) | 1H-NMR (DMSO-d6) δ: 0.93-1.05 (2H, m), 1.15-1.40 (9H, m), 1.50 (3H, s), 1.75-1.82 (2H, m), 1.92-2.00 (2H, m), 2.55-2.67 (2H, m), 2.79 (2H, t, J = 6.3 Hz), 2.95-3.05 (2H, m), 3.10-3.17 (1H, m), 6.95 (1H, t, J = 6.1 Hz), 8.27 (1H, d, J = 8.1 Hz). 1H overlap with solvent peak. |
| I-148 | (structure) | 1H-NMR (DMSO-d6) δ: 0.85-1.02 (6H, m), 1.18-1.28 (2H, m), 1.30-1.42 (1H, m), 1.50 (3H, s), 1.76-1.83 (2H, m), 1.93-2.00 (2H, m), 2.58-2.68 (2H, m), 2.82 (2H, t, J = 6.6 Hz), 3.95-3.05 (2H, m), 7.02 (1H, t, J = 6.1 Hz), 8.28 (1H, d, J = 8.1 Hz). 2H overlap with solvent peaks. |
| I-149 | (structure) | 1H-NMR (DMSO-D6) δ: 0.93-1.06 (2H, m), 1.19-1.40 (12H, m), 1.76-1.84 (2H, m), 1.94-2.02 (2H, m), 2.84-2.90 (2H, m), 6.85 (1H, t, J = 5.3 Hz), 9.16 (1H, br s). 1H overlap with solvent peak. |

TABLE 34-continued

| | | |
|---|---|---|
| I-150 | (structure) | 1H-NMR (DMSO-d6) δ: 0.92-1.02 (2H, m), 1.15-1.25 (8H, m), 1.34 (1H, s), 1.79 (2H, d, J = 12 Hz), 1.97 (2H, d, J = 13 Hz), 2.78 (2H, t, J = 6.3 Hz), 3.10-3.18 (1H, m), 6.96 (1H, t, J = 5.8 Hz), 7.64 (1H, d, J = 8.1 Hz), 8.09 (1H, d, J = 1.5 Hz). 1H overlap with solvent peak. |

TABLE 35

| | | |
|---|---|---|
| I-151 | (structure) | 1H-NMR (DMSO-d6) δ: 0.90-1.30 (13H, m), 1.30-1.40 (1H, m), 1.79 (2H, d, J = 12 Hz), 2.02 (2H, d, J = 9.6 Hz), 2.88 (2H, t, J = 6.1 Hz), 6.84 (1H, t, J = 5.6 Hz), 7.29 (1H, s), 7.96 (1H, d, J = 7.6 Hz). 1H overlap with solvent peak. |
| I-152 | (structure) | 1H-NMR (DMSO-D6) δ: 0.93-1.06 (2H, m), 1.13-1.42 (9H, m), 1.75-1.84 (2H, m), 1.93-2.02 (2H, m), 2.76-2.82 (2H, m), 3.08-3.20 (1H, m), 6.97 (1H, t, J = 6.1 Hz), 9.17 (1H, br s). 1H overlap with solvent peak. |
| I-153 | (structure) | 1H-NMR (DMSO-D6) δ: 0.94-1.07 (2H, m), 1.12-1.43 (6H, m), 1.76-1.84 (2H, m), 1.93-2.02 (2H, m), 2.74-2.79 (2H, m), 2.97 (2H, q, J = 7.4 Hz), 7.00 (1H, t, J = 5.3 Hz), 9.16 (1H, br s). 1H overlap with solvent peak |
| I-154 | (structure) | 1H-NMR (DMSO-d6) δ: 0.75-0.80 (2H, m), 0.88-1.45 (10H, m), 1.50 (3H, s), 1.78-1.83 (2H, m), 1.92-2.00 (2H, m), 2.58-2.68 (2H, m), 2.80 (2H, t, J = 11Hz), 2.95-3.06 (2H, m), 7.09 (1H, t, J = 6.1 Hz), 8.28 (1H, d, J = 7.6 Hz). 1H overlap with solvent peak. |
| I-155 | (structure) | 1H-NMR (DMSO-D6) δ: 0.85-1.08 (6H, m), 1.21-1.43 (3H, m), 1.77-1.86 (2H, m), 1.94-2.02 (2H, m), 2.79-2.86 (2H, m), 7.03 (1H, t, J = 6.1 Hz), 9.16 (1H, s). 2H overlap with solvent peak. |

TABLE 36

| | | |
|---|---|---|
| I-156 | (structure) | 1H-NMR (DMSO-D6) δ: 0.95-1.08 (2H, m), 1.20-1.44 (3H, m), 1.75-1.84 (2H, m), 1.94-2.02 (2H, m), 2.76-2.81 (2H, m), 2.87 (3H, s), 6.97 (1H, t, J = 5.8 Hz), 9.16 (1H, d, J = 3.5 Hz). 1H overlap with solvent peak. |
| I-157 | (structure) | 1H-NMR (DMSO-d6) δ: 0.92-1.05 (2H, m), 1.15-1.40 (13H, m), 1.80 (2H, d, J = 12 Hz), 2.01 (2H, d, J = 9 Hz), 2.80-3.00 (6H, m), 6.84 (1H, t, J = 5.6 Hz), 8.45 (1H, s). 1H overlap with solvent peak. |

TABLE 36-continued

| | | |
|---|---|---|
| I-158 | [structure] | 1H-NMR (DMSO-d6) δ: 0.95-1.08 (2H, m), 1.15-1.45 (12H, m), 1.81 (2H, d, J = 12 Hz), 2.04 (2H, d, J = 10 Hz), 2.88 (2H, t, J = 6.3 Hz), 6.85 (1H, t, J = 5.83 Hz), 8.95 (1H, bs). 1H overlap with solvent peak. |
| I-159 | [structure] | 1H-NMR (DMSO-d6) δ: 0.95-1.05 (2H, m), 1.15-1.45 (6H, m), 1.79 (2H, d, J = 12 Hz), 2.02 (2H, d, J = 11 Hz), 2.75-3.00 (8H, m), 7.00 (1H, t, J = 6.1 Hz), 8.45 (1H, s). 2H overlap with solvent peak. |
| I-160 | [structure] | 1H-NMR (DMSO-d6) δ: 0.97-1.10 (2H, m), 1.15-1.30 (5H, m), 1.40 (1H, bs), 1.81 (2H, d, J = 12 Hz), 2.03 (2H, d, J = 10 Hz), 2.77 (2H, t, J = 6.3 Hz), 2.97 (2H, q, J = 7.4 Hz), 7.01 (1H, t, J = 6.1 Hz), 8.92 (1H, bs). |

TABLE 37

| | | |
|---|---|---|
| I-161 | [structure] | 1H-NMR (DMSO-d6) δ: 0.94-1.04 (2H, m), 1.16-1.36 (13H, m), 1.80 (2H, d, J = 13 Hz), 1.98 (2H, d, J = 11 Hz), 2.87 (2H, t, J = 6.3 Hz), 3.25-3.44 (4H, m), 6.85 (1H, t, J = 5.8 Hz), 8.59 (1H, d, J = 8.1 Hz). |

TABLE 38

| | | |
|---|---|---|
| I-162 | [structure] | 1H-NMR (DMSO-d6) δ: 1.00-1.32 (7H, m), 1.41 (1.0H, bs), 1.83 (2H, d, J = 12 Hz), 2.09 (2H, d, J = 10 Hz), 2.79 (2H, t, J = 6.3 Hz), 2.98 (2H, q, J = 7.3 Hz), 3.43 (1H, bs), 7.01 (1H, t, J = 6.1 Hz), 7.44-7.50 (3H, m), 8.05-8.10 (2H, m), 8.49 (1H, bs). |
| I-163 | [structure] | 1H-NMR (DMSO-d6) δ: 0.95-1.10 (2H, m), 1.20-1.32 (8H, m), 1.39 (1H, bs), 1.83 (2H, d, J = 12 Hz), 2.10 (2H, d, J = 10 Hz), 2.82 (2H, t, J = 6.3 Hz), 3.12-3.18 (1H, m), 3.44 (1H, bs), 6.97 (1H, t, J = 6.1 Hz), 7.42-7.50 (3H, m), 8.05-8.10 (2H, m), 8.49 (1H, bs). |
| I-164 | [structure] | 1H-NMR (DMSO-d6) δ: 1.00-1.12 (2H, m), 1.20-1.32 (2H, m), 1.42 (1H, s), 1.83 (2H, d, J = 12 Hz), 2.10 (2H, d, J = 10 Hz), 2.81 (2H, t, J = 6.3 Hz), 2.88 (3H, s), 3.42 (1H, bs), 6.98 (1H, t, J = 6.1 Hz), 7.42-7.50 (3H, d, J = 3.6 Hz), 8.05-8.10 (2H, t, J = 3.8 Hz), 8.49 (1H, s). |
| I-165 | [structure] | 1H-NMR (DMSO-d6) δ: 0.96-1.05 (2H, m), 1.15-1.40 (12H, m), 1.81 (2H, d, J = 12 Hz), 2.01 (2H, t, J = 10 Hz), 2.89 (2H, t, J = 6.1 Hz), 6.85 (1H, t, J = 6.1 Hz), 7.15 (1H, d, J = 8.1 Hz), 7.24 (1H, t, J = 7.4 Hz), 7.36 (2H, t, J = 7.6 Hz), 7.65 (2H, d, J = 7.1 Hz), 7.90 (0.9H, s). 1H overlap with solvent peak. |

TABLE 38-continued

| | | |
|---|---|---|
| I-166 | 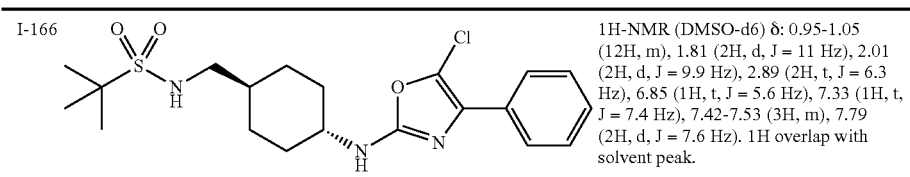 | 1H-NMR (DMSO-d6) δ: 0.95-1.05 (12H, m), 1.81 (2H, d, J = 11 Hz), 2.01 (2H, d, J = 9.9 Hz), 2.89 (2H, t, J = 6.3 Hz), 6.85 (1H, t, J = 5.6 Hz), 7.33 (1H, t, J = 7.4 Hz), 7.42-7.53 (3H, m), 7.79 (2H, d, J = 7.6 Hz). 1H overlap with solvent peak. |

The Test Examples of the present invention are described as follows:

Experiment 1

Affinity for Mouse NPY Y5 Receptor cDNA sequence encoding a mouse NPY Y5 receptor (Biochim. Biophys. Acta 1328:83-89, 1997) was cloned in a vector (pME18S, Takebe et al. Mol. Cell. Biol. 8, 8957). The obtained expression vector was transfected into CHO cells as a host by using Lipofect AMINE reagent (Trademark, Gico BRL Co., Ltd.) according to the instruction manual. The cells that stably express NPY Y5 receptor were obtained.

The membranes prepared from the CHO cells expressing NPY Y5 receptor, the compound of this invention and 30,000 cpm [$^{125}$I] peptide YY (60 pM of final concentration: Healthcare) were incubated in the assay buffer (20 mM HEPES-Hanks buffer containing 0.1% bovine serum albumin, pH 7.4) at 25° C. for 2 hours, and then the membrane was filtered from the mixture through a glass filter (GF/C) presoaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test compound against the specific peptide YY binding (IC50 value) was calculated (Inui, A. et al. Endocrinology 131, 2090-2096 (1992)). The results are shown as follows.

The compounds of this invention inhibited the binding of peptide YY (NPY homologue) to NPY Y5 receptor, indicating that the compounds of this invention have an affinity for the NPY Y5 receptor.

The results are shown as following:
Compound I-006: 0.32 nM
Compound I-011: 0.34 nM
Compound I-017: 0.22 nM
Compound I-018: 0.20 nM
Compound I-023: 1.40 nM
Compound I-024: 0.13 nM
Compound I-027: 0.86 nM
Compound I-029: 0.22 nM
Compound I-034: 0.18 nM
Compound I-053: 0.23 nM
Compound I-081: 0.90 nM
Compound I-099: 0.80 nM
Compound I-100: 0.90 nM
Compound I-130: 0.7 nM
Compound I-136: 1.5 nM
Compound I-138: 0.5 nM
Compound I-143: 0.8 nM
Compound I-145: 3.1 nM
Compound I-146: 4.21 nM
Compound I-147: 0.61 nM
Compound I-149: 1.04 nM
Compound I-150: 3.6 nM
Compound I-152: 0.65 nM
Compound I-153: 1.67 nM
Compound I-161: 1.9 nM

Experiment 2

Affinity for Human NPY Y5 Receptor cDNA sequence encoding a human NPY Y5 receptor (WO96/16542) was cloned in a vector (pME18S, Takebe et al. Mol. Cell. Biol. 8, 466-472). The obtained expression vector was transfected into CHO cells as a host by using Lipofect AMINE reagent (Trademark, Inbitrogen) according to the instruction manual. The cells that stably express human NPY Y5 receptor were obtained.

The membranes prepared from the CHO cells expressing human NPY Y5 receptor, the compound of this invention and 30,000 cpm [$^{125}$I] peptide YY (60 pM of final concentration: Healthcare) were incubated in the assay buffer (20 mM HEPES-Hanks buffer containing 0.1% bovine serum albumin, pH 7.4) at 25° C. for 2 hours, and then the membrane was filtered from the mixture through a glassfilter (GF/C) presoaked with 1% polyethyleneimine. After washing with 50 mM Tris-HCl buffer (pH 7.4), radioactivity retained on the filters was quantified with a gamma counter. Nonspecific binding was defined as the amount of radioactivity bound to the membranes after incubation in the presence of 200 nM of peptide YY. The 50% inhibitory concentration of the test compound against the specific peptide YY binding (IC50 value) was calculated (Inui, A. et al. Endocrinology 131, 2090-2096 (1992)).

The results are shown as following:
Compound I-017: 0.81 nM
Compound I-029: 0.86 nM

Experiment 3

Evaluation for Brain Penetration in Rats

By using the cassette dosing method (Drug. Metab. Dispos. (2001); 29, 957-966), brain penetration rate of the compounds (brain/plasma partition coefficients; Kp) were evaluated from plasma and brain concentrations at 30 minutes after intravenous administration (0.5 mg/mL/kg) in rats (Crl; CD(SD), ♂, 8 weeks).

Experiment 4

Evaluation for Brain Penetration in Mice

By using the cassette dosing method (Drug. Metab. Dispos. (2001); 29, 957-966), brain penetration rate of the compounds (brain/plasma partition coefficients; Kp) were evaluated from plasma and brain concentrations at 3 or 5 hours after oral administration (2 mg/10 mL/kg) in mice (Jcl; C57BL/6J, ♂, 8 weeks).

Experiment 5

Pharmacokinetic Analysis in Rats

By using the cassette dosing method, half-life (t½) and total clearance (CLtot) of the compounds of this invention were estimated from change in plasma concentration of each compound in rats (Crl; CD(SD), ♂, 8 weeks) after intravenous administration (0.5 mg/mL/kg).

Experiment 6

Inhibitory Effect on cAMP Production in CHO Cells

CHO cells expressing human NPY Y5 receptor were incubated in the presence of 2.5 mM isobutylmethylxanthine (SIGMA) at 37° C. for 20 min. After the incubation the compound of the present invention was added, and then the mixture was incubated for 5 min. Next, 50 nM NPY and 10 µM forskolin (SIGMA) were added, and the mixture was incubated for 30 min. After termination of the reaction by adding 1N HCl, the amount of cAMP in the supernatant was determined with an EIA kit (Amersham LIFE SCIENCE). The inhibitory activity of NPY against forskolin stimulated cAMP production was expressed as 100% and the 50% inhibitory concentration (IC50 value) of the compound of the present invention against the NPY activity was calculated.

The results are shown as following:
Compound I-017: 3.3 nM
Compound I-018: 2.1 nM
Compound I-029: 1.3 nM

Experiment 7

Selectivity for NPY Y5 Receptor

Using the membranes prepared from Y1-expression cells (human neuroblastoma, SK-N-MC) and the membranes prepared from Y2-expression cells (human neuroblastoma, SMS-KAN), the experiment is carried out in a similar way as Experiment 2 to determine the affinity of the compounds for NPY Y1 and NPY Y2 receptor. The results can be showed that the compounds of this invention have no significant affinity for their receptors, indicating high selectivity for NPY Y5 receptor.

Experiment 8

Effect of Suppressing Food Intake

Under diethylether anesthesia the skull of male C57BL/6J mice (12-14 wee k old, 25-30 g) was exposed by making an incision about 1-mm long from externa 1 occipital crest to nasal dorsum, and then drilled in the 1-mm lateral position to the left following 1-mm posterior from bregma. After recovery from anesthesia mice were dosed with either 0.5% hydroxypropylmethyl cellulose solution (vehicle, Shin-Etsu Chemical Co., Ltd) or the compounds of this invention suspended in the 0.5% hydroxypropylmethyl cellulose solution. At one hour after the treatment, each animal received saline or a NPY Y5 receptor specific agonist, [cPP1-7, NPY19-23, Ala31, Aib32, Gln34]-hPancreatic Polypeptide (0.1 nmol/1.5 µL saline/mouse) through the skull opening using a canula. Residual food was measured at 2 and 4 hours after the treatment. The inhibition ratio of Y5 agonist-induced food intake by the compounds was calculated as follows; inhibition ratio (%)=[1−(food intake (g) by the compound. treated and Y5 agonist received mice−food intake (g) by the vehicle treated and saline received mice)/(food intake (g) by the vehicle treated and Y5 agonist received mice-food intake (g) by the vehicle treated and saline received mice)]×100. The compounds at 12.5 mg/kg caused a significant inhibition in Y5 agonist induced-food intake compared to the 0.5% hydroxypropylmethyl cellulose solution.

Example 9

CYP Inhibition Test

Using commercially available pooled human hepatic microsome, and employing, as markers, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6), and terfenedine hydroxylation as typical substrate metabolism reactions of human main five CYP enzyme forms (CYP1A2, 2C9, 2C19, 2D6, 3A4), an inhibitory degree of each metabolite production amount by a test compound was assessed.

The reaction conditions were as follows: substrate, 0.5 µmol/L ethoxyresorufin (CYP1A2), 100 µmol/L tolbutamide (CYP2C9), 50 µmol/L S-mephenitoin (CYP2C19), 5 µmol/L dextromethorphan (CYP2D6), 1 µmol/L terfenedine (CYP3A4); reaction time, 15 minutes; reaction temperature, 37° C.; enzyme, pooled human hepatic microsome 0.2 mg protein/mL; test drug concentration, 1, 5, 10, 20 µmol/L (four points).

Each five kinds of substrates, human hepatic microsome, or a test drug in 50 mM Hepes buffer as a reaction solution was added to a 96-well plate at the composition as described above, NADPH, as a cofactor was added to initiate metabolism reactions as markers and, after the incubation at 37° C. for 15 minutes, a methanol/acetonitrile=1/1 (v/v) solution was added to stop the reaction. After the centrifugation at 3000 rpm for 15 minutes, resorufin (CYP1A2 metabolite) in the supernatant was quantified by a fluorescent multilabel counter and tributamide hydroxide (CYP2CP metabolite), mephenyloin 4' hydroxide (CYP2C19 metabolite), dextromethorphan (CYP2D6 metabolite), and terfenadine alcohol (CYP3A4 metabolite) were quantified by LC/MS/MS.

Addition of only DMSO being a solvent dissolving a drug to a reaction system was adopted as a control (100%), remaining activity (%) was calculated at each concentration of a test drug added as the solution and IC50 was calculated by reverse presumption by a logistic model using a concentration and an inhibition rate.

Experiment 10

Test for Metabolic Stability

Test for Metabolic Stability in Human Hepatic Microsomes: To trishydrochloric acid buffer (pH 7.4), were added NADPH (the final concentration was 1 mM in case of oxidative metabolism), Hepatic Microsomes (the final concentration was 0.5 mg protein/ml) and each compound (the final concentration was 2 µM). The mixture was reacted at 37° C. for 0 and 30 minutes. In case of conjugated glucuronic acid, UDPGA (the final concentration is 5 mM) was added instead of NADPH. The reaction was stopped by adding acetonitrile/methanol=1/1 (v/v) which is 2 parts by volume based on 1 part by volume of the reaction solution and then compounds in the centrifugal supernatant were measured by HPLC. By comparing the values between 0 and 30 minutes the disappearance volume of the compounds by the metabolic reaction was calculated to confirm metabolic stability of the compounds of this invention.

Example 11

Powder Solubility Test

Appropriate amounts of the test substances were put into appropriate containers. To the respective containers were added 200 μL of JP-1 fluid (sodium chloride 2.0 g, hydrochloric acid 7.0 mL and water to reach 1000 mL), 200 μL of JP-2 fluid (phosphate buffer (pH 6.8) 500 mL and water 500 mL), and 2004 of 20 mmol/L TCA (sodium taurocholate)/JP-2 fluid (TCA 1.08 g and water to reach 100 mL). In the case that the test compound was dissolved after the addition of the test fluid, the bulk powder was added as appropriate. The containers were sealed, and shaken for 1 hour at 37° C. The mixtures were filtered, and 100 μL of methanol was added to each of the filtrate (100 μL) so that the filtrates were two-fold diluted. The dilution ratio was changed if necessary. The dilutions were observed for bubbles and precipitates, and then the containers were sealed and shaken. Quantification was performed by HPLC with an absolute calibration method.

Formulation Example

The following Formulation Examples are only exemplified and not intended to limit the scope of this invention.

Formulation Example 1

Tablets

| Compound (I) | 15 mg |
|---|---|
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture is crushed, granulated and dried to obtain a suitable size of granules. Next, calcium stearate is added to the granules. Finally, tableting is performed under a compression force.

Formulation Example 2

Capsules

| Compound (I) | 10 mg |
|---|---|
| Magnesium stearate | 10 mg |
| Lactose | 80 mg |

The above ingredients are mixed uniformly to obtain powders or fine granules, and then the obtained mixture is filled into capsules.

Formulation Example 3

Granules

| Compound (I) | 30 g |
|---|---|
| Lactose | 265 g |
| Magnesium stearate | 5 g |

After the above ingredients are mixed uniformly, the mixture is compressed, crushed, granulated and sieved to obtain a suitable size of granules.

The invention claimed is:
1. A compound of formula (I):

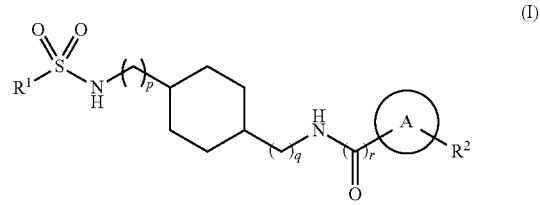

or a pharmaceutically acceptable salt thereof,
wherein $R^1$ is substituted or unsubstituted alkyl, substituted or unsubstituted alkenyl, substituted or unsubstituted alkynyl, substituted or unsubstituted cycloalkyl, substituted or unsubstituted cycloalkenyl or substituted amino,
p is 1, and q and r are 0,
a group of formula:

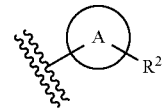

is a group of formula:

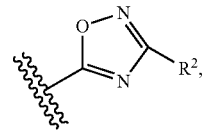

and
$R^2$ is substituted or unsubstituted alkyl, substituted or unsubstituted cycloalkyl, substituted or unsubstituted cycloalkenyl, substituted or unsubstituted aryl, substituted or unsubstituted heteroaryl or substituted or unsubstituted heterocyclyl.

2. The compound of claim 1, or a pharmaceutically acceptable salt thereof, wherein $R^1$ is substituted or unsubstituted alkyl or substituted or unsubstituted cycloalkyl.

3. The compound of claim 2, or a pharmaceutically acceptable salt thereof, wherein $R^1$ is substituted or unsubstituted alkyl.

4. The compound of claim 1, or a pharmaceutically acceptable salt thereof, wherein $R^2$ is substituted or unsubstituted aryl.

5. The compound of claim 1, or a pharmaceutically acceptable salt thereof, wherein $R^2$ is a group of formula:

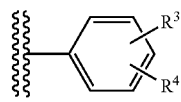

wherein $R^3$ is halogen, alkylsulfonyl, haloalkyl or haloalkyloxy, and $R^4$ is hydrogen, halogen, alkylsulfonyl, haloalkyl or haloalkyloxy.

6. The compound of claim 1, or a pharmaceutically acceptable salt thereof, wherein $R^2$ is substituted or unsubstituted alkyl.

7. The compound of claim 1, or a pharmaceutically acceptable salt thereof, wherein $R^2$ is substituted or unsubstituted haloalkyl.

8. The compound of claim 1, or a pharmaceutically acceptable salt thereof, wherein $R^2$ is substituted or unsubstituted cycloalkyl, substituted or unsubstituted cycloalkenyl or substituted or unsubstituted heterocyclyl.

9. The compound of claim 1, or a pharmaceutically acceptable salt thereof, wherein $R^2$ is substituted or unsubstituted cycloalkyl.

10. A compound of formula (IV):

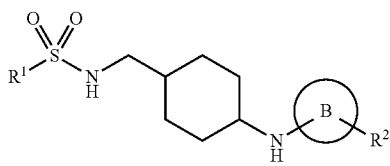

or a pharmaceutically acceptable salt thereof,
wherein $R^1$ is substituted or unsubstituted alkyl,
a group of formula:

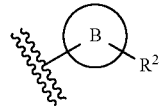

is a group of formula:

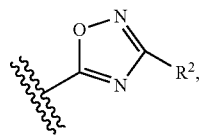

and $R^2$ is substituted or unsubstituted haloalkyl.

11. A pharmaceutical composition comprising: the compound of claim 1, or a pharmaceutically acceptable salt thereof.

12. The pharmaceutical composition of claim 11 having NPY Y5 receptor antagonistic activity.

13. A pharmaceutical composition comprising: the compound of claim 10, or a pharmaceutically acceptable salt thereof.

14. The pharmaceutical composition of claim 13 having NPY Y5 receptor antagonistic activity.

* * * * *